United States Patent
Ross et al.

[11] Patent Number: 6,063,956
[45] Date of Patent: May 16, 2000

[54] ARYL AND HETEROARYLCYCLOPROPYL OXIME ETHERS AND THEIR USE AS FUNGICIDES AND INSECTICIDES

[75] Inventors: Ronald Ross, Jamison; Steven Howard Shaber, Horsham; Duyan Vuong Nguyen, Philadelphia, all of Pa.

[73] Assignee: Rohm and Haas Company, Philadelphia, Pa.

[21] Appl. No.: 09/238,196

[22] Filed: Jan. 27, 1999

[51] Int. Cl.[7] ............... C07C 229/00; C07C 249/00; C07C 233/00; C07C 327/00; A01N 53/00

[52] U.S. Cl. ............... 560/35; 562/440; 564/165; 558/256; 514/531; 514/503; 514/618; 514/619

[58] Field of Search ............... 560/35; 562/440; 564/165; 558/256; 514/531, 563, 619, 618

[56] References Cited

U.S. PATENT DOCUMENTS

| | | |
|---|---|---|
| 5,194,662 | 3/1993 | Brand et al. |
| 5,292,759 | 3/1994 | Brand et al. |
| 5,583,249 | 12/1996 | Pfiffner et al. |
| 5,965,613 | 10/1999 | Isenring et al. |

FOREIGN PATENT DOCUMENTS 9847886  10/1998  WIPO.

*Primary Examiner*—Paul J. Killos
*Attorney, Agent, or Firm*—Guy T. Donatiello; Thomas D. Rogerson

[57] ABSTRACT

Compounds with fungicidal and insecticidal properties having formula

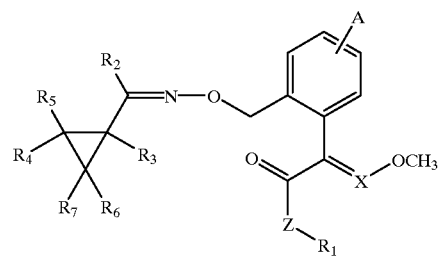

wherein X is N or CH; Z is O, S or $NR_8$; A is hydrogen, halo, cyano, $(C_1-C_{12})$alkyl, or $(C_1-C_{12})$alkoxy; $R_1$ and $R_8$ are independently hydrogen or $(C_1-C_4)$alkyl; $R_2$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, heterocyclic $(C_1-C_4)$alkyl or $C(R_{10})=N-OR_9$; $R_3$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, aryl$(C_3-C_7)$cycloalkyl, heterocyclic or heterocyclic$(C_1-C_4)$alkyl; $R_4$ and $R_5$ are independently hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, $(C_1-C_4)$alkoxycarbonyl, aryl, aralkyl, aryl$(C_3-C_7)$cycloalkyl, heterocyclic or heterocyclic$(C_1-C_4)$alkyl; $R_6$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, $(C_1-C_4)$alkoxycarbonyl, aryl, aralkyl, aryl$(C_3-C_7)$cycloalkyl, heterocyclic or heterocyclic$(C_1-C_4)$alkyl; $R_7$ is aryl, aralkyl, heterocyclic or heterocyclic$(C_1-C_4)$alkyl; $R_9$ is hydrogen, $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, $(C_1-C_4)$alkylcarbonyl, $(C_1-C_4)$alkoxycarbonyl, aryl, or aralkyl; and $R_{10}$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, or heterocyclic$(C_1-C_4)$alkyl.

10 Claims, No Drawings

ARYL AND HETEROARYLCYCLOPROPYL OXIME ETHERS AND THEIR USE AS FUNGICIDES AND INSECTICIDES

The present invention relates to certain aryl cyclopropyl oxime ether structures, compositions containing these compounds and methods for controlling fungi and insects by the use of a fungitoxic or insecticidal amount of these compounds.

It is known that compounds having certain oxime ether structures have been disclosed in U.S. Pat. Nos. 5,194,662 and 5,292,759. We have discovered certain new cyclopropyl oxime ethers which possess a substituted aryl and heterocyclic moieties. These novel derivatives possess broad spectrum fungicidal and insecticidal properties.

The novel cyclopropyloxime ethers of the present invention have the Formula

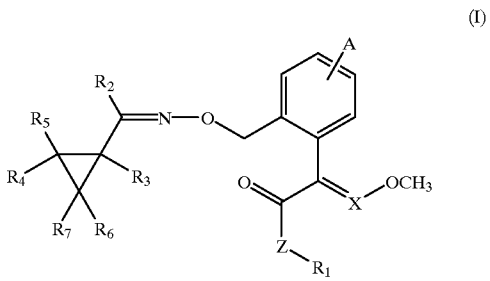

(I)

wherein X is N or CH; Z is O, S, or $NR_8$;

A is hydrogen, halo, cyano, $(C_1-C_{12})$alkyl, or $(C_1-C_{12})$alkoxy;

$R_1$ and $R_8$ are independently hydrogen or $(C_1-C_4)$alkyl;

$R_2$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_1-C_8)$alkenyl, $(C_2-C_8)$alkynyl, halo$(C_2-C_8)$alkynyl, aryl, aralkyl, heterocyclic, heterocyclic$(C_1-C_4)$alkyl and $C(R_{10})$=N—$OR_9$;

$R_3$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_1-C_1)$alkenyl, $(C_2-C_8)$alkynyl, halo$(C_2-C_8)$alkynyl, aryl, aralkyl, aryl$(C_3-C_7)$cycloalkyl, heterocyclic and heterocyclic$(C_1-C_4)$alkyl;

$R_4$ and $R_5$ independently selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, $(C_1-C_4)$alkoxycarbonyl, aryl, aralkyl, aryl$(C_3-C_7)$cycloalkyl, aryl$(C_2-C_8)$alkenyl, heterocyclic and heterocyclic$(C_1-C_4)$alkyl;

$R_6$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_1-C_8)$alkenyl, $(C_2-C_8)$alkynyl, halo$(C_2-C_8)$alkynyl, halo, cyano, $(C_1-C_4)$alkoxycarbonyl, aryl, aralkyl, aryl$(C_3-C_7)$cycloalkyl, aryl$(C_2-C_8)$alkenyl, heterocyclic and heterocyclic$(C_1-C_4)$alkyl;

$R_7$ is selected from the group consisting of aryl, aralkyl, heterocyclic and heterocyclic$(C_1-C_4)$alkyl;

$R_9$ is selected from the group consisting of hydrogen, $(C-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, $(C_1-C_4)$alkylcarbonyl, $(C_1-C_4)$alkoxycarbonyl, aryl, and aralkyl;

$R_{10}$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, and heterocyclic$(C_1-C_4)$alkyl.

The aforementioned $(C_1-C_{12})$alkyl, $(C_2-C_8)$alkenyl, $(C_2-C_8)$alkynyl and $(C_3-C_7)$cycloalkyl groups may be optionally substituted with up to three substituents selected from the group consisting of nitro, halomethyl, $(C_1-C_4)$alkoxycarbonyl, and cyano.

The term alkyl includes both branched and straight chain alkyl groups from 1 to 12 carbon atoms. Typical alkyl groups are methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term alkenyl refers to an ethylenically unsaturated hydrocarbon group, straight or branched, having a chain length of 2 to 8 carbon atoms and 1 or 2 ethylenic bonds. The term haloalkenyl refers to an alkenyl group substituted with 1 to 3 halogen atoms. The term alkynyl refers to an unsaturated hydrocarbon group, straight or branched, having a chain length of 2 to 12 carbon atoms and 1 or 2 acetylenic bonds.

The term aryl includes phenyl or napthyl, which maybe substituted with up to three substituents independently selected from the group consisting of halogen, cyano, trihalomethyl, phenyl, phenoxy, $(C_1-C_4)$alkyl, $(C_1-C_4)$alkoxy, $(C_1-C_4)$alkylthio, $(C_1-C_4)$alkylsulfoxide, halo$(C_1-C_4)$alkyl and halo$(C_1-C_4)$alkoxy.

Typical aryl substituents include but are not limited to 2-chlorophenyl, 3-chlorophenyl, 4-chlorophenyl, 2-fluorophenyl, 3-fluorophenyl, 4-fluorophenyl, 4-bromophenyl, , 2-methylphenyl, 3-methyphenyl, 4-methylphenyl, 2,4-dibromophenyl, 3,5-difluorophenyl, 2,4,6-trichlorophenyl, 2-chloronapthyl, 3-(trifluoromethyl) phenyl, 4-(trifluoromethyl)phenyl and 2-iodo-4-methylphenyl.

The term heterocyclic refers to a substituted or unsubstituted 6 membered unsaturated ring containing one, two or three heteroatoms, preferably one, two or three heteroatoms independently selected from oxygen, nitrogen and sulfur or to a bicyclic unsaturated ring system containing up to 10 atoms including one heteroatom selected from oxygen, nitrogen and sulfur. The term heterocyclic also refers to a 5 membered unsaturated ring containing one, two or three heteroatoms, preferably one or two heteroatoms independently selected from oxygen, nitrogen or sulfur. Examples of heterocycles include but are not limited to 2-, 3- or 4-pyridinyl, pyrazinyl, 2-, 4-, or 5-pyrimidinyl, pyridazinyl, pyrazole, triazolyl, imidazolyl, 2 or 3-thienyl, 2 or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from $(C_1-C_4)$ alkyl, halogen, cyano, nitro and trihalomethyl.

The term aralkyl is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chlorophenyl)ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methyl-phenyl)ethyl, 2-(4-methylphenyl)ethyl, 2-(4-trifluoromethylphenyl)ethyl, 2-(2,4-dichlorophenyl)-ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichloro-phenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(4-trifluoromethylphenyl)propyl, 3-(2,4-dichlorophenyl)propyl and 3-(3,5-dimethylphenyl)propyl. Typical phenbutyl moieties include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methylphenyl)butyl and 4-(2,4-dichlorophenyl)butyl.

Halogen or halo is meant to include iodo, fluoro, bromo and chloro moieties.

Because of the C=C or C=N double bonds, the novel compounds of the general Formula I may be obtained in preparation as E/Z isomeric mixtures. These isomers can be separated into individual components by conventional means. The arylcyclopropanes of Formula I may be obtained in preparation as cis and trans isomeric mixtures which can be separated into individual components by conventional means. Both the individual isomeric compounds and mixtures thereof form subjects of the invention and can be used as fungicides and insecticides.

The present invention also includes the enantiomorphs, salts and complexes of Formula (I).

A preferred embodiment of this invention are the compounds, enantiomorphs, salts and complexes of Formula (I') where A is hydrogen, $R_1$ and $R_2$ are hydrogen or $(C_1-C_4)$alkyl, $R_3$, $R_4$, $R_5$ and $R_6$ are hydrogen and $R_7$ is aryl, aralkyl, or heterocyclic.

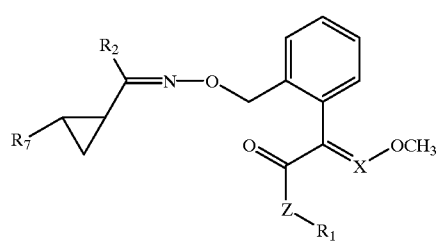

(I')

A more preferred embodiment of this invention are the compounds, enantiomorphs, salts and complexes of Formula (I″) where X is N, Z is NH, $R_2$ is methyl and $R_7$ is aryl.

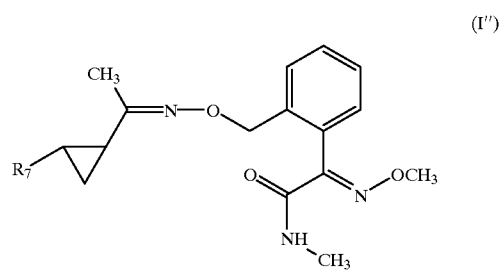

(I″)

Typical compounds encompassed by the present invention of Formula I (where $A=R_4=R_5=R_6=H$) include those compounds presented in Table 1 of Formula IV (X=CH and Z is O) where $R_2$, $R_3$ and $R_7$ are defined in Table 1.

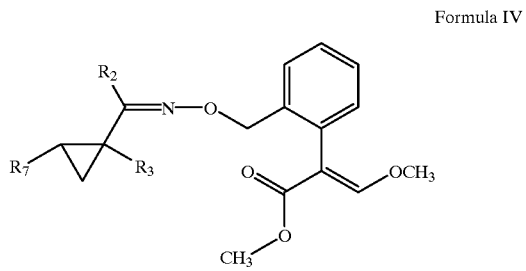

Formula IV

TABLE 1

| Compd | $R_2$ | $R_3$ | $R_7$ | Properties/Comments |
|---|---|---|---|---|
| 1.1 | H | H | Ph | |
| 1.2 | H | H | 4-Cl(Ph) | |
| 1.3 | H | H | 4-Br(Ph) | |
| 1.4 | H | H | 4-F(Ph) | |
| 1.5 | H | H | 4-OCH$_3$(Ph) | |
| 1.6 | H | H | 4-CF$_3$(Ph) | |
| 1.7 | H | H | 4-NO$_2$(Ph) | |
| 1.8 | H | H | 2,4-Cl(Ph) | |
| 1.9 | H | H | 2,4-F(Ph) | |
| 1.10 | H | H | 3,4-F(Ph) | |
| 1.11 | CH$_3$ | H | Ph | oil |
| 1.12 | CH$_3$ | H | 2-Cl(Ph) | |
| 1.13 | CH$_3$ | H | 3-Cl(Ph) | |
| 1.14 | CH$_3$ | H | 4-Cl(Ph) | oil |
| 1.15 | CH$_3$ | H | 2-Br(Ph) | |
| 1.16 | CH$_3$ | H | 3-Br(Ph) | |
| 1.17 | CH$_3$ | H | 4-Br(Ph) | |
| 1.18 | CH$_3$ | H | 2-F(Ph) | |
| 1.19 | CH$_3$ | H | 3-F(Ph) | |
| 1.20 | CH$_3$ | H | 4-F(Ph) | |
| 1.21 | CH$_3$ | H | 2-OCH$_3$(Ph) | |
| 1.22A | CH$_3$ | H | 3-OCH$_3$(Ph) | oil, isomer A |
| 1.22B | CH$_3$ | H | 3-OCH$_3$(Ph) | oil, isomer B |
| 1.23 | CH$_3$ | H | 4-OCH$_3$(Ph) | |
| 1.24 | CH$_3$ | H | 2-CH$_3$(Ph) | |
| 1.25 | CH$_3$ | H | 3-CH$_3$(Ph) | |
| 1.26 | CH$_3$ | H | 4-CH$_3$(Ph) | |
| 1.27 | CH$_3$ | H | 2-CF$_3$(Ph) | oil, isomer A |
| 1.28 | CH$_3$ | H | 3-CF$_3$(Ph) | |
| 1.29 | CH$_3$ | H | 4-CF$_3$(Ph) | |
| 1.30 | CH$_3$ | H | 2-NO$_2$(Ph) | |
| 1.31 | CH$_3$ | H | 3-NO$_2$(Ph) | |
| 1.32 | CH$_3$ | H | 4-NO$_2$(Ph) | |
| 1.33 | CH$_3$ | H | 2,3-Cl(Ph) | |
| 1.34 | CH$_3$ | H | 2,4-Cl(Ph) | |
| 1.35 | CH$_3$ | H | 2,5-Cl(Ph) | |
| 1.36 | CH$_3$ | H | 2,6-Cl(Ph) | |

TABLE 1-continued

| Compd | R$_2$ | R$_3$ | R$_7$ | Properties/Comments |
|---|---|---|---|---|
| 1.37 | CH$_3$ | H | 3,4-Cl(Ph) | |
| 1.38 | CH$_3$ | H | 3,5-Cl(Ph) | |
| 1.39 | CH$_3$ | H | 2,3-F(Ph) | |
| 1.40 | CH$_3$ | H | 2,4-F(Ph) | |
| 1.41 | CH$_3$ | H | 2,5-F(Ph) | |
| 1.42 | CH$_3$ | H | 2,6-F(Ph) | |
| 1.43 | CH$_3$ | H | 3,4-F(Ph) | |
| 1.44 | CH$_3$ | H | 3,5-FPh) | |
| 1.45 | C$_2$H$_5$ | H | Ph | |
| 1.46 | C$_2$H$_5$ | H | 2-Cl(Ph) | |
| 1.47 | C$_2$H$_5$ | H | 3-Cl(Ph) | |
| 1.48 | C$_2$H$_5$ | H | 4-Cl(Ph) | |
| 1.49 | C$_2$H$_5$ | H | 4-Br(Ph) | |
| 1.50 | C$_2$H$_5$ | H | 4-F(Ph) | |
| 1.51 | C$_2$H$_5$ | H | 4-OCH$_3$(Ph) | |
| 1.52 | C$_2$H$_5$ | H | 4-CH$_3$(Ph) | |
| 1.53 | C$_2$H$_5$ | H | 4-NO$_2$(Ph) | |
| 1.54 | C$_2$H$_5$ | H | 2,4-Cl(Ph) | |
| 1.55 | C$_2$H$_5$ | H | 2,4-F(Ph) | |
| 1.56 | n-C$_3$H$_7$ | H | Ph | |
| 1.57 | n-C$_3$H$_7$ | H | 2-Cl(Ph) | |
| 1.58 | n-C$_3$H$_7$ | H | 3-Cl(Ph) | |
| 1.59 | n-C$_3$H$_7$ | H | 4-Cl(Ph) | |
| 1.60 | n-C$_3$H$_7$ | H | 4-F(Ph) | |
| 1.61A | n-C$_3$H$_7$ | H | 3-OCH$_3$(Ph) | oil, isomer A |
| 1.61B | n-C$_3$H$_7$ | H | 3-OCH$_3$(Ph) | oil, isomer B |
| 1.62 | n-C$_3$H$_7$ | H | 4-OCH$_3$(Ph) | |
| 1.63 | n-C$_3$H$_7$ | H | 4-CH$_3$(Ph) | |
| 1.64 | n-C$_3$H$_7$ | H | 4-NO$_2$(Ph) | |
| 1.65 | n-C$_3$H$_7$ | H | 2,4-Cl(Ph) | |
| 1.66 | n-C$_3$H$_7$ | H | 2,4-F(Ph) | |
| 1.67 | iso-C$_3$H$_7$ | H | Ph | oil |
| 1.68 | iso-C$_3$H$_7$ | H | 2-Cl(Ph) | |
| 1.69 | iso-C$_3$H$_7$ | H | 3-Cl(Ph) | |
| 1.70 | iso-C$_3$H$_7$ | H | 4-Cl(Ph) | |
| 1.71 | iso-C$_3$H$_7$ | H | 4-Br(Ph) | |
| 1.72 | iso-C$_3$H$_7$ | H | 4-F(Ph) | |
| 1.73 | iso-C$_3$H$_7$ | H | 4-OCH$_3$(Ph) | |
| 1.74 | iso-C$_3$H$_7$ | H | 4-CH$_3$(Ph) | |
| 1.75 | iso-C$_3$H$_7$ | H | 4-NO$_2$(Ph) | |
| 1.76 | iso-C$_3$H$_7$ | H | 2,4-Cl(Ph) | |
| 1.77 | iso-C$_3$H$_7$ | H | 2,4-F(Ph) | |
| 1.78 | n-C$_4$H$_9$ | H | Ph | |
| 1.79 | n-C$_4$H$_9$ | H | 2-Cl(Ph) | |
| 1.80 | n-C$_4$H$_9$ | H | 3-Cl(Ph) | |
| 1.81 | n-C$_4$H$_9$ | H | 4-Cl(Ph) | |
| 1.82 | n-C$_4$H$_9$ | H | 4-Br(Ph) | |
| 1.83 | n-C$_4$H$_9$ | H | 4-F(Ph) | |
| 1.84 | n-C$_4$H$_9$ | H | 4-OCH$_3$(Ph) | |
| 1.85 | n-C$_4$H$_9$ | H | 4-CH$_3$(Ph) | |
| 1.86 | n-C$_4$H$_9$ | H | 4-NO$_2$(Ph) | |
| 1.87 | n-C$_4$H$_9$ | H | 2,4-Cl(Ph) | |
| 1.88 | n-C$_4$H$_9$ | H | 2,4-F(Ph) | |
| 1.89 | iso-C$_4$H$_9$ | H | Ph | |
| 1.90 | iso-C$_4$H$_9$ | H | 2-Cl(Ph) | |
| 1.91 | iso-C$_4$H$_9$ | H | 3-Cl(Ph) | |
| 1.92 | iso-C$_4$H$_9$ | H | 4-Cl(Ph) | |
| 1.93 | iso-C$_4$H$_9$ | H | 4-F(Ph) | |
| 1.94 | iso-C$_4$H$_9$ | H | 3-OCH$_3$(Ph) | oil |
| 1.95 | iso-C$_4$H$_9$ | H | 4-OCH$_3$(Ph) | |
| 1.96 | iso-C$_4$H$_9$ | H | 4-CH$_3$(Ph) | |
| 1.97 | iso-C$_4$H$_9$ | H | 4-NO$_2$(Ph) | |
| 1.98 | iso-C$_4$H$_9$ | H | 2,4-Cl(Ph) | |
| 1.99 | iso-C$_4$H$_9$ | H | 2,4-F(Ph) | |
| 1.100 | c-C$_3$H$_5$ | H | Ph | |
| 1.101 | c-C$_3$H$_5$ | H | 2-Cl(Ph) | |
| 1.102 | c-C$_3$H$_5$ | H | 3-Cl(Ph) | oil |
| 1.103 | c-C$_3$H$_5$ | H | 4-Cl(Ph) | |
| 1.104 | c-C$_3$H$_5$ | H | 4-F(Ph) | |
| 1.105 | c-C$_3$H$_5$ | H | 3-OCH$_3$(Ph) | oil |
| 1.106 | c-C$_3$H$_5$ | H | 4-OCH$_3$(Ph) | |
| 1.107 | c-C$_3$H$_5$ | H | 4-CH$_3$(Ph) | |
| 1.108 | c-C$_3$H$_5$ | H | 4-NO$_2$(Ph) | |
| 1.109 | c-C$_3$H$_5$ | H | 2,4-Cl(Ph) | |
| 1.110 | c-C$_3$H$_5$ | H | 2,4-F(Ph) | |
| 1.111 | 1-CH$_3$-c-C$_3$H$_5$ | H | Ph | |
| 1.112 | 1-CH$_3$-c-C$_3$H$_5$ | H | 2-Cl(Ph) | |
| 1.113 | 1-CH$_3$-c-C$_3$H$_5$ | H | 3-Cl(Ph) | |
| 1.114 | 1-CH$_3$-c-C$_3$H$_5$ | H | 4-Cl(Ph) | |
| 1.115 | 1-CH$_3$-c-C$_3$H$_5$ | H | 4-Br(Ph) | |
| 1.116A | 1-CH$_3$-c-C$_3$H$_5$ | H | 3-OCH$_3$(Ph) | oil, isomer A |
| 1.116 | 1-CH$_3$-c-C$_3$H$_5$ | H | 3-OCH$_3$(Ph) | oil |
| 1.117 | 1-CH$_3$-c-C$_3$H$_5$ | H | 4-OCH$_3$(Ph) | |
| 1.118 | 1-CH$_3$-c-C$_3$H$_5$ | H | 4-CH$_3$(Ph) | |
| 1.119 | 1-CH$_3$-c-C$_3$H$_5$ | H | 4-NO$_2$(Ph) | |
| 1.120 | 1-CH$_3$-c-C$_3$H$_5$ | H | 2,4-Cl(Ph) | |
| 1.121 | 1-CH$_3$-c-C$_3$H$_5$ | H | 2,4-F(Ph) | |
| 1.122 | C(H)=N—OCH$_3$ | H | Ph | |
| 1.123 | C(H)=N—OCH$_3$ | H | 2-Cl(Ph) | |
| 1.124 | C(H)=N—OCH$_3$ | H | 3-Cl(Ph) | |
| 1.125 | C(H)=N—OCH$_3$ | H | 4-Cl(Ph) | |
| 1.126 | C(H)=N—OCH$_3$ | H | 4-Br(Ph) | |
| 1.127 | C(H)=N—OCH$_3$ | H | 4-F(Ph) | |
| 1.128 | C(H)=N—OCH$_3$ | H | 4-OCH$_3$(Ph) | |
| 1.129 | C(H)=N—OCH$_3$ | H | 4-CH$_3$(Ph) | |
| 1.130 | C(H)=N—OCH$_3$ | H | 4-NO$_2$(Ph) | |
| 1.131 | C(H)=N—OCH$_3$ | H | 2,4-Cl(Ph) | |
| 1.132 | C(H)=N—OCH$_3$ | H | 2,4-F(Ph) | |
| 1.133 | C(CH$_3$)=N—OCH$_3$ | H | Ph | oil, isomer A |
| 1.134 | C(CH$_3$)=N—OCH$_3$ | H | 2-Cl(Ph) | |
| 1.135 | C(CH$_3$)=N—OCH$_3$ | H | 3-Cl(Ph) | |
| 1.136 | C(CH$_3$)=N—OCH$_3$ | H | 4-Cl(Ph) | |
| 1.137 | C(CH$_3$)=N—OCH$_3$ | H | 4-Br(Ph) | |
| 1.138 | C(CH$_3$)=N—OCH$_3$ | H | 4-F(Ph) | |
| 1.139 | C(CH$_3$)=N—OCH$_3$ | H | 4-OCH$_3$(Ph) | |
| 1.140 | C(CH$_3$)=N—OCH$_3$ | H | 4-CH$_3$(Ph) | |
| 1.141 | C(CH$_3$)=N—OCH$_3$ | H | 4-NO$_2$(Ph) | |
| 1.142 | C(CH$_3$)=N—OCH$_3$ | H | 2,4-Cl(Ph) | |
| 1.143 | C(CH$_3$)=N—OCH$_3$ | H | 2,4-F(Ph) | |
| 1.144 | C(C$_2$H$_5$)=N—OCH$_3$ | H | Ph | oil, isomer A |
| 1.145 | C(C$_2$H$_5$)=N—OCH$_3$ | H | 2-Cl(Ph) | |
| 1.146 | C(C$_2$H$_5$)=N—OCH$_3$ | H | 3-Cl(Ph) | |
| 1.147 | C(C$_2$H$_5$)=N—OCH$_3$ | H | 4-Cl(Ph) | |
| 1.148 | C(C$_2$H$_5$)=N—OCH$_3$ | H | 4-Br(Ph) | |
| 1.149 | C(C$_2$H$_5$)=N—OCH$_3$ | H | 4-F(Ph) | |
| 1.150 | C(C$_2$H$_5$)=N—OCH$_3$ | H | 4-OCH$_3$(Ph) | |
| 1.151 | C(C$_2$H$_5$)=N—OCH$_3$ | H | 4-CH$_3$(Ph) | |
| 1.152 | C(C$_2$H$_5$)=N—OCH$_3$ | H | 4-NO$_2$(Ph) | |
| 1.153 | C(C$_2$H$_5$)=N—OCH$_3$ | H | 2,4-Cl(Ph) | |
| 1.154 | C(C$_2$H$_5$)=N—OCH$_3$ | H | 2,4-F(Ph) | |
| 1.155 | Ph | H | Ph | oil |
| 1.156 | Ph | H | 2-Cl(Ph) | |
| 1.157 | Ph | H | 3-Cl(Ph) | oil |
| 1.158 | Ph | H | 4-Cl(Ph) | |
| 1.159 | Ph | H | 3-OCH$_3$(Ph) | oil |
| 1.160 | 4-Cl(Ph) | H | Ph | oil |
| 1.161 | 4-F(Ph) | H | Ph | |
| 1.162 | 4-F(Ph) | H | 4-F(Ph) | |
| 1.163 | 4-CF$_3$(Ph) | H | Ph | |
| 1.164 | 4-CF$_3$(Ph) | H | 4-CF$_3$(Ph) | |
| 1.165 | 2,4-Cl(Ph) | H | Ph | |
| 1.166 | 2,4-Cl(Ph) | H | 2,4-Cl(Ph) | |
| 1.167 | 2,4-F(Ph) | H | Ph | |
| 1.168 | CH$_3$ | CH$_3$ | Ph | |
| 1.169 | C$_2$H$_5$ | CH$_3$ | 2-Cl(Ph) | |
| 1.170 | n-C$_3$H$_7$ | CH$_3$ | 3-Cl(Ph) | |
| 1.171 | iso-C$_3$H$_7$ | CH$_3$ | 4-Cl(Ph) | |
| 1.172 | n-C$_4$H$_9$ | CH$_3$ | 4-Br(Ph) | |
| 1.173 | iso-C$_4$H$_9$ | CH$_3$ | 4-F(Ph) | |
| 1.174 | c-C$_3$H$_5$ | CH$_3$ | 4-OCH$_3$(Ph) | |
| 1.175 | 1-CH$_3$-c-C$_3$H$_5$ | CH$_3$ | 4-CH$_3$(Ph) | |
| 1.176 | C(H)=N—OCH$_3$ | CH$_3$ | 4-NO$_2$(Ph) | |
| 1.177 | C(CH$_3$)=N—OCH$_3$ | CH$_3$ | 2,4-Cl(Ph) | |
| 1.178 | C(C$_2$H$_5$)=N—OCH$_3$ | CH$_3$ | 2,4-F(Ph) | |
| 1.179 | Ph | CH$_3$ | Ph | |
| 1.180 | Ph | CH$_3$ | 2-Cl(Ph) | |
| 1.181 | Ph | CH$_3$ | 3-Cl(Ph) | |
| 1.182 | Ph | CH$_3$ | 4-Cl(Ph) | |
| 1.183 | 4-Cl(Ph) | CH$_3$ | Ph | |
| 1.184 | 4-Cl(Ph) | CH$_3$ | 4-Cl(Ph) | |
| 1.185 | 4-F(Ph) | CH$_3$ | Ph | |
| 1.186 | 4-F(Ph) | CH$_3$ | 4-F(Ph) | |

TABLE 1-continued

| Compd | R$_2$ | R$_3$ | R$_7$ | Properties/Comments |
|---|---|---|---|---|
| 1.187 | 4-CF$_3$(Ph) | CH$_3$ | Ph | |
| 1.188 | 4-CF$_3$(Ph) | CH$_3$ | 4-CF$_3$(Ph) | |
| 1.189 | 2,4-Cl(Ph) | CH$_3$ | Ph | |
| 1.190 | 2,4-Cl(Ph) | CH$_3$ | 2,4-Cl(Ph) | |
| 1.191 | 2,4-F(Ph) | CH$_3$ | Ph | |

Typical compounds encompassed by the present invention of Formula I (where A=R$_4$=R$_5$=R$_6$=H) include those compounds presented in Table 2 of Formula V (X=N and Z is O) where R$_2$, R$_3$, and R$_7$ are defined in Table 2

Formula V

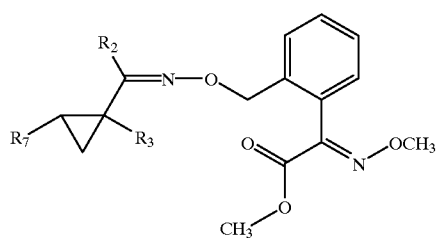

Formula V

TABLE 2

| Compd | R$_2$ | R$_3$ | R$_7$ | Properties/Comments |
|---|---|---|---|---|
| 2.1A | H | H | Ph | oil, isomer A |
| 2.1B | H | H | Ph | oil, isomer B |
| 2.2 | H | H | 4-Cl(Ph) | |
| 2.3 | H | H | 4-Br(Ph) | |
| 2.4 | H | H | 4-F(Ph) | |
| 2.5 | H | H | 4-OCH$_3$(Ph) | |
| 2.6 | H | H | 4-CF$_3$(Ph) | |
| 2.7 | H | H | 4-NO$_2$(Ph) | |
| 2.8 | H | H | 2,4-Cl(Ph) | |
| 2.9 | H | H | 2,4-F(Ph) | |
| 2.10 | H | H | 3,4-F(Ph) | |
| 2.11 | CH$_3$ | H | Ph | oil |
| 2.11A | CH$_3$ | H | Ph | oil, isomer A |
| 2.11B | CH$_3$ | H | Ph | oil, isomer B |
| 2.12A | CH$_3$ | H | 2-ClAr | oil, isomer A |
| 2.12B | CH$_3$ | H | 2-ClAr | oil, isomer B |
| 2.13A | CH$_3$ | H | 3-Cl(Ph) | oil, isomer A |
| 2.13B | CH$_3$ | H | 3-Cl(Ph) | oil, isomer B |
| 2.14A | CH$_3$ | H | 4-Cl(Ph) | oil, isomer A |
| 2.14B | CH$_3$ | H | 4-Cl(Ph) | oil, isomer B |
| 2.15 | CH$_3$ | H | 2-Br(Ph) | |
| 2.16 | CH$_3$ | H | 3-Br(Ph) | |
| 2.17 | CH$_3$ | H | 4-Br(Ph) | |
| 2.18 | CH$_3$ | H | 2-F(Ph) | oil, isomer B |
| 2.19 | CH$_3$ | H | 3-F(Ph) | oil, isomer A |
| 2.20A | CH$_3$ | H | 4-F(Ph) | oil, isomer A |
| 2.20B | CH$_3$ | H | 4-F(Ph) | oil, isomer B |
| 2.21A | CH$_3$ | H | 2-OCH$_3$(Ph) | oil, isomer A |
| 2.21B | CH$_3$ | H | 2-OCH$_3$(Ph) | oil, isomer B |
| 2.22A | CH$_3$ | H | 3-OCH$_3$(Ph) | oil, isomer A |
| 2.22B | CH$_3$ | H | 3-OCH$_3$(Ph) | oil, isomer B |
| 2.23A | CH$_3$ | H | 4-OCH$_3$(Ph) | oil, isomer A |
| 2.23B | CH$_3$ | H | 4-OCH$_3$(Ph) | oil, isomer B |
| 2.24 | CH$_3$ | H | 2-CH$_3$(Ph) | oil, isomer A |
| 2.25A | CH$_3$ | H | 3-CH$_3$(Ph) | oil, isomer A |
| 2.25B | CH$_3$ | H | 3-CH$_3$(Ph) | oil, isomer B |
| 2.26A | CH$_3$ | H | 4-CH$_3$(Ph) | oil, isomer A |
| 2.26B | CH$_3$ | H | 4-CH$_3$(Ph) | oil, isomer B |
| 2.27 | CH$_3$ | H | 2-CF$_3$(Ph) | oil, isomer A |

TABLE 2-continued

| Compd | R$_2$ | R$_3$ | R$_7$ | Properties/Comments |
|---|---|---|---|---|
| 2.28 | CH$_3$ | H | 3-CF$_3$(Ph) | oil, isomer A |
| 2.29 | CH$_3$ | H | 4-CF$_3$(Ph) | |
| 2.30 | CH$_3$ | H | 2-NO$_2$(Ph) | |
| 2.31 | CH$_3$ | H | 3-NO$_2$(Ph) | |
| 2.32 | CH$_3$ | H | 4-NO$_2$(Ph) | |
| 2.33 | CH$_3$ | H | 2,3-Cl(Ph) | oil, isomer B |
| 2.34 | CH$_3$ | H | 2,4-Cl(Ph) | oil, isomer A |
| 2.35 | CH$_3$ | H | 2,5-Cl(Ph) | |
| 2.36 | CH$_3$ | H | 2,6-Cl(Ph) | |
| 2.37A | CH$_3$ | H | 3,4-Cl(Ph) | oil, isomer A |
| 2.37B | CH$_3$ | H | 3,4-Cl(Ph) | oil, isomer B |
| 2.38 | CH$_3$ | H | 3,5-Cl(Ph) | |
| 2.39 | CH$_3$ | H | 2,3-F(Ph) | |
| 2.40 | CH$_3$ | H | 2,4-F(Ph) | |
| 2.41 | CH$_3$ | H | 2,5-F(Ph) | |
| 2.42 | CH$_3$ | H | 2,6-F(Ph) | |
| 2.43 | CH$_3$ | H | 3,4-F(Ph) | |
| 2.44 | CH$_3$ | H | 3,5-FPh) | |
| 2.45 | C$_2$H$_5$ | H | Ph | |
| 2.46 | C$_2$H$_5$ | H | 2-Cl(Ph) | |
| 2.47 | C$_2$H$_5$ | H | 3-Cl(Ph) | |
| 2.48 | C$_2$H$_5$ | H | 4-Cl(Ph) | |
| 2.49 | C$_2$H$_5$ | H | 4-Br(Ph) | |
| 2.50 | C$_2$H$_5$ | H | 4-F(Ph) | |
| 2.51 | C$_2$H$_5$ | H | 4-OCH$_3$(Ph) | |
| 2.52 | C$_2$H$_5$ | H | 4-CH$_3$(Ph) | |
| 2.53 | C$_2$H$_5$ | H | 4-NO$_2$(Ph) | |
| 2.54 | C$_2$H$_5$ | H | 2,4-Cl(Ph) | |
| 2.55 | C$_2$H$_5$ | H | 2,4-F(Ph) | |
| 2.56 | n-C$_3$H$_7$ | H | Ph | |
| 2.57 | n-C$_3$H$_7$ | H | 2-Cl(Ph) | |
| 2.58 | n-C$_3$H$_7$ | H | 3-Cl(Ph) | |
| 2.59 | n-C$_3$H$_7$ | H | 4-Cl(Ph) | |
| 2.60 | n-C$_3$H$_7$ | H | 4-Br(Ph) | |
| 2.61 | n-C$_3$H$_7$ | H | 4-F(Ph) | |
| 2.62 | n-C$_3$H$_7$ | H | 4-OCH$_3$(Ph) | |
| 2.63 | n-C$_3$H$_7$ | H | 4-CH$_3$(Ph) | |
| 2.64 | n-C$_3$H$_7$ | H | 4-NO$_2$(Ph) | |
| 2.65 | n-C$_3$H$_7$ | H | 2,4-Cl(Ph) | |
| 2.66 | n-C$_3$H$_7$ | H | 2,4-F(Ph) | |
| 2.67 | iso-C$_3$H$_7$ | H | Ph | oil, isomer A |
| 2.68 | iso-C$_3$H$_7$ | H | 2-Cl(Ph) | |
| 2.69 | iso-C$_3$H$_7$ | H | 3-Cl(Ph) | |
| 2.70 | iso-C$_3$H$_7$ | H | 4-Cl(Ph) | |
| 2.71 | iso-C$_3$H$_7$ | H | 4-Br(Ph) | |
| 2.72 | iso-C$_3$H$_7$ | H | 4-F(Ph) | |
| 2.73 | iso-C$_3$H$_7$ | H | 4-OCH$_3$(Ph) | |
| 2.74 | iso-C$_3$H$_7$ | H | 4-CH$_3$(Ph) | |
| 2.75 | iso-C$_3$H$_7$ | H | 4-NO$_2$(Ph) | |
| 2.76 | iso-C$_3$H$_7$ | H | 2,4-Cl(Ph) | |
| 2.77 | iso-C$_3$H$_7$ | H | 2,4-F(Ph) | |
| 2.78 | n-C$_4$H$_9$ | H | Ph | |
| 2.79 | n-C$_4$H$_9$ | H | 2-Cl(Ph) | |
| 2.80 | n-C$_4$H$_9$ | H | 3-Cl(Ph) | |
| 2.81 | n-C$_4$H$_9$ | H | 4-Cl(Ph) | |
| 2.82 | n-C$_4$H$_9$ | H | 4-Br(Ph) | |
| 2.83 | n-C$_4$H$_9$ | H | 4-F(Ph) | |
| 2.84 | n-C$_4$H$_9$ | H | 4-OCH$_3$(Ph) | |
| 2.85 | n-C$_4$H$_9$ | H | 4-CH$_3$(Ph) | |
| 2.86 | n-C$_4$H$_9$ | H | 4-NO$_2$(Ph) | |
| 2.87 | n-C$_4$H$_9$ | H | 2,4-Cl(Ph) | |
| 2.88 | n-C$_4$H$_9$ | H | 2,4-F(Ph) | |
| 2.89 | iso-C$_4$H$_9$ | H | Ph | |
| 2.90 | iso-C$_4$H$_9$ | H | 2-Cl(Ph) | |
| 2.91 | iso-C$_4$H$_9$ | H | 3-Cl(Ph) | |
| 2.92 | iso-C$_4$H$_9$ | H | 4-Cl(Ph) | |
| 2.93 | iso-C$_4$H$_9$ | H | 4-Br(Ph) | |
| 2.94 | iso-C$_4$H$_9$ | H | 4-F(Ph) | |
| 2.95 | iso-C$_4$H$_9$ | H | 4-OCH$_3$(Ph) | |
| 2.96 | iso-C$_4$H$_9$ | H | 4-CH$_3$(Ph) | |
| 2.97 | iso-C$_4$H$_9$ | H | 4-NO$_2$(Ph) | |
| 2.98 | iso-C$_4$H$_9$ | H | 2,4-Cl(Ph) | |
| 2.99 | iso-C$_4$H$_9$ | H | 2,4-F(Ph) | |
| 2.100 | c-C$_3$H$_5$ | H | Ph | |
| 2.101 | c-C$_3$H$_5$ | H | 2-Cl(Ph) | |
| 2.102 | c-C$_3$H$_5$ | H | 3-Cl(Ph) | |

TABLE 2-continued

| Compd | R$_2$ | R$_3$ | R$_7$ | Properties/Comments |
|---|---|---|---|---|
| 2.103 | c-C$_3$H$_5$ | H | 4-Cl(Ph) | |
| 2.104 | c-C$_3$H$_5$ | H | 4-Br(Ph) | |
| 2.105 | c-C$_3$H$_5$ | H | 4-F(Ph) | |
| 2.106 | c-C$_3$H$_5$ | H | 4-OCH$_3$(Ph) | |
| 2.107 | c-C$_3$H$_5$ | H | 4-CH$_3$(Ph) | |
| 2.108 | c-C$_3$H$_5$ | H | 4-NO$_2$(Ph) | |
| 2.109 | c-C$_3$H$_5$ | H | 2,4-Cl(Ph) | |
| 2.110 | c-C$_3$H$_5$ | H | 2,4-F(Ph) | |
| 2.111 | 1-CH$_3$-c-C$_3$H$_5$ | H | Ph | |
| 2.112 | 1-CH$_3$-c-C$_3$H$_5$ | H | 2-Cl(Ph) | |
| 2.113 | 1-CH$_3$-c-C$_3$H$_5$ | H | 3-Cl(Ph) | |
| 2.114 | 1-CH$_3$-c-C$_3$H$_5$ | H | 4-Cl(Ph) | |
| 2.115 | 1-CH$_3$-c-C$_3$H$_5$ | H | 4-Br(Ph) | |
| 2.116 | 1-CH$_3$-c-C$_3$H$_5$ | H | 4-F(Ph) | |
| 2.117 | 1-CH$_3$-c-C$_3$H$_5$ | H | 4-OCH$_3$(Ph) | |
| 2.118 | 1-CH$_3$-c-C$_3$H$_5$ | H | 4-CH$_3$(Ph) | |
| 2.119 | 1-CH$_3$-c-C$_3$H$_5$ | H | 4-NO$_2$(Ph) | |
| 2.120 | 1-CH$_3$-c-C$_3$H$_5$ | H | 2,4-Cl(Ph) | |
| 2.121 | 1-CH$_3$-c-C$_3$H$_5$ | H | 2,4-F(Ph) | |
| 2.122 | C(H)=N—OCH$_3$ | H | Ph | |
| 2.123 | C(H)=N—OCH$_3$ | H | 2-Cl(Ph) | |
| 2.124 | C(H)=N—OCH$_3$ | H | 3-Cl(Ph) | |
| 2.125 | C(H)=N—OCH$_3$ | H | 4-Cl(Ph) | |
| 2.126 | C(H)=N—OCH$_3$ | H | 4-Br(Ph) | |
| 2.127 | C(H)=N—OCH$_3$ | H | 4-F(Ph) | |
| 2.128 | C(H)=N—OCH$_3$ | H | 4-OCH$_3$(Ph) | |
| 2.129 | C(H)=N—OCH$_3$ | H | 4-CH$_3$(Ph) | |
| 2.130 | C(H)=N—OCH$_3$ | H | 4-NO$_2$(Ph) | |
| 2.131 | C(H)=N—OCH$_3$ | H | 2,4-Cl(Ph) | |
| 2.132 | C(H)=N—OCH$_3$ | H | 2,4-F(Ph) | |
| 2.133 | C(CH$_3$)=N—OCH$_3$ | H | Ph | |
| 2.134 | C(CH$_3$)=N—OCH$_3$ | H | 2-Cl(Ph) | |
| 2.135 | C(CH$_3$)=N—OCH$_3$ | H | 3-Cl(Ph) | |
| 2.136 | C(CH$_3$)=N—OCH$_3$ | H | 4-Cl(Ph) | |
| 2.137 | C(CH$_3$)=N—OCH$_3$ | H | 4-Br(Ph) | |
| 2.138 | C(CH$_3$)=N—OCH$_3$ | H | 4-F(Ph) | |
| 2.139 | C(CH$_3$)=N—OCH$_3$ | H | 4-OCH$_3$(Ph) | |
| 2.140 | C(CH$_3$)=N—OCH$_3$ | H | 4-CH$_3$(Ph) | |
| 2.141 | C(CH$_3$)=N—OCH$_3$ | H | 4-NO$_2$(Ph) | |
| 2.142 | C(CH$_3$)=N—OCH$_3$ | H | 2,4-Cl(Ph) | |
| 2.143 | C(CH$_3$)=N—OCH$_3$ | H | 2,4-F(Ph) | |
| 2.144 | C(C$_2$H$_5$)=N—OCH$_3$ | H | Ph | oil, isomer A |
| 2.145 | C(C$_2$H$_5$)=N—OCH$_3$ | H | 2-Cl(Ph) | |
| 2.146 | C(C$_2$H$_5$)=N—OCH$_3$ | H | 3-Cl(Ph) | |
| 2.147 | C(C$_2$H$_5$)=N—OCH$_3$ | H | 4-Cl(Ph) | |
| 2.148 | C(C$_2$H$_5$)=N—OCH$_3$ | H | 4-Br(Ph) | |
| 2.149 | C(C$_2$H$_5$)=N—OCH$_3$ | H | 4-F(Ph) | |
| 2.150 | C(C$_2$H$_5$)=N—OCH$_3$ | H | 4-OCH$_3$(Ph) | |
| 2.151 | C(C$_2$H$_5$)=N—OCH$_3$ | H | 4-CH$_3$(Ph) | |
| 2.152 | C(C$_2$H$_5$)=N—OCH$_3$ | H | 4-NO$_2$(Ph) | |
| 2.153 | C(C$_2$H$_5$)=N—OCH$_3$ | H | 2,4-Cl(Ph) | |
| 2.154 | C(C$_2$H$_5$)=N—OCH$_3$ | H | 2,4-F(Ph) | |
| 2.155 | Ph | H | Ph | |
| 2.156 | Ph | H | 2-Cl(Ph) | |
| 2.157 | Ph | H | 3-Cl(Ph) | |
| 2.158 | Ph | H | 4-Cl(Ph) | |
| 2.159 | 4-Cl(Ph) | H | Ph | |
| 2.160 | 4-Cl(Ph) | H | 4-Cl(Ph) | |
| 2.161 | 4-F(Ph) | H | Ph | |
| 2.162 | 4-F(Ph) | H | 4-F(Ph) | |
| 2.163 | 4-CF$_3$(Ph) | H | Ph | |
| 2.164 | 4-CF$_3$(Ph) | H | 4-CF$_3$(Ph) | |
| 2.165 | 2,4-Cl(Ph) | H | Ph | |
| 2.166 | 2,4-Cl(Ph) | H | 2,4-Cl(Ph) | |
| 2.167 | 2,4-F(Ph) | H | Ph | |
| 2.168 | CH$_3$ | CH$_3$ | Ph | |
| 2.169 | C$_2$H$_5$ | CH$_3$ | 2-Cl(Ph) | |
| 2.170 | n-C$_3$H$_7$ | CH$_3$ | 3-Cl(Ph) | |
| 2.171 | iso-C$_3$H$_7$ | CH$_3$ | 4-Cl(Ph) | |
| 2.172 | n-C$_4$H$_9$ | CH$_3$ | 4-Br(Ph) | |
| 2.173 | iso-C$_4$H$_9$ | CH$_3$ | 4-F(Ph) | |
| 2.174 | c-C$_3$H$_5$ | CH$_3$ | 4-OCH$_3$(Ph) | |
| 2.175 | 1-CH$_3$-c-C$_3$H$_5$ | CH$_3$ | 4-CH$_3$(Ph) | |
| 2.176 | C(H)=N—OCH$_3$ | CH$_3$ | 4-NO$_2$(Ph) | |
| 2.177 | C(CH$_3$)=N—OCH$_3$ | CH$_3$ | 2,4-Cl(Ph) | |
| 2.178 | C(C$_2$H$_5$)=N—OCH$_3$ | CH$_3$ | 2,4-F(Ph) | |
| 2.179 | Ph | CH$_3$ | Ph | |
| 2.180 | Ph | CH$_3$ | 2-Cl(Ph) | |
| 2.181 | Ph | CH$_3$ | 3-Cl(Ph) | |
| 2.182 | Ph | CH$_3$ | 4-Cl(Ph) | |
| 2.183 | 4-Cl(Ph) | CH$_3$ | Ph | |
| 2.184 | 4-Cl(Ph) | CH$_3$ | 4-Cl(Ph) | |
| 2.185 | 4-F(Ph) | CH$_3$ | Ph | |
| 2.186 | 4-F(Ph) | CH$_3$ | 4-F(Ph) | |
| 2.187 | 4-CF$_3$(Ph) | CH$_3$ | Ph | |
| 2.188 | 4-CF$_3$(Ph) | CH$_3$ | 4-CF$_3$(Ph) | |
| 2.189 | 2,4-Cl(Ph) | CH$_3$ | Ph | |
| 2.190 | 2,4-Cl(Ph) | CH$_3$ | 2,4-Cl(Ph) | |
| 2.191 | 2,4-F(Ph) | CH$_3$ | Ph | |
| 2.192 | CH$_3$ | H | 1-napthyl | |
| 2.193 | C$_2$H$_5$ | H | 1-napthyl | |
| 2.194 | n-C$_3$H$_7$ | H | 1-napthyl | |
| 2.195 | iso-C$_3$H$_7$ | H | 1-napthyl | |
| 2.196 | n-C$_4$H$_9$ | H | 1-napthyl | |
| 2.197 | iso-C$_4$H$_9$ | H | 1-napthyl | |
| 2.198 | c-C$_3$H$_5$ | H | 1-napthyl | |
| 2.199 | 1-CH$_3$-c-C$_3$H$_5$ | H | 1-napthyl | |
| 2.200 | C(H)=N—OCH$_3$ | H | 1-napthyl | |
| 2.201 | C(CH$_3$)=N-OCH$_3$ | H | 1-napthyl | |
| 2.202 | C(C$_2$H$_5$)=N—OCH$_3$ | H | 1-napthyl | |
| 2.203 | Ph | H | 1-napthyl | |
| 2.204 | 2-Cl(Ph) | H | 1-napthyl | |
| 2.205 | 3-Cl(Ph) | H | 1-napthyl | |
| 2.206 | 4-Cl(Ph) | H | 1-napthyl | |
| 2.207 | 2-F(Ph) | H | 1-napthyl | |
| 2.208 | 3-F(Ph) | H | 1-napthyl | |
| 2.209 | 4-F(Ph) | H | 1-napthyl | |
| 2.210 | 2-CF$_3$(Ph) | H | 1-napthyl | |
| 2.211 | 3-CF$_3$(Ph) | H | 1-napthyl | |
| 2.212 | 4-CF$_3$(Ph) | H | 1-napthyl | |
| 2.213 | 2,4-Cl(Ph) | H | 1-napthyl | |
| 2.214 | 2,4-Cl(Ph) | H | 1-napthyl | |
| 2.215 | 2,4-F(Ph) | H | 1-napthyl | |
| 2.216 | CH$_3$ | CH$_3$ | 1-napthyl | |
| 2.217 | C$_2$H$_5$ | CH$_3$ | 1-napthyl | |
| 2.218 | n-C$_3$H$_7$ | CH$_3$ | 1-napthyl | |
| 2.219 | iso-C$_3$H$_7$ | CH$_3$ | 1-napthyl | |
| 2.220 | n-C$_4$H$_9$ | CH$_3$ | 1-napthyl | |
| 2.221 | iso-C$_4$H$_9$ | CH$_3$ | 1-napthyl | |
| 2.222 | c-C$_3$H$_5$ | CH$_3$ | 1-napthyl | |
| 2.223 | 1-CH$_3$-c-C$_3$H$_5$ | CH$_3$ | 1-napthyl | |
| 2.224 | C(H)=N—OCH$_3$ | CH$_3$ | 1-napthyl | |
| 2.225 | C(CH$_3$)=N—OCH$_3$ | CH$_3$ | 1-napthyl | |
| 2.226 | C(C$_2$H$_5$)=N—OCH$_3$ | CH$_3$ | 1-napthyl | |
| 2.227 | Ph | CH$_3$ | 1-napthyl | |
| 2.228 | 2-Cl(Ph) | CH$_3$ | 1-napthyl | |
| 2.229 | 3-Cl(Ph) | CH$_3$ | 1-napthyl | |
| 2.230 | 4-Cl(Ph) | CH$_3$ | 1-napthyl | |
| 2.231 | 2-F(Ph) | CH$_3$ | 1-napthyl | |
| 2.232 | 3-F(Ph) | CH$_3$ | 1-napthyl | |
| 2.233 | 4-F(Ph) | CH$_3$ | 1-napthyl | |
| 2.234 | 2-CF$_3$(Ph) | CH$_3$ | 1-napthyl | |
| 2.235 | 3-CF$_3$(Ph) | CH$_3$ | 1-napthyl | |
| 2.236 | 4-CF$_3$(Ph) | CH$_3$ | 1-napthyl | |
| 2.237 | 2,4-Cl(Ph) | CH$_3$ | 1-napthyl | |
| 2.238 | 2,4-Cl(Ph) | CH$_3$ | 1-napthyl | |
| 2.239 | 2,4-F(Ph) | CH$_3$ | 1-napthyl | |

Typical compounds encompassed by the present invention of Formula I (where A=R$_4$=R$_5$=R$_6$=H) include those compounds presented in Table 3 of Formula VII (X=N and Z is NH) where R$_2$, R$_3$, and R$_7$ are defined in Table 3.

Formula VII

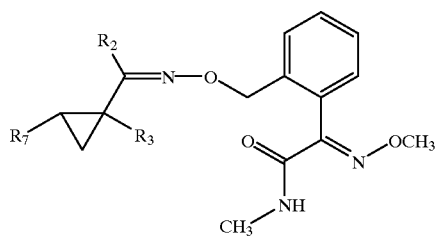

Formula VII

TABLE 3

| Compd | R₂ | R₃ | R₇ | Properties/Comments |
|---|---|---|---|---|
| 3.1A | H | H | Ph | oil, isomer A |
| 3.1B | H | H | Ph | oil, isomer B |
| 3.2 | H | H | 4-Cl(Ph) | |
| 3.3 | H | H | 4-Br(Ph) | |
| 3.4 | H | H | 4-F(Ph) | |
| 3.5 | H | H | 4-OCH₃(Ph) | |
| 3.6 | H | H | 4-CH₃(Ph) | |
| 3.7 | H | H | 4-NO₂(Ph) | |
| 3.8 | H | H | 2,4-Cl(Ph) | |
| 3.9 | H | H | 2,4-F(Ph) | |
| 3.10 | H | H | 3,4-F(Ph) | |
| 3.11 | CH₃ | H | Ph | oil |
| 3.11A | CH₃ | H | Ph | oil, isomer A |
| 3.11B | CH₃ | H | Ph | oil, isomer B |
| 3.12A | CH₃ | H | 2-Cl(Ph) | oil, isomer A |
| 3.12B | CH₃ | H | 2-Cl(Ph) | oil, isomer B |
| 3.13A | CH₃ | H | 3-Cl(Ph) | oil, isomer A |
| 3.13B | CH₃ | H | 3-Cl(Ph) | oil, isomer B |
| 3.14B | CH₃ | H | 4-Cl(Ph) | oil, isomer B |
| 3.14A | CH₃ | H | 4-Cl(Ph) | oil, isomer A |
| 3.15 | CH₃ | H | 2-Br(Ph) | |
| 3.16 | CH₃ | H | 3-Br(Ph) | |
| 3.17 | CH₃ | H | 4-Br(Ph) | |
| 3.18 | CH₃ | H | 2-F(Ph) | |
| 3.19 | CH₃ | H | 3-F(Ph) | oil |
| 3.20A | CH₃ | H | 4-F(Ph) | oil, isomer A |
| 3.20B | CH₃ | H | 4-F(Ph) | oil, isomer B |
| 3.21A | CH₃ | H | 2-OCH₃(Ph) | oil, isomer A |
| 3.21B | CH₃ | H | 2-OCH₃(Ph) | oil, isomer B |
| 3.22A | CH₃ | H | 3-OCH₃(Ph) | oil, isomer A |
| 3.22B | CH₃ | H | 3-OCH₃(Ph) | oil, isomer B |
| 3.23A | CH₃ | H | 4-OCH₃(Ph) | oil, isomer A |
| 3.23B | CH₃ | H | 4-OCH₃(Ph) | oil, isomer B |
| 3.24A | CH₃ | H | 2-CH₃(Ph) | oil, isomer A |
| 3.24B | CH₃ | H | 2-CH₃(Ph) | oil, isomer B |
| 3.25A | CH₃ | H | 3-CH₃(Ph) | oil, isomer A |
| 3.25B | CH₃ | H | 3-CH₃(Ph) | oil, isomer B |
| 3.26A | CH₃ | H | 4-CH₃(Ph) | oil, isomer A |
| 3.26B | CH₃ | H | 4-CH₃(Ph) | oil, isomer B |
| 3.27 | CH₃ | H | 2-CF₃(Ph) | oil |
| 3.28A | CH₃ | H | 3-CF₃(Ph) | oil, isomer A |
| 3.28B | CH₃ | H | 3-CF₃(Ph) | oil, isomer B |
| 3.29 | CH₃ | H | 4-CF₃(Ph) | |
| 3.30 | CH₃ | H | 2-NO₂(Ph) | |
| 3.31 | CH₃ | H | 3-NO₂(Ph) | |
| 3.32 | CH₃ | H | 4-NO₂(Ph) | |
| 3.33B | CH₃ | H | 2,3-Cl(Ph) | oil, isomer B |
| 3.33A | CH₃ | H | 2,3-Cl(Ph) | oil, isomer A |
| 3.34A | CH₃ | H | 2,4-Cl(Ph) | oil, isomer A |
| 3.34B | CH₃ | H | 2,4-Cl(Ph) | oil, isomer B |
| 3.35 | CH₃ | H | 2,5-Cl(Ph) | |
| 3.36 | CH₃ | H | 2,6-Cl(Ph) | |
| 3.37 | CH₃ | H | 3,4-Cl(Ph) | |
| 3.37A | CH₃ | H | 3,4-Cl(Ph) | oil, isomer A |
| 3.37B | CH₃ | H | 3,4-Cl(Ph) | oil, isomer B |
| 3.38 | CH₃ | H | 3,5-Cl(Ph) | |
| 3.39 | CH₃ | H | 2,3-F(Ph) | |
| 3.40 | CH₃ | H | 2,4-F(Ph) | |
| 3.41 | CH₃ | H | 2,5-F(Ph) | |
| 3.42 | CH₃ | H | 2,6-F(Ph) | |
| 3.43 | CH₃ | H | 3,4-F(Ph) | |
| 3.44 | CH₃ | H | 3,5-F(Ph) | |
| 3.45 | C₂H₅ | H | Ph | |
| 3.46 | C₂H₅ | H | 2-Cl(Ph) | |
| 3.47 | C₂H₅ | H | 3-Cl(Ph) | |
| 3.48 | C₂H₅ | H | 4-Cl(Ph) | |
| 3.49 | C₂H₅ | H | 4-Br(Ph) | |
| 3.50 | C₂H₅ | H | 4-F(Ph) | |
| 3.51 | C₂H₅ | H | 4-OCH₃(Ph) | |
| 3.52 | C₂H₅ | H | 4-CH₃(Ph) | |
| 3.53 | C₂H₅ | H | 4-NO₂(Ph) | |
| 3.54 | C₂H₅ | H | 2,4-Cl(Ph) | |
| 3.55 | C₂H₅ | H | 2,4-F(Ph) | |
| 3.56 | n-C₃H₇ | H | Ph | |
| 3.57 | n-C₃H₇ | H | 2-Cl(Ph) | |
| 3.58 | n-C₃H₇ | H | 3-Cl(Ph) | |
| 3.59 | n-C₃H₇ | H | 4-Cl(Ph) | |
| 3.60 | n-C₃H₇ | H | 4-Br(Ph) | |
| 3.61 | n-C₃H₇ | H | 4-F(Ph) | |
| 3.62 | n-C₃H₇ | H | 4-OCH₃(Ph) | |
| 3.63 | n-C₃H₇ | H | 4-CH₃(Ph) | |
| 3.64 | n-C₃H₇ | H | 4-NO₂(Ph) | |
| 3.65 | n-C₃H₇ | H | 2,4-Cl(Ph) | |
| 3.66 | n-C₃H₇ | H | 2,4-F(Ph) | |
| 3.67 | iso-C₃H₇ | H | Ph | oil, isomer A |
| 3.68 | iso-C₃H₇ | H | 2-Cl(Ph) | |
| 3.69 | iso-C₃H₇ | H | 3-Cl(Ph) | |
| 3.70 | iso-C₃H₇ | H | 4-Cl(Ph) | |
| 3.71 | iso-C₃H₇ | H | 4-Br(Ph) | |
| 3.72 | iso-C₃H₇ | H | 4-F(Ph) | |
| 3.73 | iso-C₃H₇ | H | 4-OCH₃(Ph) | |
| 3.74 | iso-C₃H₇ | H | 4-CH₃(Ph) | |
| 3.75 | iso-C₃H₇ | H | 4-NO₂(Ph) | |
| 3.76 | iso-C₃H₇ | H | 2,4-Cl(Ph) | |
| 3.77 | iso-C₃H₇ | H | 2,4-F(Ph) | |
| 3.78 | n-C₄H₉ | H | Ph | |
| 3.79 | n-C₄H₉ | H | 2-Cl(Ph) | |
| 3.80 | n-C₄H₉ | H | 3-Cl(Ph) | |
| 3.81 | n-C₄H₉ | H | 4-Cl(Ph) | |
| 3.82 | n-C₄H₉ | H | 4-Br(Ph) | |
| 3.83 | n-C₄H₉ | H | 4-F(Ph) | |
| 3.84 | n-C₄H₉ | H | 4-OCH₃(Ph) | |
| 3.85 | n-C₄H₉ | H | 4-CH₃(Ph) | |
| 3.86 | n-C₄H₉ | H | 4-NO₂(Ph) | |
| 3.87 | n-C₄H₉ | H | 2,4-Cl(Ph) | |
| 3.88 | n-C₄H₉ | H | 2,4-F(Ph) | |
| 3.89 | iso-C₄H₉ | H | Ph | |
| 3.90 | iso-C₄H₉ | H | 2-Cl(Ph) | |
| 3.91 | iso-C₄H₉ | H | 3-Cl(Ph) | |
| 3.92 | iso-C₄H₉ | H | 4-Cl(Ph) | |
| 3.93 | iso-C₄H₉ | H | 4-Br(Ph) | |
| 3.94 | iso-C₄H₉ | H | 4-F(Ph) | |
| 3.95 | iso-C₄H₉ | H | 4-OCH₃(Ph) | |
| 3.96 | iso-C₄H₉ | H | 4-CH₃(Ph) | |
| 3.97 | iso-C₄H₉ | H | 4-NO₂(Ph) | |
| 3.98 | iso-C₄H₉ | H | 2,4-Cl(Ph) | |
| 3.99 | iso-C₄H₉ | H | 2,4-F(Ph) | |
| 3.100 | c-C₃H₅ | H | Ph | |
| 3.101 | c-C₃H₅ | H | 2-Cl(Ph) | |
| 3.102 | c-C₃H₅ | H | 3-Cl(Ph) | |
| 3.103 | c-C₃H₅ | H | 4-Cl(Ph) | |
| 3.104 | c-C₃H₅ | H | 4-Br(Ph) | |
| 3.105 | c-C₃H₅ | H | 4-F(Ph) | |
| 3.106 | c-C₃H₅ | H | 4-OCH₃(Ph) | |
| 3.107 | c-C₃H₅ | H | 4-CH₃(Ph) | |
| 3.108 | c-C₃H₅ | H | 4-NO₂(Ph) | |
| 3.109 | c-C₃H₅ | H | 2,4-Cl(Ph) | |
| 3.110 | c-C₃H₅ | H | 2,4-F(Ph) | |
| 3.111 | 1-CH₃-c-C₃H₅ | H | Ph | |
| 3.112 | 1-CH₃-c-C₃H₅ | H | 2-Cl(Ph) | |
| 3.113 | 1-CH₃-c-C₃H₅ | H | 3-Cl(Ph) | |
| 3.114 | 1-CH₃-c-C₃H₅ | H | 4-Cl(Ph) | |
| 3.115 | 1-CH₃-c-C₃H₅ | H | 4-Br(Ph) | |

TABLE 3-continued

| Compd | $R_2$ | $R_3$ | $R_7$ | Properties/Comments |
|---|---|---|---|---|
| 3.116 | 1-$CH_3$-c-$C_3H_5$ | H | 4-F(Ph) | |
| 3.117 | 1-$CH_3$-c-$C_3H_5$ | H | 4-$OCH_3$(Ph) | |
| 3.118 | 1-$CH_3$-c-$C_3H_5$ | H | 4-$CH_3$(Ph) | |
| 3.119 | 1-$CH_3$-c-$C_3H_5$ | H | 4-$NO_2$(Ph) | |
| 3.120 | 1-$CH_3$-c-$C_3H_5$ | H | 2,4-Cl(Ph) | |
| 3.121 | 1-$CH_3$-c-$C_3H_5$ | H | 2,4-F(Ph) | |
| 3.122 | C(H)=N—$OCH_3$ | H | Ph | |
| 3.123 | C(H)=N—$OCH_3$ | H | 2-Cl(Ph) | |
| 3.124 | C(H)=N—$OCH_3$ | H | 3-Cl(Ph) | |
| 3.125 | C(H)=N—$OCH_3$ | H | 4-Cl(Ph) | |
| 3.126 | C(H)=N—$OCH_3$ | H | 4-Br(Ph) | |
| 3.127 | C(H)=N—$OCH_3$ | H | 4-F(Ph) | |
| 3.128 | C(H)=N—$OCH_3$ | H | 4-$OCH_3$(Ph) | |
| 3.129 | C(H)=N—$OCH_3$ | H | 4-$CH_3$(Ph) | |
| 3.130 | C(H)=N—$OCH_3$ | H | 4-$NO_2$(Ph) | |
| 3.131 | C(H)=N—$OCH_3$ | H | 2,4-Cl(Ph) | |
| 3.132 | C(H)=N—$OCH_3$ | H | 2,4-F(Ph) | |
| 3.133 | C($CH_3$)=N—$OCH_3$ | H | Ph | |
| 3.134 | C($CH_3$)=N—$OCH_3$ | H | 2-Cl(Ph) | |
| 3.135 | C($CH_3$)=N—$OCH_3$ | H | 3-Cl(Ph) | |
| 3.136 | C($CH_3$)=N—$OCH_3$ | H | 4-Cl(Ph) | |
| 3.137 | C($CH_3$)=N—$OCH_3$ | H | 4-Br(Ph) | |
| 3.138 | C($CH_3$)=N—$OCH_3$ | H | 4-F(Ph) | |
| 3.139 | C($CH_3$)=N—$OCH_3$ | H | 4-$OCH_3$(Ph) | |
| 3.140 | C($CH_3$)=N—$OCH_3$ | H | 4-$CH_3$(Ph) | |
| 3.141 | C($CH_3$)=N—$OCH_3$ | H | 4-$NO_2$(Ph) | |
| 3.142 | C($CH_3$)=N—$OCH_3$ | H | 2,4-Cl(Ph) | |
| 3.143 | C($CH_3$)=N—$OCH_3$ | H | 2,4-F(Ph) | |
| 3.144 | C($C_2H_5$)=N—$OCH_3$ | H | Ph | oil |
| 3.145 | C($C_2H_5$)=N—$OCH_3$ | H | 2-Cl(Ph) | |
| 3.146 | C($C_2H_5$)=N—$OCH_3$ | H | 3-Cl(Ph) | |
| 3.147 | C($C_2H_5$)=N—$OCH_3$ | H | 4-Cl(Ph) | |
| 3.148 | C($C_2H_5$)=N—$OCH_3$ | H | 4-Br(Ph) | |
| 3.149 | C($C_2H_5$)=N—$OCH_3$ | H | 4-F(Ph) | |
| 3.150 | C($C_2H_5$)=N—$OCH_3$ | H | 4-$OCH_3$(Ph) | |
| 3.151 | C($C_2H_5$)=N—$OCH_3$ | H | 4-$CH_3$(Ph) | |
| 3.152 | C($C_2H_5$)=N—$OCH_3$ | H | 4-$NO_2$(Ph) | |
| 3.153 | C($C_2H_5$)=N—$OCH_3$ | H | 2,4-Cl(Ph) | |
| 3.154 | C($C_2H_5$)=N—$OCH_3$ | H | 2,4-F(Ph) | |
| 3.155 | Ph | H | Ph | |
| 3.156 | Ph | H | 2-Cl(Ph) | |
| 3.157 | Ph | H | 3-Cl(Ph) | |
| 3.158 | Ph | H | 4-Cl(Ph) | |
| 3.159 | 4-Cl(Ph) | H | Ph | |
| 3.160 | 4-Cl(Ph) | H | 4-Cl(Ph) | |
| 3.161 | 4-F(Ph) | H | Ph | |
| 3.162 | 4-F(Ph) | H | 4-F(Ph) | |
| 3.163 | 4-$CF_3$(Ph) | H | Ph | |
| 3.164 | 4-$CF_3$(Ph) | H | 4-$CF_3$(Ph) | |
| 3.165 | 2,4-Cl(Ph) | H | Ph | |
| 3.166 | 2,4-Cl(Ph) | H | 2,4-Cl(Ph) | |
| 3.167 | 2,4-F(Ph) | H | Ph | |
| 3.168 | $CH_3$ | H | Ph | |
| 3.169 | $C_2H_5$ | H | 2-Cl(Ph) | |
| 3.170 | n-$C_3H_7$ | H | 3-Cl(Ph) | |
| 3.171 | iso-$C_3H_7$ | H | 4-Cl(Ph) | |
| 3.172 | n-$C_4H_9$ | H | 4-Br(Ph) | |
| 3.173 | iso-$C_4H_9$ | H | 4-F(Ph) | |
| 3.174 | c-$C_3H_5$ | H | 4-$OCH_3$(Ph) | |
| 3.175 | 1-$CH_3$-c-$C_3H_5$ | H | 4-$CH_3$(Ph) | |
| 3.176 | C(H)=N—$OCH_3$ | H | 4-$NO_2$(Ph) | |
| 3.177 | C($CH_3$)=N—$OCH_3$ | H | 2,4-Cl(Ph) | |
| 3.178 | C($C_2H_5$)=N—$OCH_3$ | H | 2,4-F(Ph) | |
| 3.179 | Ph | H | Ph | |
| 3.180 | Ph | H | 2-Cl(Ph) | |
| 3.181 | Ph | H | 3-Cl(Ph) | |
| 3.182 | Ph | H | 4-Cl(Ph) | |
| 3.183 | 4-Cl(Ph) | H | Ph | |
| 3.184 | 4-Cl(Ph) | H | 4-Cl(Ph) | |
| 3.185 | 4-F(Ph) | H | Ph | |
| 3.186 | 4-F(Ph) | H | 4-F(Ph) | |
| 3.187 | 4-$CF_3$(Ph) | H | Ph | |
| 3.188 | 4-$CF_3$(Ph) | H | 4-$CF_3$(Ph) | |
| 3.189 | 2,4-Cl(Ph) | H | Ph | |
| 3.190 | 2,4-Cl(Ph) | H | 2,4-Cl(Ph) | |
| 3.191 | 2,4-F(Ph) | H | Ph | |
| 3.192 | $CH_3$ | H | 1-napthyl | |
| 3.193 | $C_2H_5$ | H | 1-napthyl | |
| 3.194 | n-$C_3H_7$ | H | 1-napthyl | |
| 3.195 | iso-$C_3H_7$ | H | 1-napthyl | |
| 3.196 | n-$C_4H_9$ | H | 1-napthyl | |
| 3.197 | iso-$C_4H_9$ | H | 1-napthyl | |
| 3.198 | c-$C_3H_5$ | H | 1-napthyl | |
| 3.199 | 1-$CH_3$-c-$C_3H_5$ | H | 1-napthyl | |
| 3.200 | C(H)=N—$OCH_3$ | H | 1-napthyl | |
| 3.201 | C($CH_3$)=N—$OCH_3$ | H | 1-napthyl | |
| 3.202 | C($C_2H_5$)=N—$OCH_3$ | H | 1-napthyl | |
| 3.203 | Ph | H | 1-napthyl | |
| 3.204 | 2-Cl(Ph) | H | 1-napthyl | |
| 3.205 | 3-Cl(Ph) | H | 1-napthyl | |
| 3.206 | 4-Cl(Ph) | H | 1-napthyl | |
| 3.207 | 2-F(Ph) | H | 1-napthyl | |
| 3.208 | 3-F(Ph) | H | 1-napthyl | |
| 3.209 | 4-F(Ph) | H | 1-napthyl | |
| 3.210 | 2-$CF_3$(Ph) | H | 1-napthyl | |
| 3.211 | 3-$CF_3$(Ph) | H | 1-napthyl | |
| 3.212 | 4-$CF_3$(Ph) | H | 1-napthyl | |
| 3.213 | 2,4-Cl(Ph) | H | 1-napthyl | |
| 3.214 | 2,4-Cl(Ph) | H | 1-napthyl | |
| 3.215 | 2,4-F(Ph) | H | 1-napthyl | |
| 3.216 | $CH_3$ | H | 1-napthyl | |
| 3.217 | $C_2H_5$ | H | 1-napthyl | |
| 3.218 | n-$C_3H_7$ | H | 1-napthyl | |
| 3.219 | iso-$C_3H_7$ | H | 1-napthyl | |
| 3.220 | n-$C_4H_9$ | H | 1-napthyl | |
| 3.221 | iso-$C_4H_9$ | H | 1-napthyl | |
| 3.222 | c-$C_3H_5$ | H | 1-napthyl | |
| 3.223 | 1-$CH_3$-c-$C_3H_3$ | H | 1-napthyl | |
| 3.224 | C(H)=N—$OCH_3$ | H | 1-napthyl | |
| 3.225 | C($CH_3$)=N—$OCH_3$ | H | 1-napthyl | |
| 3.226 | C($C_2H_5$)=N—$OCH_3$ | H | 1-napthyl | |
| 3.227 | Ph | H | 1-napthyl | |
| 3.228 | 2-Cl(Ph) | H | 1-napthyl | |
| 3.229 | 3-Cl(Ph) | H | 1-napthyl | |
| 3.230 | 4-Cl(Ph) | H | 1-napthyl | |
| 3.231 | 2-F(Ph) | H | 1-napthyl | |
| 3.232 | 3-F(Ph) | H | 1-napthyl | |
| 3.233 | 4-F(Ph) | H | 1-napthyl | |
| 3.234 | 2-$CF_3$(Ph) | H | 1-napthyl | |
| 3.235 | 3-$CF_3$(Ph) | H | 1-napthyl | |
| 3.236 | 4-$CF_3$(Ph) | H | 1-napthyl | |
| 3.237 | 2,4-Cl(Ph) | H | 1-napthyl | |
| 3.238 | 2,4-Cl(Ph) | H | 1-napthyl | |
| 3.239 | 2,4-F(Ph) | H | 1-napthyl | |

Typical compounds encompassed by the present invention of Formula I (where A=$R_4$=$R_5$=$R_6$=H) include those compounds presented in Table 4 of Formula IV (X=CH and Z is O) where $R_2$, $R_3$ and $R_7$ are defined in Table 4.

Formula IV

Formula IV

TABLE 4

| Compd | R$_2$ | R$_3$ | R$_7$ | Properties/Comments |
|---|---|---|---|---|
| 4.1 | H | Ph | Ph | |
| 4.2 | H | Ph | 2-Cl(Ph) | |
| 4.3 | H | Ph | 3-Cl(Ph) | |
| 4.4 | H | Ph | 4-Cl(Ph) | |
| 4.5 | H | Ph | 2-Br(Ph) | |
| 4.6 | H | Ph | 3-Br(Ph) | |
| 4.7 | H | Ph | 4-Br(Ph) | |
| 4.8 | H | Ph | 2-F(Ph) | |
| 4.9 | H | Ph | 3-F(Ph) | |
| 4.10 | H | Ph | 4-F(Ph) | |
| 4.11 | H | Ph | 2-OCH$_3$(Ph) | |
| 4.12 | H | Ph | 3-OCH$_3$(Ph) | |
| 4.13 | H | Ph | 4-OCH$_3$(Ph) | |
| 4.14 | H | Ph | 2-OC$_2$H$_5$(Ph) | |
| 4.15 | H | Ph | 3-OC$_2$H$_5$(Ph) | |
| 4.16 | H | Ph | 4-OC$_2$H$_5$(Ph) | |
| 4.17 | H | Ph | 4-OPh(Ph) | |
| 4.18 | H | Ph | 2-CH$_3$(Ph) | |
| 4.19 | H | Ph | 3-CH$_3$(Ph) | |
| 4.20 | H | Ph | 4-CH$_3$(Ph) | |
| 4.21 | H | Ph | 2-CF$_3$(Ph) | |
| 4.22 | H | Ph | 3-CF$_3$(Ph) | |
| 4.23 | H | Ph | 4-CF$_3$(Ph) | |
| 4.24 | H | Ph | 2-NO$_2$(Ph) | |
| 4.25 | H | Ph | 3-NO$_2$(Ph) | |
| 4.26 | H | Ph | 4-NO$_2$(Ph) | |
| 4.27 | H | Ph | 2,3-Cl(Ph) | |
| 4.28 | H | Ph | 2,4-Cl(Ph) | |
| 4.29 | H | Ph | 2,5-Cl(Ph) | |
| 4.30 | H | Ph | 2,6-Cl(Ph) | |
| 4.31 | H | Ph | 3,4-Cl(Ph) | |
| 4.32 | H | Ph | 3,5-Cl(Ph) | |
| 4.33 | H | Ph | 2,3-F(Ph) | |
| 4.34 | H | Ph | 2,4-F(Ph) | |
| 4.35 | H | Ph | 2,5-F(Ph) | |
| 4.36 | H | Ph | 2,6-F(Ph) | |
| 4.37 | H | Ph | 3,4-F(Ph) | |
| 4.38 | H | Ph | 3,5-FPh | |
| 4.39 | CH$_3$ | Ph | Ph | |
| 4.40 | CH$_3$ | Ph | 2-Cl(Ph) | |
| 4.41 | CH$_3$ | Ph | 3-Cl(Ph) | |
| 4.42 | CH$_3$ | Ph | 4-Cl(Ph) | |
| 4.43 | CH$_3$ | Ph | 2-Br(Ph) | |
| 4.44 | CH$_3$ | Ph | 3-Br(Ph) | |
| 4.45 | CH$_3$ | Ph | 4-Br(Ph) | |
| 4.46 | CH$_3$ | Ph | 2-F(Ph) | |
| 4.47 | CH$_3$ | Ph | 3-F(Ph) | |
| 4.48 | CH$_3$ | Ph | 4-F(Ph) | |
| 4.49 | CH$_3$ | Ph | 2-OCH$_3$(Ph) | |
| 4.50 | CH$_3$ | Ph | 3-OCH$_3$(Ph) | |
| 4.51 | CH$_3$ | Ph | 4-OCH$_3$(Ph) | |
| 4.52 | CH$_3$ | Ph | 2-OC$_2$H$_5$(Ph) | |
| 4.53 | CH$_3$ | Ph | 3-OC$_2$H$_5$(Ph) | |
| 4.54 | CH$_3$ | Ph | 4-OC$_2$H$_5$(Ph) | |
| 4.55 | CH$_3$ | Ph | 4-OPh(Ph) | |
| 4.56 | CH$_3$ | Ph | 2-CH$_3$(Ph) | |
| 4.57 | CH$_3$ | Ph | 3-CH$_3$(Ph) | |
| 4.58 | CH$_3$ | Ph | 4-CH$_3$(Ph) | |
| 4.59 | CH$_3$ | Ph | 2-CF$_3$(Ph) | |
| 4.60 | CH$_3$ | Ph | 3-CF$_3$(Ph) | |
| 4.61 | CH$_3$ | Ph | 4-CF$_3$(Ph) | |
| 4.62 | CH$_3$ | Ph | 4-OCF$_3$(Ph) | |
| 4.63 | CH$_3$ | Ph | 2-NO$_2$(Ph) | |
| 4.64 | CH$_3$ | Ph | 3-NO$_2$(Ph) | |
| 4.65 | CH$_3$ | Ph | 4-NO$_2$(Ph) | |
| 4.66 | CH$_3$ | Ph | 2,3-Cl(Ph) | |
| 4.67 | CH$_3$ | Ph | 2,4-Cl(Ph) | |
| 4.68 | CH$_3$ | Ph | 2,5-Cl(Ph) | |
| 4.69 | CH$_3$ | Ph | 2,6-Cl(Ph) | |
| 4.70 | CH$_3$ | Ph | 3,4-Cl(Ph) | |
| 4.71 | CH$_3$ | Ph | 3,5-Cl(Ph) | |
| 4.72 | CH$_3$ | Ph | 2,3-F(Ph) | |
| 4.73 | CH$_3$ | Ph | 2,4-F(Ph) | |
| 4.74 | CH$_3$ | Ph | 2,5-F(Ph) | |
| 4.75 | CH$_3$ | Ph | 2,6-F(Ph) | |
| 4.76 | CH$_3$ | Ph | 3,4-F(Ph) | |
| 4.77 | CH$_3$ | Ph | 3,5-FPh | |
| 4.78 | C$_2$H$_5$ | Ph | 2-Cl(Ph) | |
| 4.79 | n-C$_3$H$_7$ | Ph | 3-Cl(Ph) | |
| 4.80 | iso-C$_3$H$_7$ | Ph | 4-Cl(Ph) | |
| 4.81 | n-C$_4$H$_9$ | Ph | 4-Br(Ph) | |
| 4.82 | iso-C$_4$H$_9$ | Ph | 4-F(Ph) | |
| 4.83 | c-C$_3$H$_5$ | Ph | 4-OCH$_3$(Ph) | |
| 4.84 | 1-CH$_3$-c-C$_3$H$_5$ | Ph | 4-CH$_3$(Ph) | |
| 4.85 | C(H)=N—OCH$_3$ | Ph | 4-NO$_2$(Ph) | |
| 4.86 | C(CH$_3$)=N—OCH$_3$ | Ph | 2,4-Cl(Ph) | |
| 4.87 | C(C$_2$H$_5$)=N—OCH$_3$ | Ph | 2,4-F(Ph) | |
| 4.88 | Ph | Ph | Ph | |
| 4.89 | Ph | Ph | 2-Cl(Ph) | |
| 4.90 | Ph | Ph | 3-Cl(Ph) | |
| 4.91 | Ph | Ph | 4-Cl(Ph) | |
| 4.92 | 4-Cl(Ph) | Ph | Ph | |
| 4.93 | 4-Cl(Ph) | Ph | 4-Cl(Ph) | |
| 4.94 | 4-F(Ph) | Ph | Ph | |
| 4.95 | 4-F(Ph) | Ph | 4-F(Ph) | |
| 4.96 | 4-CF$_3$(Ph) | Ph | Ph | |
| 4.97 | 4-CF$_3$(Ph) | Ph | 4-CF$_3$(Ph) | |
| 4.98 | 2,4-Cl(Ph) | Ph | Ph | |
| 4.99 | 2,4-Cl(Ph) | Ph | 2,4-Cl(Ph) | |
| 4.100 | 2,4-F(Ph) | Ph | Ph | |
| 4.101 | H | 2-Cl(Ph) | Ph | |
| 4.102 | CH$_3$ | 2-Cl(Ph) | Ph | |
| 4.103 | C$_2$H$_5$ | 2-Cl(Ph) | 2-Cl(Ph) | |
| 4.104 | n-C$_3$H$_7$ | 2-Cl(Ph) | 3-Cl(Ph) | |
| 4.105 | iso-C$_3$H$_7$ | 2-Cl(Ph) | 4-Cl(Ph) | |
| 4.106 | n-C$_4$H$_9$ | 2-Cl(Ph) | 4-Br(Ph) | |
| 4.107 | iso-C$_4$H$_9$ | 2-Cl(Ph) | 4-F(Ph) | |
| 4.108 | c-C$_3$H$_5$ | 2-Cl(Ph) | 4-OCH$_3$(Ph) | |
| 4.109 | 1-CH$_3$-c-C$_3$H$_5$ | 2-Cl(Ph) | 4-CH$_3$(Ph) | |
| 4.110 | C(H)=N—OCH$_3$ | 2-Cl(Ph) | 4-NO$_2$(Ph) | |
| 4.111 | C(CH$_3$)=N—OCH$_3$ | 2-Cl(Ph) | 2,4-Cl(Ph) | |
| 4.112 | C(C$_2$H$_5$)=N—OCH$_3$ | 2-Cl(Ph) | 2,4-F(Ph) | |
| 4.113 | Ph | 2-Cl(Ph) | 2-Cl(Ph) | |
| 4.114 | Ph | 2-Cl(Ph) | 3-Cl(Ph) | |
| 4.115 | Ph | 2-Cl(Ph) | 4-Cl(Ph) | |
| 4.116 | 4-Cl(Ph) | 2-Cl(Ph) | Ph | |
| 4.117 | 4-Cl(Ph) | 2-Cl(Ph) | 4-Cl(Ph) | |
| 4.118 | 4-F(Ph) | 2-Cl(Ph) | Ph | |
| 4.119 | 4-F(Ph) | 2-Cl(Ph) | 4-F(Ph) | |
| 4.120 | 4-CF$_3$(Ph) | 2-Cl(Ph) | Ph | |
| 4.121 | 4-CF$_3$(Ph) | 2-Cl(Ph) | 4-CF$_3$(Ph) | |
| 4.122 | 2,4-Cl(Ph) | 2-Cl(Ph) | Ph | |
| 4.123 | 2,4-Cl(Ph) | 2-Cl(Ph) | 2,4-Cl(Ph) | |
| 4.124 | 2,4-F(Ph) | 2-Cl(Ph) | Ph | |
| 4.125 | H | 4-Cl(Ph) | Ph | |
| 4.126 | CH$_3$ | 4-Cl(Ph) | Ph | |
| 4.127 | C$_2$H$_5$ | 4-Cl(Ph) | 2-Cl(Ph) | |
| 4.128 | n-C$_3$H$_7$ | 4-Cl(Ph) | 3-Cl(Ph) | |
| 4.129 | iso-C$_3$H$_7$ | 4-Cl(Ph) | 4-Cl(Ph) | |
| 4.130 | n-C$_4$H$_9$ | 4-Cl(Ph) | 4-Br(Ph) | |
| 4.131 | iso-C$_4$H$_9$ | 4-Cl(Ph) | 4-F(Ph) | |
| 4.132 | c-C$_3$H$_5$ | 4-Cl(Ph) | 4-OCH$_3$(Ph) | |
| 4.133 | 1-CH$_3$-c-C$_3$H$_5$ | 4-Cl(Ph) | 4-CH$_3$(Ph) | |
| 4.134 | C(H)=N—OCH$_3$ | 4-Cl(Ph) | 4-NO$_2$(Ph) | |
| 4.135 | C(CH$_3$)=N—OCH$_3$ | 4-Cl(Ph) | 2,4-Cl(Ph) | |
| 4.136 | C(C$_2$H$_5$)=N—OCH$_3$ | 4-Cl(Ph) | 2,4-F(Ph) | |
| 4.137 | Ph | 4-Cl(Ph) | 2-Cl(Ph) | |
| 4.138 | Ph | 4-Cl(Ph) | 3-Cl(Ph) | |
| 4.139 | Ph | 4-Cl(Ph) | 4-Cl(Ph) | |
| 4.140 | 4-Cl(Ph) | 4-Cl(Ph) | Ph | |
| 4.141 | 4-Cl(Ph) | 4-Cl(Ph) | 4-Cl(Ph) | |
| 4.142 | 4-F(Ph) | 4-Cl(Ph) | Ph | |
| 4.143 | 4-F(Ph) | 4-Cl(Ph) | 4-F(Ph) | |
| 4.144 | 4-CF$_3$(Ph) | 4-Cl(Ph) | Ph | |
| 4.145 | 4-CF$_3$(Ph) | 4-Cl(Ph) | 4-CF$_3$(Ph) | |
| 4.146 | 2,4-Cl(Ph) | 4-Cl(Ph) | Ph | |
| 4.147 | 2,4-Cl(Ph) | 4-Cl(Ph) | 2,4-Cl(Ph) | |
| 4.148 | 2,4-F(Ph) | 4-Cl(Ph) | Ph | |
| 4.149 | H | 4-CF$_3$(Ph) | Ph | |
| 4.150 | CH$_3$ | 4-CF$_3$(Ph) | Ph | |

TABLE 4-continued

| Compd | R₂ | R₃ | R₇ | Properties/Comments |
|---|---|---|---|---|
| 4.151 | C₂H₅ | 4-CF₃(Ph) | 2-Cl(Ph) | |
| 4.152 | n-C₃H₇ | 4-CF₃(Ph) | 3-Cl(Ph) | |
| 4.153 | iso-C₃H₇ | 4-CF₃(Ph) | 4-Cl(Ph) | |
| 4.154 | n-C₄H₉ | 4-CF₃(Ph) | 4-Br(Ph) | |
| 4.155 | iso-C₄H₉ | 4-CF₃(Ph) | 4-F(Ph) | |
| 4.156 | c-C₃H₅ | 4-CF₃(Ph) | 4-OCH₃(Ph) | |
| 4.157 | 1-CH₃-c-C₃H₅ | 4-CF₃(Ph) | 4-CH₃(Ph) | |
| 4.158 | C(H)=N—OCH₃ | 4-CF₃(Ph) | 4-NO₂(Ph) | |
| 4.159 | C(CH₃)=N—OCH₃ | 4-CF₃(Ph) | 2,4-Cl(Ph) | |
| 4.160 | C(C₂H₅)=N—OCH₃ | 4-CF₃(Ph) | 2,4-F(Ph) | |
| 4.161 | Ph | 4-CF₃(Ph) | 2-Cl(Ph) | |
| 4.162 | Ph | 4-CF₃(Ph) | 3-Cl(Ph) | |
| 4.163 | Ph | 4-CF₃(Ph) | 4-Cl(Ph) | |
| 4.164 | 4-Cl(Ph) | 4-CF₃(Ph) | Ph | |
| 4.165 | 4-Cl(Ph) | 4-CF₃(Ph) | 4-Cl(Ph) | |
| 4.166 | 4-F(Ph) | 4-CF₃(Ph) | Ph | |
| 4.167 | 4-F(Ph) | 4-CF₃(Ph) | 4-F(Ph) | |
| 4.168 | 4-CF₃(Ph) | 4-CF₃(Ph) | Ph | |
| 4.169 | 4-CF₃(Ph) | 4-CF₃(Ph) | 4-CF₃(Ph) | |
| 4.170 | 2,4-Cl(Ph) | 4-CF₃(Ph) | Ph | |
| 4.171 | 2,4-Cl(Ph) | 4-CF₃(Ph) | 2,4-Cl(Ph) | |
| 4.172 | 2,4-F(Ph) | 4-CF₃(Ph) | Ph | |
| 4.173 | H | 1-napthyl | Ph | |
| 4.174 | CH₃ | 1-napthyl | Ph | |
| 4.175 | C₂H₅ | 1-napthyl | 2-Cl(Ph) | |
| 4.176 | n-C₃H₇ | 1-napthyl | 3-Cl(Ph) | |
| 4.177 | iso-C₃H₇ | 1-napthyl | 4-Cl(Ph) | |
| 4.178 | n-C₄H₉ | 1-napthyl | 4-Br(Ph) | |
| 4.179 | iso-C₄H₉ | 1-napthyl | 4-F(Ph) | |
| 4.180 | c-C₃H₅ | 1-napthyl | 4-OCH₃(Ph) | |
| 4.181 | 1-CH₃-c-C₃H₅ | 1-napthyl | 4-CH₃(Ph) | |
| 4.182 | C(H)=N—OCH₃ | 1-napthyl | 4-NO₂(Ph) | |
| 4.183 | C(CH₃)=N—OCH₃ | 1-napthyl | 2,4-Cl(Ph) | |
| 4.184 | C(C₂H₅)=N—OCH₃ | 1-napthyl | 2,4-F(Ph) | |
| 4.185 | Ph | 1-napthyl | 2-Cl(Ph) | |
| 4.186 | Ph | 1-napthyl | 3-Cl(Ph) | |
| 4.187 | Ph | 1-napthyl | 4-Cl(Ph) | |
| 4.188 | 4-Cl(Ph) | 1-napthyl | Ph | |
| 4.189 | 4-Cl(Ph) | 1-napthyl | 4-Cl(Ph) | |
| 4.190 | 4-F(Ph) | 1-napthyl | Ph | |
| 4.191 | 4-F(Ph) | 1-napthyl | 4-F(Ph) | |
| 4.192 | 4-CF₃(Ph) | 1-napthyl | Ph | |
| 4.193 | 4-CF₃(Ph) | 1-napthyl | 4-CF₃(Ph) | |
| 4.194 | 2,4-Cl(Ph) | 1-napthyl | Ph | |
| 4.195 | 2,4-Cl(Ph) | 1-napthyl | 2,4-Cl(Ph) | |
| 4.196 | 2,4-F(Ph) | 1-napthyl | Ph | |

Table 5:

Compounds 5.1 to 5.196 are compounds of Formula V (X=N and Z=O) wherein the substituents R₂, R₃, and R₇ are defined in Table 4.

Table 6:

Compounds 6.1 to 6.196 are compounds of Formula VII (X=N and Z=NH) wherein the substituents R₂, R₃, and R₇ are defined in Table 4.

Typical compounds encompassed by the present invention of Formula I (where A=R₄=R₅=R₆=H) include those compounds presented in Table 4 of Formula IV (X=CH and Z is O) where R₂, R₃ and R₇ are defined in Table 7.

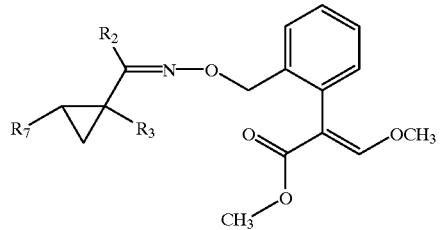

Formula IV

TABLE 7

| Compd | R₂ | R₃ | R₇ | Properties/Comments |
|---|---|---|---|---|
| 7.1 | H | 2-furyl | Ph | |
| 7.2 | H | 2-furyl | 2-Cl(Ph) | |
| 7.3 | H | 2-furyl | 3-Cl(Ph) | |
| 7.4 | H | 2-furyl | 4-Cl(Ph) | |
| 7.5 | H | 2-furyl | 4-Br(Ph) | |
| 7.6 | H | 2-furyl | 4-F(Ph) | |
| 7.7 | H | 2-furyl | 4-OCH₃(Ph) | |
| 7.8 | H | 2-furyl | 4-CH₃(Ph) | |
| 7.9 | H | 2-furyl | 4-NO₂(Ph) | |
| 7.10 | H | 2-furyl | 2,4-Cl(Ph) | |
| 7.11 | H | 2-furyl | 2,4-F(Ph) | |
| 7.12 | H | 2-thienyl | Ph | |
| 7.13 | H | 2-thienyl | 2-Cl(Ph) | |
| 7.14 | H | 2-thienyl | 3-Cl(Ph) | |
| 7.15 | H | 2-thienyl | 4-Cl(Ph) | |
| 7.16 | H | 2-thienyl | 4-Br(Ph) | |
| 7.17 | H | 2-thienyl | 4-F(Ph) | |
| 7.18 | H | 2-thienyl | 4-OCH₃(Ph) | |
| 7.19 | H | 2-thienyl | 4-CH₃(Ph) | |
| 7.20 | H | 2-thienyl | 4-NO₂(Ph) | |
| 7.21 | H | 2-thienyl | 2,4-Cl(Ph) | |
| 7.22 | H | 2-thienyl | 2,4-F(Ph) | |
| 7.23 | H | 2-pyridyl | Ph | |
| 7.24 | H | 2-pyridyl | 2-Cl(Ph) | |
| 7.25 | H | 2-pyridyl | 3-Cl(Ph) | |
| 7.26 | H | 2-pyridyl | 4-Cl(Ph) | |
| 7.27 | H | 2-pyridyl | 4-Br(Ph) | |
| 7.28 | H | 2-pyridyl | 4-F(Ph) | |
| 7.29 | H | 2-pyridyl | 4-OCH₃(Ph) | |
| 7.30 | H | 2-pyridyl | 4-CH₃(Ph) | |
| 7.31 | H | 2-pyridyl | 4-NO₂(Ph) | |
| 7.32 | H | 2-pyridyl | 2,4-Cl(Ph) | |
| 7.33 | H | 2-pyridyl | 2,4-F(Ph) | |
| 7.34 | H | 3-pyridyl | Ph | |
| 7.35 | H | 3-pyridyl | 2-Cl(Ph) | |
| 7.36 | H | 3-pyridyl | 3-Cl(Ph) | |
| 7.37 | H | 3-pyridyl | 4-Cl(Ph) | |
| 7.38 | H | 3-pyridyl | 4-Br(Ph) | |
| 7.39 | H | 3-pyridyl | 4-F(Ph) | |
| 7.40 | H | 3-pyridyl | 4-OCH₃(Ph) | |
| 7.41 | H | 3-pyridyl | 4-CH₃(Ph) | |
| 7.42 | H | 3-pyridyl | 4-NO₂(Ph) | |
| 7.43 | H | 3-pyridyl | 2,4-Cl(Ph) | |
| 7.44 | H | 3-pyridyl | 2,4-F(Ph) | |
| 7.45 | H | 4-pyridyl | Ph | |
| 7.46 | H | 4-pyridyl | 2-Cl(Ph) | |
| 7.47 | H | 4-pyridyl | 3-Cl(Ph) | |
| 7.48 | H | 4-pyridyl | 4-Cl(Ph) | |
| 7.49 | H | 4-pyridyl | 4-Br(Ph) | |
| 7.50 | H | 4-pyridyl | 4-F(Ph) | |
| 7.51 | H | 4-pyridyl | 4-OCH₃(Ph) | |
| 7.52 | H | 4-pyridyl | 4-CH₃(Ph) | |
| 7.53 | H | 4-pyridyl | 4-NO₂(Ph) | |
| 7.54 | H | 4-pyridyl | 2,4-Cl(Ph) | |
| 7.55 | H | 4-pyridyl | 2,4-F(Ph) | |
| 7.56 | H | 4-pyridyl | 2-Cl(Ph) | |
| 7.57 | H | 4-pyridyl | 3-Cl(Ph) | |

TABLE 7-continued

| Compd | $R_2$ | $R_3$ | $R_7$ | Properties/Comments |
|---|---|---|---|---|
| 7.58 | H | 4-pyridyl | 4-Cl(Ph) | |
| 7.59 | H | 4-pyridyl | 4-Br(Ph) | |
| 7.60 | H | 4-pyridyl | 4-F(Ph) | |
| 7.61 | H | 4-pyridyl | 4-OCH$_3$(Ph) | |
| 7.62 | H | 4-pyridyl | 4-CH$_3$(Ph) | |
| 7.63 | H | 4-pyridyl | 4-NO$_2$(Ph) | |
| 7.64 | H | 4-pyridyl | 2,4-Cl(Ph) | |
| 7.65 | H | 4-pyridyl | 2,4-F(Ph) | |
| 7.66 | CH$_3$ | 3-furyl | Ph | |
| 7.67 | CH$_3$ | 3-furyl | 2-Cl(Ph) | |
| 7.68 | CH$_3$ | 3-furyl | 3-Cl(Ph) | |
| 7.69 | CH$_3$ | 3-furyl | 4-Cl(Ph) | |
| 7.70 | CH$_3$ | 3-furyl | 4-Br(Ph) | |
| 7.71 | CH$_3$ | 3-furyl | 4-F(Ph) | |
| 7.72 | CH$_3$ | 3-furyl | 4-OCH$_3$(Ph) | |
| 7.73 | CH$_3$ | 3-furyl | 4-CH$_3$(Ph) | |
| 7.74 | CH$_3$ | 3-furyl | 4-NO$_2$(Ph) | |
| 7.75 | CH$_3$ | 3-furyl | 2,4-Cl(Ph) | |
| 7.76 | CH$_3$ | 3-furyl | 2,4-F(Ph) | |
| 7.77 | CH$_3$ | 3-thienyl | Ph | |
| 7.78 | CH$_3$ | 3-thienyl | 2-Cl(Ph) | |
| 7.79 | CH$_3$ | 3-thienyl | 3-Cl(Ph) | |
| 7.80 | CH$_3$ | 3-thienyl | 4-Cl(Ph) | |
| 7.81 | CH$_3$ | 3-thienyl | 4-Br(Ph) | |
| 7.82 | CH$_3$ | 3-thienyl | 4-F(Ph) | |
| 7.83 | CH$_3$ | 3-thienyl | 4-OCH$_3$(Ph) | |
| 7.84 | CH$_3$ | 3-thienyl | 4-CH$_3$(Ph) | |
| 7.85 | CH$_3$ | 3-thienyl | 4-NO$_2$(Ph) | |
| 7.86 | CH$_3$ | 3-thienyl | 2,4-Cl(Ph) | |
| 7.87 | CH$_3$ | 3-thienyl | 2,4-F(Ph) | |
| 7.88 | CH$_3$ | 2-pyridyl | Ph | |
| 7.89 | CH$_3$ | 2-pyridyl | 2-Cl(Ph) | |
| 7.90 | CH$_3$ | 2-pyridyl | 3-Cl(Ph) | |
| 7.91 | CH$_3$ | 2-pyridyl | 4-Cl(Ph) | |
| 7.92 | CH$_3$ | 2-pyridyl | 4-Br(Ph) | |
| 7.93 | CH$_3$ | 2-pyridyl | 4-F(Ph) | |
| 7.94 | CH$_3$ | 2-pyridyl | 4-OCH$_3$(Ph) | |
| 7.95 | CH$_3$ | 2-pyridyl | 4-CH$_3$(Ph) | |
| 7.96 | CH$_3$ | 2-pyridyl | 4-NO$_2$(Ph) | |
| 7.97 | CH$_3$ | 2-pyridyl | 2,4-Cl(Ph) | |
| 7.98 | CH$_3$ | 2-pyridyl | 2,4-F(Ph) | |
| 7.99 | CH$_3$ | 3-pyridyl | Ph | |
| 7.100 | CH$_3$ | 3-pyridyl | 2-Cl(Ph) | |
| 7.101 | CH$_3$ | 3-pyridyl | 3-Cl(Ph) | |
| 7.102 | CH$_3$ | 3-pyridyl | 4-Cl(Ph) | |
| 7.103 | CH$_3$ | 3-pyridyl | 4-Br(Ph) | |
| 7.104 | CH$_3$ | 3-pyridyl | 4-F(Ph) | |
| 7.105 | CH$_3$ | 3-pyridyl | 4-OCH$_3$(Ph) | |
| 7.106 | CH$_3$ | 3-pyridyl | 4-CH$_3$(Ph) | |
| 7.107 | CH$_3$ | 3-pyridyl | 4-NO$_2$(Ph) | |
| 7.108 | CH$_3$ | 3-pyridyl | 2,4-Cl(Ph) | |
| 7.109 | CH$_3$ | 3-pyridyl | 2,4-F(Ph) | |
| 7.110 | CH$_3$ | 4-pyridyl | Ph | |
| 7.111 | CH$_3$ | 4-pyridyl | 2-Cl(Ph) | |
| 7.112 | CH$_3$ | 4-pyridyl | 3-Cl(Ph) | |
| 7.113 | CH$_3$ | 4-pyridyl | 4-Cl(Ph) | |
| 7.114 | CH$_3$ | 4-pyridyl | 4-Br(Ph) | |
| 7.115 | CH$_3$ | 4-pyridyl | 4-F(Ph) | |
| 7.116 | CH$_3$ | 4-pyridyl | 4-OCH$_3$(Ph) | |
| 7.117 | CH$_3$ | 4-pyridyl | 4-CH$_3$(Ph) | |
| 7.118 | CH$_3$ | 4-pyridyl | 4-NO$_2$(Ph) | |
| 7.119 | CH$_3$ | 4-pyridyl | 2,4-Cl(Ph) | |
| 7.120 | CH$_3$ | 4-pyridyl | 2,4-F(Ph) | |
| 7.121 | CH$_3$ | 4-pyridyl | 2-Cl(Ph) | |
| 7.122 | CH$_3$ | 4-pyridyl | 3-Cl(Ph) | |
| 7.123 | CH$_3$ | 4-pyridyl | 4-Cl(Ph) | |
| 7.124 | CH$_3$ | 4-pyridyl | 4-Br(Ph) | |
| 7.125 | CH$_3$ | 4-pyridyl | 4-F(Ph) | |
| 7.126 | CH$_3$ | 4-pyridyl | 4-OCH$_3$(Ph) | |
| 7.127 | CH$_3$ | 4-pyridyl | 4-CH$_3$(Ph) | |
| 7.128 | CH$_3$ | 4-pyridyl | 4-NO$_2$(Ph) | |
| 7.129 | CH$_3$ | 4-pyridyl | 2,4-Cl(Ph) | |
| 7.130 | CH$_3$ | 4-pyridyl | 2,4-F(Ph) | |
| 7.131 | CH$_3$ | 4-pyridyl | Ph | |
| 7.132 | C$_2$H$_5$ | 2-thienyl | 2-Cl(Ph) | |
| 7.133 | n-C$_3$H$_7$ | 2-thienyl | 3-Cl(Ph) | |
| 7.134 | iso-C$_3$H$_7$ | 2-thienyl | 4-Cl(Ph) | |
| 7.135 | n-C$_4$H$_9$ | 2-thienyl | 4-Br(Ph) | |
| 7.136 | iso-C$_4$H$_9$ | 2-thienyl | 4-F(Ph) | |
| 7.137 | c-C$_3$H$_5$ | 2-thienyl | 4-OCH$_3$(Ph) | |
| 7.138 | 1-CH$_3$-c-C$_3$H$_5$ | 2-thienyl | 4-CH$_3$(Ph) | |
| 7.139 | C(H)=N—OCH$_3$ | 2-thienyl | 4-NO$_2$(Ph) | |
| 7.140 | C(CH$_3$)=NOCH$_3$ | 2-thienyl | 2,4-Cl(Ph) | |
| 7.141 | C(C$_2$H$_5$)=NOCH$_3$ | 2-thienyl | 2,4-F(Ph) | |
| 7.142 | Ph | 2-thienyl | 2-Cl(Ph) | |
| 7.143 | Ph | 2-thienyl | 3-Cl(Ph) | |
| 7.144 | Ph | 2-thienyl | 4-Cl(Ph) | |
| 7.145 | 4-Cl(Ph) | 2-thienyl | Ph | |
| 7.146 | 4-Cl(Ph) | 2-thienyl | 4-Cl(Ph) | |
| 7.147 | 4-F(Ph) | 2-thienyl | Ph | |
| 7.148 | 4-F(Ph) | 2-thienyl | 4-F(Ph) | |
| 7.149 | 4-CF$_3$(Ph) | 2-thienyl | Ph | |
| 7.150 | 4-CF$_3$(Ph) | 2-thienyl | 4-CF$_3$(Ph) | |
| 7.151 | 2,4-Cl(Ph) | 2-thienyl | Ph | |
| 7.152 | 2,4-Cl(Ph) | 2-thienyl | 2,4-Cl(Ph) | |
| 7.153 | 2,4-F(Ph) | 2-thienyl | Ph | |
| 7.154 | C$_2$H$_5$ | 2-pyridyl | 2-Cl(Ph) | |
| 7.155 | n-C$_3$H$_7$ | 2-pyridyl | 3-Cl(Ph) | |
| 7.156 | iso-C$_3$H$_7$ | 2-pyridyl | 4-Cl(Ph) | |
| 7.157 | n-C$_4$H$_9$ | 2-pyridyl | 4-Br(Ph) | |
| 7.158 | iso-C$_4$H$_9$ | 2-pyridyl | 4-F(Ph) | |
| 7.159 | c-C$_3$H$_5$ | 2-pyridyl | 4-OCH$_3$(Ph) | |
| 7.160 | 1-CH$_3$-c-C$_3$H$_5$ | 2-pyridyl | 4-CH$_3$(Ph) | |
| 7.161 | C(H)=NOCH$_3$ | 2-pyridyl | 4-NO$_2$(Ph) | |
| 7.162 | C(CH$_3$)=NOCH$_3$ | 2-pyridyl | 2,4-Cl(Ph) | |
| 7.163 | C(C$_2$H$_5$)=NOCH$_3$ | 2-pyridyl | 2,4-F(Ph) | |
| 7.164 | Ph | 2-pyridyl | 2-Cl(Ph) | |
| 7.165 | Ph | 2-pyridyl | 3-Cl(Ph) | |
| 7.166 | Ph | 2-pyridyl | 4-Cl(Ph) | |
| 7.167 | 4-Cl(Ph) | 2-pyridyl | Ph | |
| 7.168 | 4-Cl(Ph) | 2-pyridyl | 4-Cl(Ph) | |
| 7.169 | 4-F(Ph) | 2-pyridyl | Ph | |
| 7.170 | 4-F(Ph) | 2-pyridyl | 4-F(Ph) | |
| 7.171 | 4-CF$_3$(Ph) | 2-pyridyl | Ph | |
| 7.172 | 4-CF$_3$(Ph) | 2-pyridyl | 4-CF$_3$(Ph) | |
| 7.173 | 2,4-Cl(Ph) | 2-pyridyl | Ph | |
| 7.174 | 2,4-Cl(Ph) | 2-pyridyl | 2,4-Cl(Ph) | |
| 7.175 | 2,4-F(Ph) | 2-pyridyl | Ph | |
| 7.176 | C$_2$H$_5$ | 4-pyridyl | 2-Cl(Ph) | |
| 7.177 | n-C$_3$H$_7$ | 4-pyridyl | 3-Cl(Ph) | |
| 7.178 | iso-C$_3$H$_7$ | 4-pyridyl | 4-Cl(Ph) | |
| 7.179 | n-C$_4$H$_9$ | 4-pyridyl | 4-Br(Ph) | |
| 7.180 | iso-C$_4$H$_9$ | 4-pyridyl | 4-F(Ph) | |
| 7.181 | c-C$_3$H$_5$ | 4-pyridyl | 4-OCH$_3$(Ph) | |
| 7.182 | 1-CH$_3$-c-C$_3$H$_5$ | 4-pyridyl | 4-CH$_3$(Ph) | |
| 7.183 | C(H)=NOCH$_3$ | 4-pyridyl | 4-NO$_2$(Ph) | |
| 7.184 | C(CH$_3$)=NOCH$_3$ | 4-pyridyl | 2,4-Cl(Ph) | |
| 7.185 | C(C$_2$H$_5$)=NOCH$_3$ | 4-pyridyl | 2,4-F(Ph) | |
| 7.186 | Ph | 4-pyridyl | 2-Cl(Ph) | |
| 7.187 | Ph | 4-pyridyl | 3-Cl(Ph) | |
| 7.188 | Ph | 4-pyridyl | 4-Cl(Ph) | |
| 7.189 | 4-Cl(Ph) | 4-pyridyl | Ph | |
| 7.190 | 4-Cl(Ph) | 4-pyridyl | 4-Cl(Ph) | |
| 7.191 | 4-F(Ph) | 4-pyridyl | Ph | |
| 7.192 | 4-F(Ph) | 4-pyridyl | 4-F(Ph) | |
| 7.193 | 4-CF$_3$(Ph) | 4-pyridyl | Ph | |
| 7.194 | 4-CF$_3$(Ph) | 4-pyridyl | 4-CF$_3$(Ph) | |
| 7.195 | 2,4-Cl(Ph) | 4-pyridyl | Ph | |
| 7.196 | 2,4-Cl(Ph) | 4-pyridyl | 2,4-Cl(Ph) | |
| 7.197 | 2,4-F(Ph) | 4-pyridyl | Ph | |

Table 8:
Compounds 8.001 to 8.197 are compounds of Formula V (X=N and Z=O) wherein the substituents $R_2$, $R_3$, and $R_7$ are defined in Table 7.

Table 9:
Compounds 8.001 to 8.197 are compounds of Formula VII (X=N and Z=NH) wherein the substituents $R_2$, $R_3$, and $R_7$ are defined in Table 7.

Typical compounds encompassed by the present invention of Formula I (where A=$R_4$=$R_5$=$R_6$=H) include those compounds presented in Table 10 of Formula IV (X=CH and Z is O) where $R_2$, $R_3$ and $R_7$ are defined in Table 10.

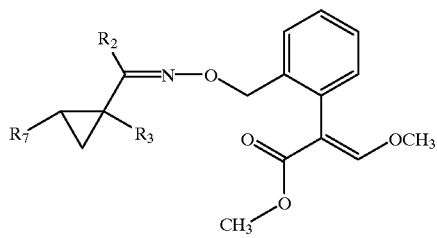

Formula IV

TABLE 10

| Compd | $R_2$ | $R_3$ | $R_7$ | Properties/Comments |
|---|---|---|---|---|
| 10.1 | H | H | 2-furyl | |
| 10.2 | $CH_3$ | H | 2-furyl | |
| 10.3 | $C_2H_5$ | H | 2-furyl | |
| 10.4 | n-$C_3H_7$ | H | 2-furyl | |
| 10.5 | iso-$C_3H_7$ | H | 2-furyl | |
| 10.6 | n-$C_4H_9$ | H | 2-furyl | |
| 10.7 | iso-$C_4H_9$ | H | 2-furyl | |
| 10.8 | c-$C_3H_5$ | H | 2-furyl | |
| 10.9 | 1-$CH_3$-c-$C_3H_5$ | H | 2-furyl | |
| 10.10 | C(H)=N—$OCH_3$ | H | 2-furyl | |
| 10.11 | C($CH_3$)=N—$OCH_3$ | H | 2-furyl | |
| 10.12 | C($C_2H_5$)=N—$OCH_3$ | H | 2-furyl | |
| 10.13 | Ph | H | 2-furyl | |
| 10.14 | 2-Cl(Ph) | H | 2-furyl | |
| 10.15 | 3-Cl(Ph) | H | 2-furyl | |
| 10.16 | 4-Cl(Ph) | H | 2-furyl | |
| 10.17 | 2-F(Ph) | H | 2-furyl | |
| 10.18 | 3-F(Ph) | H | 2-furyl | |
| 10.19 | 4-F(Ph) | H | 2-furyl | |
| 10.20 | 2-$CF_3$(Ph) | H | 2-furyl | |
| 10.21 | 3-$CF_3$(Ph) | H | 2-furyl | |
| 10.22 | 4-$CF_3$(Ph) | H | 2-furyl | |
| 10.23 | 2,4-Cl(Ph) | H | 2-furyl | |
| 10.24 | 2,4-F(Ph) | H | 2-furyl | |
| 10.25 | H | H | 3-furyl | |
| 10.26 | $CH_3$ | H | 3-furyl | |
| 10.27 | $C_2H_5$ | H | 3-furyl | |
| 10.28 | n-$C_3H_7$ | H | 3-furyl | |
| 10.29 | iso-$C_3H_7$ | H | 3-furyl | |
| 10.30 | n-$C_4H_9$ | H | 3-furyl | |
| 10.31 | iso-$C_4H_9$ | H | 3-furyl | |
| 10.32 | c-$C_3H_5$ | H | 3-furyl | |
| 10.33 | 1-$CH_3$-c-$C_3H_5$ | H | 3-furyl | |
| 10.34 | C(H)=N—$OCH_3$ | H | 3-furyl | |
| 10.35 | C($CH_3$)=N—$OCH_3$ | H | 3-furyl | |
| 10.36 | C($C_2H_5$)=N—$OCH_3$ | H | 3-furyl | |
| 10.37 | Ph | H | 3-furyl | |
| 10.38 | 2-Cl(Ph) | H | 3-furyl | |
| 10.39 | 3-Cl(Ph) | H | 3-furyl | |
| 10.40 | 4-Cl(Ph) | H | 3-furyl | |
| 10.41 | 2-F(Ph) | H | 3-furyl | |
| 10.42 | 3-F(Ph) | H | 3-furyl | |
| 10.43 | 4-F(Ph) | H | 3-furyl | |
| 10.44 | 2-$CF_3$(Ph) | H | 3-furyl | |
| 10.45 | 3-$CF_3$(Ph) | H | 3-furyl | |
| 10.46 | 4-$CF_3$(Ph) | H | 3-furyl | |
| 10.47 | 2,4-Cl(Ph) | H | 3-furyl | |
| 10.48 | 2,4-F(Ph) | H | 3-furyl | |
| 10.49 | H | H | 2-thienyl | |
| 10.50 | $CH_3$ | H | 2-thienyl | |
| 10.51 | $C_2H_5$ | H | 2-thienyl | |
| 10.52 | n-$C_3H_7$ | H | 2-thienyl | |
| 10.53 | iso-$C_3H_7$ | H | 2-thienyl | |
| 10.54 | n-$C_4H_9$ | H | 2-thienyl | |
| 10.55 | iso-$C_4H_9$ | H | 2-thienyl | |

TABLE 10-continued

| Compd | $R_2$ | $R_3$ | $R_7$ | Properties/Comments |
|---|---|---|---|---|
| 10.56 | c-$C_3H_5$ | H | 2-thienyl | |
| 10.57 | 1-$CH_3$-c-$C_3H_5$ | H | 2-thienyl | |
| 10.58 | C(H)=N—$OCH_3$ | H | 2-thienyl | |
| 10.59 | C($CH_3$)=N—$OCH_3$ | H | 2-thienyl | |
| 10.60 | C($C_2H_5$)=N—$OCH_3$ | H | 2-thienyl | |
| 10.61 | Ph | H | 2-thienyl | |
| 10.62 | 2-Cl(Ph) | H | 2-thienyl | |
| 10.63 | 3-Cl(Ph) | H | 2-thienyl | |
| 10.64 | 4-Cl(Ph) | H | 2-thienyl | |
| 10.65 | 2-F(Ph) | H | 2-thienyl | |
| 10.66 | 3-F(Ph) | H | 2-thienyl | |
| 10.67 | 4-F(Ph) | H | 2-thienyl | |
| 10.68 | 2-$CF_3$(Ph) | H | 2-thienyl | |
| 10.69 | 3-$CF_3$(Ph) | H | 2-thienyl | |
| 10.70 | 4-$CF_3$(Ph) | H | 2-thienyl | |
| 10.71 | 2,4-Cl(Ph) | H | 2-thienyl | |
| 10.72 | 2,4-F(Ph) | H | 2-thienyl | |
| 10.73 | H | H | 3-thienyl | |
| 10.74 | $CH_3$ | H | 3-thienyl | |
| 10.75 | $C_2H_5$ | H | 3-thienyl | |
| 10.76 | n-$C_3H_7$ | H | 3-thienyl | |
| 10.77 | iso-$C_3H_7$ | H | 3-thienyl | |
| 10.78 | n-$C_4H_9$ | H | 3-thienyl | |
| 10.79 | iso-$C_4H_9$ | H | 3-thienyl | |
| 10.80 | c-$C_3H_5$ | H | 3-thienyl | |
| 10.81 | 1-$CH_3$-c-$C_3H_5$ | H | 3-thienyl | |
| 10.82 | C(H)=N—$OCH_3$ | H | 3-thienyl | |
| 10.83 | C($CH_3$)=N—$OCH_3$ | H | 3-thienyl | |
| 10.84 | C($C_2H_5$)=N—$OCH_3$ | H | 3-thienyl | |
| 10.85 | Ph | H | 3-thienyl | |
| 10.86 | 2-Cl(Ph) | H | 3-thienyl | |
| 10.87 | 3-Cl(Ph) | H | 3-thienyl | |
| 10.88 | 4-Cl(Ph) | H | 3-thienyl | |
| 10.89 | 2-F(Ph) | H | 3-thienyl | |
| 10.90 | 3-F(Ph) | H | 3-thienyl | |
| 10.91 | 4-F(Ph) | H | 3-thienyl | |
| 10.92 | 2-$CF_3$(Ph) | H | 3-thienyl | |
| 10.93 | 3-$CF_3$(Ph) | H | 3-thienyl | |
| 10.94 | 4-$CF_3$(Ph) | H | 3-thienyl | |
| 10.95 | 2,4-Cl(Ph) | H | 3-thienyl | |
| 10.96 | 2,4-F(Ph) | H | 3-thienyl | |
| 10.97 | H | H | 2-pyridyl | |
| 10.98 | $CH_3$ | H | 2-pyridyl | |
| 10.99 | $C_2H_5$ | H | 2-pyridyl | |
| 10.100 | n-$C_3H_7$ | H | 2-pyridyl | |
| 10.101 | iso-$C_3H_7$ | H | 2-pyridyl | |
| 10.102 | n-$C_4H_9$ | H | 2-pyridyl | |
| 10.103 | iso-$C_4H_9$ | H | 2-pyridyl | |
| 10.104 | c-$C_3H_5$ | H | 2-pyridyl | |
| 10.105 | 1-$CH_3$-c-$C_3H_5$ | H | 2-pyridyl | |
| 10.106 | C(H)=N—$OCH_3$ | H | 2-pyridyl | |
| 10.107 | C($CH_3$)=N—$OCH_3$ | H | 2-pyridyl | |
| 10.108 | C($C_2H_5$)=N—$OCH_3$ | H | 2-pyridyl | |
| 10.109 | Ph | H | 2-pyridyl | |
| 10.110 | 2-Cl(Ph) | H | 2-pyridyl | |
| 10.111 | 3-Cl(Ph) | H | 2-pyridyl | |
| 10.112 | 4-Cl(Ph) | H | 2-pyridyl | |
| 10.113 | 2-F(Ph) | H | 2-pyridyl | |
| 10.114 | 3-F(Ph) | H | 2-pyridyl | |
| 10.115 | 4-F(Ph) | H | 2-pyridyl | |
| 10.116 | 2-$CF_3$(Ph) | H | 2-pyridyl | |
| 10.117 | 3-$CF_3$(Ph) | H | 2-pyridyl | |
| 10.118 | 4-$CF_3$(Ph) | H | 2-pyridyl | |
| 10.119 | 2,4-Cl(Ph) | H | 2-pyridyl | |
| 10.120 | 2,4-F(Ph) | H | 2-pyridyl | |
| 10.121 | H | H | 3-pyridyl | |
| 10.122 | $CH_3$ | H | 3-pyridyl | |
| 10.123 | $C_2H_5$ | H | 3-pyridyl | |
| 10.124 | n-$C_3H_7$ | H | 3-pyridyl | |
| 10.125 | iso-$C_3H_7$ | H | 3-pyridyl | |
| 10.126 | n-$C_4H_9$ | H | 3-pyridyl | |
| 10.127 | iso-$C_4H_9$ | H | 3-pyridyl | |
| 10.128 | c-$C_3H_5$ | H | 3-pyridyl | |
| 10.129 | 1-$CH_3$-c-$C_3H_5$ | H | 3-pyridyl | |
| 10.130 | C(H)=N—$OCH_3$ | H | 3-pyridyl | |
| 10.131 | C($CH_3$)=N—$OCH_3$ | H | 3-pyridyl | |

TABLE 10-continued

| Compd | R$_2$ | R$_3$ | R$_7$ | Properties/Comments |
|---|---|---|---|---|
| 10.132 | C(C$_2$H$_5$)=N—OCH$_3$ | H | 3-pyridyl | |
| 10.133 | Ph | H | 3-pyridyl | |
| 10.134 | 2-Cl(Ph) | H | 3-pyridyl | |
| 10.135 | 3-Cl(Ph) | H | 3-pyridyl | |
| 10.136 | 4-Cl(Ph) | H | 3-pyridyl | |
| 10.137 | 2-F(Ph) | H | 3-pyridyl | |
| 10.138 | 3-F(Ph) | H | 3-pyridyl | |
| 10.139 | 4-F(Ph) | H | 3-pyridyl | |
| 10.140 | 2-CF$_3$(Ph) | H | 3-pyridyl | |
| 10.141 | 3-CF$_3$(Ph) | H | 3-pyridyl | |
| 10.142 | 4-CF$_3$(Ph) | H | 3-pyridyl | |
| 10.143 | 2,4-Cl(Ph) | H | 3-pyridyl | |
| 10.144 | 2,4-F(Ph) | H | 3-pyridyl | |
| 10.145 | H | H | 4-pyridyl | |
| 10.146 | CH$_3$ | H | 4-pyridyl | |
| 10.147 | C$_2$H$_5$ | H | 4-pyridyl | |
| 10.148 | n-C$_3$H$_7$ | H | 4-pyridyl | |
| 10.149 | iso-C$_3$H$_7$ | H | 4-pyridyl | |
| 10.150 | n-C$_4$H$_9$ | H | 4-pyridyl | |
| 10.151 | iso-C$_4$H$_9$ | H | 4-pyridyl | |
| 10.152 | c-C$_3$H$_5$ | H | 4-pyridyl | |
| 10.153 | 1-CH$_3$-c-C$_3$H$_5$ | H | 4-pyridyl | |
| 10.154 | C(H)=N—OCH$_3$ | H | 4-pyridyl | |
| 10.155 | C(CH$_3$)=N—OCH$_3$ | H | 4-pyridyl | |
| 10.156 | C(C$_2$H$_5$)=N—OCH$_3$ | H | 4-pyridyl | |
| 10.157 | Ph | H | 4-pyridyl | |
| 10.158 | 2-Cl(Ph) | H | 4-pyridyl | |
| 10.159 | 3-Cl(Ph) | H | 4-pyridyl | |
| 10.160 | 4-Cl(Ph) | H | 4-pyridyl | |
| 10.161 | 2-F(Ph) | H | 4-pyridyl | |
| 10.162 | 3-F(Ph) | H | 4-pyridyl | |
| 10.163 | 4-F(Ph) | H | 4-pyridyl | |
| 10.164 | 2-CF$_3$(Ph) | H | 4-pyridyl | |
| 10.165 | 3-CF$_3$(Ph) | H | 4-pyridyl | |
| 10.166 | 4-CF$_3$(Ph) | H | 4-pyridyl | |
| 10.167 | 2,4-Cl(Ph) | H | 4-pyridyl | |
| 10.168 | 2,4-F(Ph) | H | 4-pyridyl | |
| 10.169 | H | H | pyrazinyl | |
| 10.170 | CH$_3$ | H | pyrazinyl | |
| 10.171 | C$_2$H$_5$ | H | pyrazinyl | |
| 10.172 | n-C$_3$H$_7$ | H | pyrazinyl | |
| 10.173 | iso-C$_3$H$_7$ | H | pyrazinyl | |
| 10.174 | n-C$_4$H$_9$ | H | pyrazinyl | |
| 10.175 | iso-C$_4$H$_9$ | H | pyrazinyl | |
| 10.176 | c-C$_3$H$_5$ | H | pyrazinyl | |
| 10.177 | H | H | quinolin-4-yl | |
| 10.178 | CH$_3$ | H | quinolin-4-yl | |
| 10.179 | C$_2$H$_5$ | H | quinolin-4-yl | |
| 10.180 | n-C$_3$H$_7$ | H | quinolin-4-yl | |
| 10.181 | iso-C$_3$H$_7$ | H | quinolin-4-yl | |
| 10.182 | n-C$_4$H$_9$ | H | quinolin-4-yl | |
| 10.183 | iso-C$_4$H$_9$ | H | quinolin-4-yl | |
| 10.184 | c-C$_3$H$_5$ | H | quinolin-4-yl | |
| 10.185 | H | CH$_3$ | 2-furyl | |
| 10.186 | CH$_3$ | CH$_3$ | 2-furyl | |
| 10.187 | C$_2$H$_5$ | CH$_3$ | 2-furyl | |
| 10.188 | n-C$_3$H$_7$ | CH$_3$ | 2-furyl | |
| 10.189 | iso-C$_3$H$_7$ | CH$_3$ | 2-furyl | |
| 10.190 | n-C$_4$H$_9$ | CH$_3$ | 2-furyl | |
| 10.191 | iso-C$_4$H$_9$ | CH$_3$ | 2-furyl | |
| 10.192 | c-C$_3$H$_5$ | CH$_3$ | 2-furyl | |
| 10.193 | H | CH$_3$ | 3-furyl | |
| 10.194 | CH$_3$ | CH$_3$ | 3-furyl | |
| 10.195 | C$_2$H$_5$ | CH$_3$ | 3-furyl | |
| 10.196 | n-C$_3$H$_7$ | CH$_3$ | 3-furyl | |
| 10.197 | iso-C$_3$H$_7$ | CH$_3$ | 3-furyl | |
| 10.198 | n-C$_4$H$_9$ | CH$_3$ | 3-furyl | |
| 10.199 | iso-C$_4$H$_9$ | CH$_3$ | 3-furyl | |
| 10.200 | c-C$_3$H$_5$ | CH$_3$ | 3-furyl | |
| 10.201 | H | CH$_3$ | 2-thienyl | |
| 10.202 | CH$_3$ | CH$_3$ | 2-thienyl | |
| 10.203 | C$_2$H$_5$ | CH$_3$ | 2-thienyl | |
| 10.204 | n-C$_3$H$_7$ | CH$_3$ | 2-thienyl | |
| 10.205 | iso-C$_3$H$_7$ | CH$_3$ | 2-thienyl | |
| 10.206 | n-C$_4$H$_9$ | CH$_3$ | 2-thienyl | |
| 10.207 | iso-C$_4$H$_9$ | CH$_3$ | 2-thienyl | |
| 10.208 | c-C$_3$H$_5$ | CH$_3$ | 2-thienyl | |
| 10.209 | H | CH$_3$ | 3-thienyl | |
| 10.210 | CH$_3$ | CH$_3$ | 3-thienyl | |
| 10.211 | C$_2$H$_5$ | CH$_3$ | 3-thienyl | |
| 10.212 | n-C$_3$H$_7$ | CH$_3$ | 3-thienyl | |
| 10.213 | iso-C$_3$H$_7$ | CH$_3$ | 3-thienyl | |
| 10.214 | n-C$_4$H$_9$ | CH$_3$ | 3-thienyl | |
| 10.215 | iso-C$_4$H$_9$ | CH$_3$ | 3-thienyl | |
| 10.216 | c-C$_3$H$_5$ | CH$_3$ | 3-thienyl | |
| 10.217 | H | CH$_3$ | 2-pyridyl | |
| 10.218 | CH$_3$ | CH$_3$ | 2-pyridyl | |
| 10.219 | C$_2$H$_5$ | CH$_3$ | 2-pyridyl | |
| 10.220 | n-C$_3$H$_7$ | CH$_3$ | 2-pyridyl | |
| 10.221 | iso-C$_3$H$_7$ | CH$_3$ | 2-pyridyl | |
| 10.222 | n-C$_4$H$_9$ | CH$_3$ | 2-pyridyl | |
| 10.223 | iso-C$_4$H$_9$ | CH$_3$ | 2-pyridyl | |
| 10.224 | c-C3H5 | CH$_3$ | 2-pyridyl | |
| 10.225 | H | CH$_3$ | 3-pyridyl | |
| 10.226 | CH$_3$ | CH$_3$ | 3-pyridyl | |
| 10.227 | C$_2$H$_5$ | CH$_3$ | 3-pyridyl | |
| 10.228 | n-C$_3$H$_7$ | CH$_3$ | 3-pyridyl | |
| 10.229 | iso-C$_3$H$_7$ | CH$_3$ | 3-pyridyl | |
| 10.230 | n-C$_4$H$_9$ | CH$_3$ | 3-pyridyl | |
| 10.231 | iso-C$_4$H$_9$ | CH$_3$ | 3-pyridyl | |
| 10.232 | c-C$_3$H$_5$ | CH$_3$ | 3-pyridyl | |
| 10.233 | H | CH$_3$ | 4-pyridyl | |
| 10.234 | CH$_3$ | CH$_3$ | 4-pyridyl | |
| 10.235 | C$_2$H$_5$ | CH$_3$ | 4-pyridyl | |
| 10.236 | n-C$_3$H$_7$ | CH$_3$ | 4-pyridyl | |
| 10.237 | iso-C$_3$H$_7$ | CH$_3$ | 4-pyridyl | |
| 10.238 | n-C$_4$H$_9$ | CH$_3$ | 4-pyridyl | |
| 10.239 | iso-C$_4$H$_9$ | CH$_3$ | 4-pyridyl | |
| 10.240 | c-C$_3$H$_5$ | CH$_3$ | 4-pyridyl | |

Typical compounds encompassed by the present invention of Formula I (where A=R$_4$=R$_5$=R$_6$=H) include those compounds presented in Table 11 of Formula V (X=N and Z is O) where R$_2$, R$_3$, and R$_7$ are defined in Table 11.

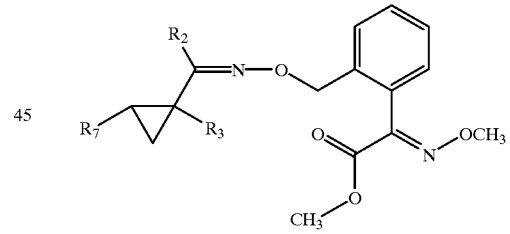

Formula V

TABLE 11

| Compd | R$_2$ | R$_3$ | R$_7$ | Properties/Comments |
|---|---|---|---|---|
| 11.1 | H | H | 2-furyl | |
| 11.2A | CH$_3$ | H | 2-furyl | oil, isomer A |
| 11.2B | CH$_3$ | H | 2-furyl | oil, isomer B |
| 11.3 | C$_2$H$_5$ | H | 2-furyl | |
| 11.4 | n-C$_3$H$_7$ | H | 2-furyl | |
| 11.5 | iso-C$_3$H$_7$ | H | 2-furyl | |
| 11.6 | n-C$_4$H$_9$ | H | 2-furyl | |
| 11.7 | iso-C$_4$H$_9$ | H | 2-furyl | |
| 11.8 | c-C$_3$H$_5$ | H | 2-furyl | |
| 11.9 | 1-CH$_3$-c-C$_3$H$_5$ | H | 2-furyl | |

TABLE 11-continued

| Compd | R$_2$ | R$_3$ | R$_7$ | Properties/Comments |
|---|---|---|---|---|
| 11.10 | C(H)=N—OCH$_3$ | H | 2-furyl | |
| 11.11 | C(CH$_3$)=NOCH$_3$ | H | 2-furyl | |
| 11.12 | C(C$_2$H$_5$)=NOCH$_3$ | H | 2-furyl | |
| 11.13 | Ph | H | 2-furyl | |
| 11.14 | 2-Cl(Ph) | H | 2-furyl | |
| 11.15 | 3-Cl(Ph) | H | 2-furyl | |
| 11.16 | 4-Cl(Ph) | H | 2-furyl | |
| 11.17 | 2-F(Ph) | H | 2-furyl | |
| 11.18 | 3-F(Ph) | H | 2-furyl | |
| 11.19 | 4-F(Ph) | H | 2-furyl | |
| 11.20 | 2-CF$_3$(Ph) | H | 2-furyl | |
| 11.21 | 3-CF$_3$(Ph) | H | 2-furyl | |
| 11.22 | 4-CF$_3$(Ph) | H | 2-furyl | |
| 11.23 | 2,4-Cl(Ph) | H | 2-furyl | |
| 11.24 | 2,4-F(Ph) | H | 2-furyl | |
| 11.25 | H | H | 3-furyl | |
| 11.26 | CH$_3$ | H | 3-furyl | |
| 11.27 | C$_2$H$_5$ | H | 3-furyl | |
| 11.28 | n-C$_3$H$_7$ | H | 3-furyl | |
| 11.29 | iso-C$_3$H$_7$ | H | 3-furyl | |
| 11.30 | n-C$_4$H$_9$ | H | 3-furyl | |
| 11.31 | iso-C$_4$H$_9$ | H | 3-furyl | |
| 11.32 | c-C$_3$H$_5$ | H | 3-furyl | |
| 11.33 | 1-CH$_3$-c-C$_3$H$_5$ | H | 3-furyl | |
| 11.34 | C(H)=N—OCH$_3$ | H | 3-furyl | |
| 11.35 | C(CH$_3$)=NOCH$_3$ | H | 3-furyl | |
| 11.36 | C(C$_2$H$_5$)=NOCH$_3$ | H | 3-furyl | |
| 11.37 | Ph | H | 3-furyl | |
| 11.38 | 2-Cl(Ph) | H | 3-furyl | |
| 11.39 | 3-Cl(Ph) | H | 3-furyl | |
| 11.40 | 4-Cl(Ph) | H | 3-furyl | |
| 11.41 | 2-F(Ph) | H | 3-furyl | |
| 11.42 | 3-F(Ph) | H | 3-furyl | |
| 11.43 | 4-F(Ph) | H | 3-furyl | |
| 11.44 | 2-CF$_3$(Ph) | H | 3-furyl | |
| 11.45 | 3-CF$_3$(Ph) | H | 3-furyl | |
| 11.46 | 4-CF$_3$(Ph) | H | 3-furyl | |
| 11.47 | 2,4-Cl(Ph) | H | 3-furyl | |
| 11.48 | 2,4-F(Ph) | H | 3-furyl | |
| 11.49 | H | H | 2-thienyl | |
| 11.50A | CH$_3$ | H | 2-thienyl | oil, isomer A |
| 11.50B | CH$_3$ | H | 2-thienyl | oil, isomer B |
| 11.51 | C$_2$H$_5$ | H | 2-thienyl | |
| 11.52 | n-C$_3$H$_7$ | H | 2-thienyl | |
| 11.53 | iso-C$_3$H$_7$ | H | 2-thienyl | |
| 11.54 | n-C$_4$H$_9$ | H | 2-thienyl | |
| 11.55 | iso-C$_4$H$_9$ | H | 2-thienyl | |
| 11.56 | c-C$_3$H$_5$ | H | 2-thienyl | |
| 11.57 | 1-CH$_3$-c-C$_3$H$_5$ | H | 2-thienyl | |
| 11.58 | C(H)=N—OCH$_3$ | H | 2-thienyl | |
| 11.59 | C(CH$_3$)=NOCH$_3$ | H | 2-thienyl | |
| 11.60 | C(C$_2$H$_5$)=NOCH$_3$ | H | 2-thienyl | |
| 11.61 | Ph | H | 2-thienyl | |
| 11.62 | 2-Cl(Ph) | H | 2-thienyl | |
| 11.63 | 3-Cl(Ph) | H | 2-thienyl | |
| 11.64 | 4-Cl(Ph) | H | 2-thienyl | |
| 11.65 | 2-F(Ph) | H | 2-thienyl | |
| 11.66 | 3-F(Ph) | H | 2-thienyl | |
| 11.67 | 4-F(Ph) | H | 2-thienyl | |
| 11.68 | 2-CF$_3$(Ph) | H | 2-thienyl | |
| 11.69 | 3-CF$_3$(Ph) | H | 2-thienyl | |
| 11.70 | 4-CF$_3$(Ph) | H | 2-thienyl | |
| 11.71 | 2,4-Cl(Ph) | H | 2-thienyl | |
| 11.72 | 2,4-F(Ph) | H | 2-thienyl | |
| 11.73 | H | H | 3-thienyl | |
| 11.74 | CH$_3$ | H | 3-thienyl | |
| 11.75 | C$_2$H$_5$ | H | 3-thienyl | |
| 11.76 | n-C$_3$H$_7$ | H | 3-thienyl | |
| 11.77 | iso-C$_3$H$_7$ | H | 3-thienyl | |
| 11.78 | n-C$_4$H$_9$ | H | 3-thienyl | |
| 11.79 | iso-C$_4$H$_9$ | H | 3-thienyl | |
| 11.80 | c-C$_3$H$_5$ | H | 3-thienyl | |
| 11.81 | 1-CH$_3$-c-C$_3$H$_5$ | H | 3-thienyl | |
| 11.82 | C(H)=NOCH$_3$ | H | 3-thienyl | |
| 11.83 | C(CH$_3$)=NOCH$_3$ | H | 3-thienyl | |
| 11.84 | C(C$_2$H$_5$)=NOCH$_3$ | H | 3-thienyl | |
| 11.85 | Ph | H | 3-thienyl | |
| 11.86 | 2-Cl(Ph) | H | 3-thienyl | |
| 11.87 | 3-Cl(Ph) | H | 3-thienyl | |
| 11.88 | 4-Cl(Ph) | H | 3-thienyl | |
| 11.89 | 2-F(Ph) | H | 3-thienyl | |
| 11.90 | 3-F(Ph) | H | 3-thienyl | |
| 11.91 | 4-F(Ph) | H | 3-thienyl | |
| 11.92 | 2-CF$_3$(Ph) | H | 3-thienyl | |
| 11.93 | 3-CF$_3$(Ph) | H | 3-thienyl | |
| 11.94 | 4-CF$_3$(Ph) | H | 3-thienyl | |
| 11.95 | 2,4-Cl(Ph) | H | 3-thienyl | |
| 11.96 | 2,4-F(Ph) | H | 3-thienyl | |
| 11.97 | H | H | 2-pyridyl | |
| 11.98A | CH$_3$ | H | 2-pyridyl | oil, isomer A |
| 11.98B | CH$_3$ | H | 2-pyridyl | oil, isomer B |
| 11.99 | C$_2$H$_5$ | H | 2-pyridyl | |
| 11.100 | n-C$_3$H$_7$ | H | 2-pyridyl | |
| 11.101 | iso-C$_3$H$_7$ | H | 2-pyridyl | |
| 11.102 | n-C$_4$H$_9$ | H | 2-pyridyl | |
| 11.103 | iso-C$_4$H$_9$ | H | 2-pyridyl | |
| 11.104 | c-C$_3$H$_5$ | H | 2-pyridyl | |
| 11.105 | 1-CH$_3$-c-C$_3$H$_5$ | H | 2-pyridyl | |
| 11.106 | C(H)=N—OCH$_3$ | H | 2-pyridyl | |
| 11.107 | C(CH$_3$)=NOCH$_3$ | H | 2-pyridyl | |
| 11.108 | C(C$_2$H$_5$)=NOCH$_3$ | H | 2-pyridyl | |
| 11.109 | Ph | H | 2-pyridyl | |
| 11.110 | 2-Cl(Ph) | H | 2-pyridyl | |
| 11.111 | 3-Cl(Ph) | H | 2-pyridyl | |
| 11.112 | 4-Cl(Ph) | H | 2-pyridyl | |
| 11.113 | 2-F(Ph) | H | 2-pyridyl | |
| 11.114 | 3-F(Ph) | H | 2-pyridyl | |
| 11.115 | 4-F(Ph) | H | 2-pyridyl | |
| 11.116 | 2-CF$_3$(Ph) | H | 2-pyridyl | |
| 11.117 | 3-CF$_3$(Ph) | H | 2-pyridyl | |
| 11.118 | 4-CF$_3$(Ph) | H | 2-pyridyl | |
| 11.119 | 2,4-Cl(Ph) | H | 2-pyridyl | |
| 11.120 | 2,4-F(Ph) | H | 2-pyridyl | |
| 11.121 | H | H | 3-pyridyl | |
| 11.121A | CH$_3$ | H | 3-pyridyl | oil, isomer A |
| 11.121B | CH$_3$ | H | 3-pyridyl | oil, isomer B |
| 11.123 | C$_2$H$_5$ | H | 3-pyridyl | |
| 11.124 | n-C$_3$H$_7$ | H | 3-pyridyl | |
| 11.125 | iso-C$_3$H$_7$ | H | 3-pyridyl | |
| 11.126 | n-C$_4$H$_9$ | H | 3-pyridyl | |
| 11.127 | iso-C$_4$H$_9$ | H | 3-pyridyl | |
| 11.128 | c-C$_3$H$_5$ | H | 3-pyridyl | |
| 11.129 | 1-CH$_3$-c-C$_3$H$_5$ | H | 3-pyridyl | |
| 11.130 | C(H)=N—OCH$_3$ | H | 3-pyridyl | |
| 11.131 | C(CH$_3$)=NOCH$_3$ | H | 3-pyridyl | |
| 11.132 | C(C$_2$H$_5$)=NOCH$_3$ | H | 3-pyridyl | |
| 11.133 | Ph | H | 3-pyridyl | |
| 11.134 | 2-Cl(Ph) | H | 3-pyridyl | |
| 11.135 | 3-Cl(Ph) | H | 3-pyridyl | |
| 11.136 | 4-Cl(Ph) | H | 3-pyridyl | |
| 11.137 | 2-F(Ph) | H | 3-pyridyl | |
| 11.138 | 3-F(Ph) | H | 3-pyridyl | |
| 11.139 | 4-F(Ph) | H | 3-pyridyl | |
| 11.140 | 2-CF$_3$(Ph) | H | 3-pyridyl | |
| 11.141 | 3-CF$_3$(Ph) | H | 3-pyridyl | |
| 11.142 | 4-CF$_3$(Ph) | H | 3-pyridyl | |
| 11.143 | 2,4-Cl(Ph) | H | 3-pyridyl | |
| 11.144 | 2,4-F(Ph) | H | 3-pyridyl | |
| 11.145 | H | H | 4-pyridyl | |
| 11.146 | CH$_3$ | H | 4-pyridyl | |
| 11.147 | C$_2$H$_5$ | H | 4-pyridyl | |
| 11.148 | n-C$_3$H$_7$ | H | 4-pyridyl | |
| 11.149 | iso-C$_3$H$_7$ | H | 4-pyridyl | |
| 11.150 | n-C$_4$H$_9$ | H | 4-pyridyl | |
| 11.151 | iso-C$_4$H$_9$ | H | 4-pyridyl | |
| 11.152 | c-C$_3$H$_5$ | H | 4-pyridyl | |
| 11.153 | 1-CH$_3$-c-C$_3$H$_5$ | H | 4-pyridyl | |
| 11.154 | C(H)=N—OCH$_3$ | H | 4-pyridyl | |
| 11.155 | C(CH$_3$)=NOCH$_3$ | H | 4-pyridyl | |
| 11.156 | C(C$_2$H$_5$)=NOCH$_3$ | H | 4-pyridyl | |
| 11.157 | Ph | H | 4-pyridyl | |
| 11.158 | 2-Cl(Ph) | H | 4-pyridyl | |

TABLE 11-continued

| Compd | R$_2$ | R$_3$ | R$_7$ | Properties/Comments |
|---|---|---|---|---|
| 11.159 | 3-Cl(Ph) | H | 4-pyridyl | |
| 11.160 | 4-Cl(Ph) | H | 4-pyridyl | |
| 11.161 | 2-F(Ph) | H | 4-pyridyl | |
| 11.162 | 3-F(Ph) | H | 4-pyridyl | |
| 11.163 | 4-F(Ph) | H | 4-pyridyl | |
| 11.164 | 2-CF$_3$(Ph) | H | 4-pyridyl | |
| 11.165 | 3-CF$_3$(Ph) | H | 4-pyridyl | |
| 11.166 | 4-CF$_3$(Ph) | H | 4-pyridyl | |
| 11.167 | 2,4-Cl(Ph) | H | 4-pyridyl | |
| 11.168 | 2,4-F(Ph) | H | 4-pyridyl | |
| 11.169 | H | H | pyrazinyl | |
| 11.170 | CH$_3$ | H | pyrazinyl | |
| 11.171 | C$_2$H$_5$ | H | pyrazinyl | |
| 11.172 | n-C$_3$H$_7$ | H | pyrazinyl | |
| 11.173 | iso-C$_3$H$_7$ | H | pyrazinyl | |
| 11.174 | n-C$_4$H$_9$ | H | pyrazinyl | |
| 11.175 | iso-C$_4$H$_9$ | H | pyrazinyl | |
| 11.176 | c-C$_3$H$_5$ | H | pyrazinyl | |
| 11.177 | H | H | quinolin-4-yl | |
| 11.178 | CH$_3$ | H | quinolin-4-yl | |
| 11.179 | C$_2$H$_5$ | H | quinolin-4-yl | |
| 11.180 | n-C$_3$H$_7$ | H | quinolin-4-yl | |
| 11.181 | iso-C$_3$H$_7$ | H | quinolin-4-yl | |
| 11.182 | n-C$_4$H$_9$ | H | quinolin-4-yl | |
| 11.183 | iso-C$_4$H$_9$ | H | quinolin-4-yl | |
| 11.184 | c-C$_3$H$_5$ | H | quinolin-4-yl | |
| 11.185 | H | CH$_3$ | 2-furyl | |
| 11.186 | CH$_3$ | CH$_3$ | 2-furyl | |
| 11.187 | C$_2$H$_5$ | CH$_3$ | 2-furyl | |
| 11.188 | n-C$_3$H$_7$ | CH$_3$ | 2-furyl | |
| 11.189 | iso-C$_3$H$_7$ | CH$_3$ | 2-furyl | |
| 11.190 | n-C$_4$H$_9$ | CH$_3$ | 2-furyl | |
| 11.191 | iso-C$_4$H$_9$ | CH$_3$ | 2-furyl | |
| 11.192 | c-C$_3$H$_5$ | CH$_3$ | 2-furyl | |
| 11.193 | H | CH$_3$ | 3-furyl | |
| 11.194 | CH$_3$ | CH$_3$ | 3-furyl | |
| 11.195 | C$_2$H$_5$ | CH$_3$ | 3-furyl | |
| 11.196 | n-C$_3$H$_7$ | CH$_3$ | 3-furyl | |
| 11.197 | iso-C$_3$H$_7$ | CH$_3$ | 3-furyl | |
| 11.198 | n-C$_4$H$_9$ | CH$_3$ | 3-furyl | |
| 11.199 | iso-C$_4$H$_9$ | CH$_3$ | 3-furyl | |
| 11.200 | c-C3H5 | CH$_3$ | 3-furyl | |
| 11.201 | H | CH$_3$ | 2-thienyl | |
| 11.202 | CH$_3$ | CH$_3$ | 2-thienyl | |
| 11.203 | C$_2$H$_5$ | CH$_3$ | 2-thienyl | |
| 11.204 | n-C$_3$H$_7$ | CH$_3$ | 2-thienyl | |
| 11.205 | iso-C$_3$H$_7$ | CH$_3$ | 2-thienyl | |
| 11.206 | n-C$_4$H$_9$ | CH$_3$ | 2-thienyl | |
| 11.207 | iso-C$_4$H$_9$ | CH$_3$ | 2-thienyl | |
| 11.208 | c-C$_3$H$_5$ | CH$_3$ | 2-thienyl | |
| 11.209 | H | CH$_3$ | 3-thienyl | |
| 11.210 | CH$_3$ | CH$_3$ | 3-thienyl | |
| 11.211 | C$_2$H$_5$ | CH$_3$ | 3-thienyl | |
| 11.212 | n-C$_3$H$_7$ | CH$_3$ | 3-thienyl | |
| 11.213 | iso-C$_3$H$_7$ | CH$_3$ | 3-thienyl | |
| 11.214 | n-C$_4$H$_9$ | CH$_3$ | 3-thienyl | |
| 11.215 | iso-C$_4$H$_9$ | CH$_3$ | 3-thienyl | |
| 11.216 | c-C3H5 | CH$_3$ | 3-thienyl | |
| 11.217 | H | CH$_3$ | 2-pyridyl | |
| 11.218 | CH$_3$ | CH$_3$ | 2-pyridyl | |
| 11.219 | C$_2$H$_5$ | CH$_3$ | 2-pyridyl | |
| 11.220 | n-C$_3$H$_7$ | CH$_3$ | 2-pyridyl | |
| 11.221 | iso-C$_3$H$_7$ | CH$_3$ | 2-pyridyl | |
| 11.222 | n-C$_4$H$_9$ | CH$_3$ | 2-pyridyl | |
| 11.223 | iso-C$_4$H$_9$ | CH$_3$ | 2-pyridyl | |
| 11.224 | c-C$_3$H$_5$ | CH$_3$ | 2-pyridyl | |
| 11.225 | H | CH$_3$ | 3-pyridyl | |
| 11.226 | CH$_3$ | CH$_3$ | 3-pyridyl | |
| 11.227 | C$_2$H$_5$ | CH$_3$ | 3-pyridyl | |
| 11.228 | n-C$_3$H$_7$ | CH$_3$ | 3-pyridyl | |
| 11.229 | iso-C$_3$H$_7$ | CH$_3$ | 3-pyridyl | |
| 11.230 | n-C$_4$H$_9$ | CH$_3$ | 3-pyridyl | |
| 11.231 | iso-C$_4$H$_9$ | CH$_3$ | 3-pyridyl | |
| 11.232 | c-C$_3$H$_5$ | CH$_3$ | 3-pyridyl | |
| 11.233 | H | CH$_3$ | 4-pyridyl | |
| 11.234 | CH$_3$ | CH$_3$ | 4-pyridyl | |
| 11.235 | C$_2$H$_5$ | CH$_3$ | 4-pyridyl | |
| 11.236 | n-C$_3$H$_7$ | CH$_3$ | 4-pyridyl | |
| 11.237 | iso-C$_3$H$_7$ | CH$_3$ | 4-pyridyl | |
| 11.238 | n-C$_4$H$_9$ | CH$_3$ | 4-pyridyl | |
| 11.239 | iso-C$_4$H$_9$ | CH$_3$ | 4-pyridyl | |
| 11.240 | c-C$_3$H$_5$ | CH$_3$ | 4-pyridyl | |

Typical compounds encompassed by the present invention of Formula I (where A=R$_4$=R$_5$=R$_6$=H) include those compounds presented in Table 12 of Formula V (X=N and Z is O) where R$_2$, R$_3$, and R$_7$ are defined in Table 12.

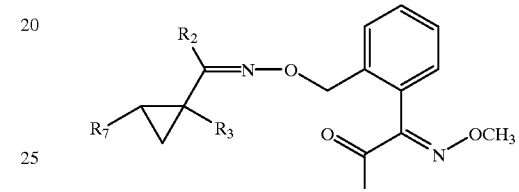

Formula VII

TABLE 12

| Compd | R$_2$ | R$_3$ | R$_7$ | Properties/Comments |
|---|---|---|---|---|
| 12.1 | H | H | 2-furyl | |
| 12.2A | CH$_3$ | H | 2-furyl | oil, isomer A |
| 12.2B | CH$_3$ | H | 2-furyl | oil, isomer B |
| 12.3 | C$_2$H$_5$ | H | 2-furyl | |
| 12.4 | n-C$_3$H$_7$ | H | 2-furyl | |
| 12.5 | iso-C$_3$H$_7$ | H | 2-furyl | |
| 12.6 | n-C$_4$H$_9$ | H | 2-furyl | |
| 12.7 | iso-C$_4$H$_9$ | H | 2-furyl | |
| 12.8 | c-C$_3$H$_5$ | H | 2-furyl | |
| 12.9 | 1-CH$_3$-c-C$_3$H$_5$ | H | 2-furyl | |
| 12.10 | C(H)=N—OCH$_3$ | H | 2-furyl | |
| 12.11 | C(CH$_3$)=N—OCH$_3$ | H | 2-furyl | |
| 12.12 | C(C$_2$H$_5$)=N—OCH$_3$ | H | 2-furyl | |
| 12.13 | Ph | H | 2-furyl | |
| 12.14 | 2-Cl(Ph) | H | 2-furyl | |
| 12.15 | 3-Cl(Ph) | H | 2-furyl | |
| 12.16 | 4-Cl(Ph) | H | 2-furyl | |
| 12.17 | 2-F(Ph) | H | 2-furyl | |
| 12.18 | 3-F(Ph) | H | 2-furyl | |
| 12.19 | 4-F(Ph) | H | 2-furyl | |
| 12.20 | 2-CF$_3$(Ph) | H | 2-furyl | |
| 12.21 | 3-CF$_3$(Ph) | H | 2-furyl | |
| 12.22 | 4-CF$_3$(Ph) | H | 2-furyl | |
| 12.23 | 2,4-Cl(Ph) | H | 2-furyl | |
| 12.24 | 2,4-F(Ph) | H | 2-furyl | |
| 12.25 | H | H | 3-furyl | |
| 12.26 | CH$_3$ | H | 3-furyl | |
| 12.27 | C$_2$H$_5$ | H | 3-furyl | |
| 12.28 | n-C$_3$H$_7$ | H | 3-furyl | |
| 12.29 | iso-C$_3$H$_7$ | H | 3-furyl | |
| 12.30 | n-C$_4$H$_9$ | H | 3-furyl | |
| 12.31 | iso-C$_4$H$_9$ | H | 3-furyl | |
| 12.32 | c-C$_3$H$_5$ | H | 3-furyl | |
| 12.33 | 1-CH$_3$-c-C$_3$H$_5$ | H | 3-furyl | |
| 12.34 | C(H)=N—OCH$_3$ | H | 3-furyl | |
| 12.35 | C(CH$_3$)=N—OCH$_3$ | H | 3-furyl | |
| 12.36 | C(C$_2$H$_5$)=N—OCH$_3$ | H | 3-furyl | |

TABLE 12-continued

| Compd | $R_2$ | $R_3$ | $R_7$ | Properties/Comments |
|---|---|---|---|---|
| 12.37 | Ph | H | 3-furyl | |
| 12.38 | 2-Cl(Ph) | H | 3-furyl | |
| 12.39 | 3-Cl(Ph) | H | 3-furyl | |
| 12.40 | 4-Cl(Ph) | H | 3-furyl | |
| 12.41 | 2-F(Ph) | H | 3-furyl | |
| 12.42 | 3-F(Ph) | H | 3-furyl | |
| 12.43 | 4-F(Ph) | H | 3-furyl | |
| 12.44 | 2-CF$_3$(Ph) | H | 3-furyl | |
| 12.45 | 3-CF$_3$(Ph) | H | 3-furyl | |
| 12.46 | 4-CF$_3$(Ph) | H | 3-furyl | |
| 12.47 | 2,4-Cl(Ph) | H | 3-furyl | |
| 12.48 | 2,4-F(Ph) | H | 3-furyl | |
| 12.49 | H | H | 2-thienyl | |
| 12.50 | CH$_3$ | H | 2-thienyl | |
| 12.50A | CH3 | H | 2-thienyl | oil, isomer A |
| 12.50B | CH3 | H | 2-thienyl | oil, isomer B |
| 12.51 | C$_2$H$_5$ | H | 2-thienyl | |
| 12.52 | n-C$_3$H$_7$ | H | 2-thienyl | |
| 12.53 | iso-C$_3$H$_7$ | H | 2-thienyl | |
| 12.54 | n-C$_4$H$_9$ | H | 2-thienyl | |
| 12.55 | iso-C$_4$H$_9$ | H | 2-thienyl | |
| 12.56 | c-C$_3$H$_5$ | H | 2-thienyl | |
| 12.57 | 1-CH$_3$-c-C$_3$H$_5$ | H | 2-thienyl | |
| 12.58 | C(H)=N—OCH$_3$ | H | 2-thienyl | |
| 12.59 | C(CH$_3$)=N—OCH$_3$ | H | 2-thienyl | |
| 12.60 | C(C$_2$H$_5$)=N—OCH$_3$ | H | 2-thienyl | |
| 12.61 | Ph | H | 2-thienyl | |
| 12.62 | 2-Cl(Ph) | H | 2-thienyl | |
| 12.63 | 3-Cl(Ph) | H | 2-thienyl | |
| 12.64 | 4-Cl(Ph) | H | 2-thienyl | |
| 12.65 | 2-F(Ph) | H | 2-thienyl | |
| 12.66 | 3-F(Ph) | H | 2-thienyl | |
| 12.67 | 4-F(Ph) | H | 2-thienyl | |
| 12.68 | 2-CF$_3$(Ph) | H | 2-thienyl | |
| 12.69 | 3-CF$_3$(Ph) | H | 2-thienyl | |
| 12.70 | 4-CF$_3$(Ph) | H | 2-thienyl | |
| 12.71 | 2,4-Cl(Ph) | H | 2-thienyl | |
| 12.72 | 2,4-F(Ph) | H | 2-thienyl | |
| 12.73 | H | H | 3-thienyl | |
| 12.74 | CH$_3$ | H | 3-thienyl | |
| 12.75 | C$_2$H$_5$ | H | 3-thienyl | |
| 12.76 | n-C$_3$H$_7$ | H | 3-thienyl | |
| 12.77 | iso-C$_3$H$_7$ | H | 3-thienyl | |
| 12.78 | n-C$_4$H$_9$ | H | 3-thienyl | |
| 12.79 | iso-C$_4$H$_9$ | H | 3-thienyl | |
| 12.80 | c-C$_3$H$_5$ | H | 3-thienyl | |
| 12.81 | 1-CH$_3$-c-C$_3$H$_5$ | H | 3-thienyl | |
| 12.82 | C(H)=N—OCH$_3$ | H | 3-thienyl | |
| 12.83 | C(CH$_3$)=N—OCH$_3$ | H | 3-thienyl | |
| 12.84 | C(C$_2$H$_5$)=N—OCH3 | H | 3-thienyl | |
| 12.85 | Ph | H | 3-thienyl | |
| 12.86 | 2-Cl(Ph) | H | 3-thienyl | |
| 12.87 | 3-Cl(Ph) | H | 3-thienyl | |
| 12.88 | 4-Cl(Ph) | H | 3-thienyl | |
| 12.89 | 2-F(Ph) | H | 3-thienyl | |
| 12.90 | 3-F(Ph) | H | 3-thienyl | |
| 12.91 | 4-F(Ph) | H | 3-thienyl | |
| 12.92 | 2-CF$_3$(Ph) | H | 3-thienyl | |
| 12.93 | 3-CF$_3$(Ph) | H | 3-thienyl | |
| 12.94 | 4-CF$_3$(Ph) | H | 3-thienyl | |
| 12.95 | 2,4-Cl(Ph) | H | 3-thienyl | |
| 12.96 | 2,4-F(Ph) | H | 3-thienyl | |
| 12.97 | H | H | 2-pyridyl | |
| 12.98A | CH3 | H | 2-pyridyl | oil, isomer A |
| 12.98B | CH3 | H | 2-pyridyl | oil, isomer B |
| 12.99 | C$_2$H$_5$ | H | 2-pyridyl | |
| 12.100 | n-C$_3$H$_7$ | H | 2-pyridyl | |
| 12.101 | iso-C$_3$H$_7$ | H | 2-pyridyl | |
| 12.102 | n-C$_4$H$_9$ | H | 2-pyridyl | |
| 12.103 | iso-C$_4$H$_9$ | H | 2-pyridyl | |
| 12.104 | c-C$_3$H$_5$ | H | 2-pyridyl | |
| 12.105 | 1-CH$_3$-c-C$_3$H$_5$ | H | 2-pyridyl | |
| 12.106 | C(H)=N—OCH$_3$ | H | 2-pyridyl | |
| 12.107 | C(CH$_3$)=N—OCH$_3$ | H | 2-pyridyl | |
| 12.108 | C(C$_2$H$_5$)=N—OCH3 | H | 2-pyridyl | |
| 12.109 | Ph | H | 2-pyridyl | |
| 12.110 | 2-Cl(Ph) | H | 2-pyridyl | |
| 12.111 | 3-Cl(Ph) | H | 2-pyridyl | |
| 12.112 | 4-Cl(Ph) | H | 2-pyridyl | |
| 12.113 | 2-F(Ph) | H | 2-pyridyl | |
| 12.114 | 3-F(Ph) | H | 2-pyridyl | |
| 12.115 | 4-F(Ph) | H | 2-pyridyl | |
| 12.116 | 2-CF$_3$(Ph) | H | 2-pyridyl | |
| 12.117 | 3-CF$_3$(Ph) | H | 2-pyridyl | |
| 12.118 | 4-CF$_3$(Ph) | H | 2-pyridyl | |
| 12.119 | 2,4-Cl(Ph) | H | 2-pyridyl | |
| 12.120 | 2,4-F(Ph) | H | 2-pyridyl | |
| 12.121 | H | H | 3-pyridyl | |
| 12.122A | CH3 | H | 3-pyridyl | oil, isomer A |
| 12.122B | CH3 | H | 3-pyridyl | oil, isomer B |
| 12.123 | C$_2$H$_5$ | H | 3-pyridyl | |
| 12.124 | n-C$_3$H$_7$ | H | 3-pyridyl | |
| 12.125 | iso-C$_3$H$_7$ | H | 3-pyridyl | |
| 12.126 | n-C$_4$H$_9$ | H | 3-pyridyl | |
| 12.127 | iso-C$_4$H$_9$ | H | 3-pyridyl | |
| 12.128 | c-C$_3$H$_5$ | H | 3-pyridyl | |
| 12.129 | 1-CH$_3$-c-C$_3$H$_5$ | H | 3-pyridyl | |
| 12.130 | C(H)=N—OCH$_3$ | H | 3-pyridyl | |
| 12.131 | C(CH$_3$)=N—OCH$_3$ | H | 3-pyridyl | |
| 12.132 | C(C$_2$H$_5$)=N—OCH$_3$ | H | 3-pyridyl | |
| 12.133 | Ph | H | 3-pyridyl | |
| 12.134 | 2-Cl(Ph) | H | 3-pyridyl | |
| 12.135 | 3-Cl(Ph) | H | 3-pyridyl | |
| 12.136 | 4-Cl(Ph) | H | 3-pyridyl | |
| 12.137 | 2-F(Ph) | H | 3-pyridyl | |
| 12.138 | 3-F(Ph) | H | 3-pyridyl | |
| 12.139 | 4-F(Ph) | H | 3-pyridyl | |
| 12.140 | 2-CF$_3$(Ph) | H | 3-pyridyl | |
| 12.141 | 3-CF$_3$(Ph) | H | 3-pyridyl | |
| 12.142 | 4-CF$_3$(Ph) | H | 3-pyridyl | |
| 12.143 | 2,4-Cl(Ph) | H | 3-pyridyl | |
| 12.144 | 2,4-F(Ph) | H | 3-pyridyl | |
| 12.145 | H | H | 4-pyridyl | |
| 12.146 | CH$_3$ | H | 4-pyridyl | |
| 12.147 | C$_2$H$_5$ | H | 4-pyridyl | |
| 12.148 | n-C$_3$H$_7$ | H | 4-pyridyl | |
| 12.149 | iso-C$_3$H$_7$ | H | 4-pyridyl | |
| 12.150 | n-C$_4$H$_9$ | H | 4-pyridyl | |
| 12.151 | iso-C$_4$H$_9$ | H | 4-pyridyl | |
| 12.152 | c-C$_3$H$_5$ | H | 4-pyridyl | |
| 12.153 | 1-CH$_3$-c-C$_3$H$_5$ | H | 4-pyridyl | |
| 12.154 | C(H)=N—OCH$_3$ | H | 4-pyridyl | |
| 12.155 | C(CH$_3$)=NOCH$_3$ | H | 4-pyridyl | |
| 12.156 | C(C$_2$H$_5$)=NOCH$_3$ | H | 4-pyridyl | |
| 12.157 | Ph | H | 4-pyridyl | |
| 12.158 | 2-Cl(Ph) | H | 4-pyridyl | |
| 12.159 | 3-Cl(Ph) | H | 4-pyridyl | |
| 12.160 | 4-Cl(Ph) | H | 4-pyridyl | |
| 12.161 | 2-F(Ph) | H | 4-pyridyl | |
| 12.162 | 3-F(Ph) | H | 4-pyridyl | |
| 12.163 | 4-F(Ph) | H | 4-pyridyl | |
| 12.164 | 2-CF$_3$(Ph) | H | 4-pyridyl | |
| 12.165 | 3-CF$_3$(Ph) | H | 4-pyridyl | |
| 12.166 | 4-CF$_3$(Ph) | H | 4-pyridyl | |
| 12.167 | 2,4-Cl(Ph) | H | 4-pyridyl | |
| 12.168 | 2,4-F(Ph) | H | 4-pyridyl | |
| 12.169 | H | H | pyrazinyl | |
| 12.170 | CH$_3$ | H | pyrazinyl | |
| 12.171 | C$_2$H$_5$ | H | pyrazinyl | |
| 12.172 | n-C$_3$H$_7$ | H | pyrazinyl | |
| 12.173 | iso-C$_3$H$_7$ | H | pyrazinyl | |
| 12.174 | n-C$_4$H$_9$ | H | pyrazinyl | |
| 12.175 | iso-C$_4$H$_9$ | H | pyrazinyl | |
| 12.176 | c-C$_3$H$_5$ | H | pyrazinyl | |
| 12.177 | H | H | quinolin-4-yl | |
| 12.178 | CH$_3$ | H | quinolin-4-yl | |
| 12.179 | C$_2$H$_5$ | H | quinolin-4-yl | |
| 12.180 | n-C$_3$H$_7$ | H | quinolin-4-yl | |
| 12.181 | iso-C$_3$H$_7$ | H | quinolin-4-yl | |
| 12.182 | n-C$_4$H$_9$ | H | quinolin-4-yl | |
| 12.183 | iso-C$_4$H$_9$ | H | quinolin-4-yl | |
| 12.184 | | H | quinolin-4-yl | |

TABLE 12-continued

| Compd | $R_2$ | $R_3$ | $R_7$ | Properties/Comments |
|---|---|---|---|---|
| 12.185 | H | $CH_3$ | 2-furyl | |
| 12.186 | $CH_3$ | $CH_3$ | 2-furyl | |
| 12.187 | $C_2H_5$ | $CH_3$ | 2-furyl | |
| 12.188 | n-$C_3H_7$ | $CH_3$ | 2-furyl | |
| 12.189 | iso-$C_3H_7$ | $CH_3$ | 2-furyl | |
| 12.190 | n-$C_4H_9$ | $CH_3$ | 2-furyl | |
| 12.191 | iso-$C_4H_9$ | $CH_3$ | 2-furyl | |
| 12.192 | c-$C_3H_5$ | $CH_3$ | 2-furyl | |
| 12.193 | H | $CH_3$ | 3-furyl | |
| 12.194 | $CH_3$ | $CH_3$ | 3-furyl | |
| 12.195 | $C_2H_5$ | $CH_3$ | 3-furyl | |
| 12.196 | n-$C_3H_7$ | $CH_3$ | 3-furyl | |
| 12.197 | iso-$C_3H_7$ | $CH_3$ | 3-furyl | |
| 12.198 | n-$C_4H_9$ | $CH_3$ | 3-furyl | |
| 12.199 | iso-$C_4H_9$ | $CH_3$ | 3-furyl | |
| 12.200 | c-$C_3H_5$ | $CH_3$ | 3-furyl | |
| 12.201 | H | $CH_3$ | 2-thienyl | |
| 12.202 | $CH_3$ | $CH_3$ | 2-thienyl | |
| 12.203 | $C_2H_5$ | $CH_3$ | 2-thienyl | |
| 12.204 | n-$C_3H_7$ | $CH_3$ | 2-thienyl | |
| 12.205 | iso-$C_3H_7$ | $CH_3$ | 2-thienyl | |
| 12.206 | n-$C_4H_9$ | $CH_3$ | 2-thienyl | |
| 12.207 | iso-$C_4H_9$ | $CH_3$ | 2-thienyl | |
| 12.208 | c-$C_3H_5$ | $CH_3$ | 2-thienyl | |
| 12.209 | H | $CH_3$ | 3-thienyl | |
| 12.210 | $CH_3$ | $CH_3$ | 3-thienyl | |
| 12.211 | $C_2H_5$ | $CH_3$ | 3-thienyl | |
| 12.212 | n-$C_3H_7$ | $CH_3$ | 3-thienyl | |
| 12.213 | iso-$C_3H_7$ | $CH_3$ | 3-thienyl | |
| 12.214 | n-$C_4H_9$ | $CH_3$ | 3-thienyl | |
| 12.215 | iso-$C_4H_9$ | $CH_3$ | 3-thienyl | |
| 12.216 | c-$C_3H_5$ | $CH_3$ | 3-thienyl | |
| 12.217 | H | $CH_3$ | 2-pyridyl | |
| 12.218 | $CH_3$ | $CH_3$ | 2-pyridyl | |
| 12.219 | $C_2H_5$ | $CH_3$ | 2-pyridyl | |
| 12.220 | n-$C_3H_7$ | $CH_3$ | 2-pyridyl | |
| 12.221 | iso-$C_3H_7$ | $CH_3$ | 2-pyridyl | |
| 12.222 | n-$C_4H_9$ | $CH_3$ | 2-pyridyl | |
| 12.223 | iso-$C_4H_9$ | $CH_3$ | 2-pyridyl | |
| 12.224 | c-$C_3H_5$ | $CH_3$ | 2-pyridyl | |
| 12.225 | H | $CH_3$ | 3-pyridyl | |
| 12.226 | $CH_3$ | $CH_3$ | 3-pyridyl | |
| 12.227 | $C_2H_5$ | $CH_3$ | 3-pyridyl | |
| 12.228 | n-$C_3H_7$ | $CH_3$ | 3-pyridyl | |
| 12.229 | iso-$C_3H_7$ | $CH_3$ | 3-pyridyl | |
| 12.230 | n-$C_4H_9$ | $CH_3$ | 3-pyridyl | |
| 12.231 | iso-$C_4H_9$ | $CH_3$ | 3-pyridyl | |
| 12.232 | c-$C_3H_5$ | $CH_3$ | 3-pyridyl | |
| 12.233 | H | $CH_3$ | 4-pyridyl | |
| 12.234 | $CH_3$ | $CH_3$ | 4-pyridyl | |
| 12.235 | $C_2H_5$ | $CH_3$ | 4-pyridyl | |
| 12.236 | n-$C_3H_7$ | $CH_3$ | 4-pyridyl | |
| 12.237 | iso-$C_3H_7$ | $CH_3$ | 4-pyridyl | |
| 12.238 | n-$C_4H_9$ | $CH_3$ | 4-pyridyl | |
| 12.239 | iso-$C_4H_9$ | $CH_3$ | 4-pyridyl | |
| 12.240 | c-$C_3H_5$ | $CH_3$ | 4-pyridyl | |

Typical compounds encompassed by the present invention of Formula I (where A=$R_4$=$R_5$=$R_6$=H) include those compounds presented in Table 13 of Formula IV (X=CH and Z is O) where $R_2$, $R_3$ and $R_7$ are defined in Table 13.

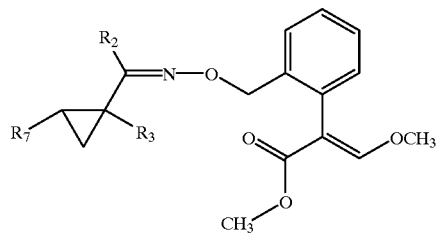

Formula IV

TABLE 13

| Compd | $R_2$ | $R_3$ | $R_7$ | Properties/Comments |
|---|---|---|---|---|
| 13.1 | H | Ph | 2-furyl | |
| 13.2 | H | Ph | 3-furyl | |
| 13.3 | H | Ph | 2-thienyl | |
| 13.4 | H | Ph | 3-thienyl | |
| 13.5 | H | Ph | 2-pyridyl | |
| 13.6 | H | Ph | 3-pyridyl | |
| 13.7 | H | Ph | 4-pyridyl | |
| 13.8 | H | Ph | pyrazinyl | |
| 13.9 | H | Ph | pyrimidin-2-yl | |
| 13.10 | H | Ph | pyrimidin-4-yl | |
| 13.11 | H | Ph | pyrimidin-5-yl | |
| 13.12 | H | Ph | quinolin-2-yl | |
| 13.13 | H | Ph | quinolin-3-yl | |
| 13.14 | H | Ph | quinolin-4-yl | |
| 13.15 | $CH_3$ | Ph | 2-furyl | |
| 13.16 | $CH_3$ | Ph | 3-furyl | |
| 13.17 | $CH_3$ | Ph | 2-thienyl | |
| 13.18 | $CH_3$ | Ph | 3-thienyl | |
| 13.19 | $CH_3$ | Ph | 2-pyridyl | |
| 13.20 | $CH_3$ | Ph | 3-pyridyl | |
| 13.21 | $CH_3$ | Ph | 4-pyridyl | |
| 13.22 | $CH_3$ | Ph | pyrazinyl | |
| 13.23 | $CH_3$ | Ph | pyrimidin-2-yl | |
| 13.24 | $CH_3$ | Ph | pyrimidin-4-yl | |
| 13.25 | $CH_3$ | Ph | pyrimidin-5-yl | |
| 13.26 | $CH_3$ | Ph | quinolin-2-yl | |
| 13.27 | $CH_3$ | Ph | quinolin-3-yl | |
| 13.28 | $CH_3$ | Ph | quinolin-4-yl | |
| 13.29 | $C_2H_5$ | Ph | 2-furyl | |
| 13.30 | $C_2H_5$ | Ph | 3-furyl | |
| 13.31 | $C_2H_5$ | Ph | 2-thienyl | |
| 13.32 | $C_2H_5$ | Ph | 3-thienyl | |
| 13.33 | $C_2H_5$ | Ph | 2-pyridyl | |
| 13.34 | $C_2H_5$ | Ph | 3-pyridyl | |
| 13.35 | $C_2H_5$ | Ph | 4-pyridyl | |
| 13.36 | $C_2H_5$ | Ph | pyrazinyl | |
| 13.37 | $C_2H_5$ | Ph | pyrimidin-2-yl | |
| 13.38 | $C_2H_5$ | Ph | pyrimidin-4-yl | |
| 13.39 | $C_2H_5$ | Ph | pyrimidin-5-yl | |
| 13.40 | $C_2H_5$ | Ph | quinolin-2-yl | |
| 13.41 | $C_2H_5$ | Ph | quinolin-3-yl | |
| 13.42 | $C_2H_5$ | Ph | quinolin-4-yl | |
| 13.43 | n-$C_3H_7$ | Ph | 2-furyl | |
| 13.44 | n-$C_3H_7$ | Ph | 3-furyl | |
| 13.45 | n-$C_3H_7$ | Ph | 2-thienyl | |
| 13.46 | n-$C_3H_7$ | Ph | 3-thienyl | |
| 13.47 | n-$C_3H_7$ | Ph | 2-pyridyl | |
| 13.48 | n-$C_3H_7$ | Ph | 3-pyridyl | |
| 13.49 | n-$C_3H_7$ | Ph | 4-pyridyl | |
| 13.50 | n-$C_3H_7$ | Ph | pyrazinyl | |
| 13.51 | n-$C_3H_7$ | Ph | pyrimidin-2-yl | |
| 13.52 | n-$C_3H_7$ | Ph | pyrimidin-4-yl | |
| 13.53 | n-$C_3H_7$ | Ph | pyrimidin-5-yl | |
| 13.54 | n-$C_3H_7$ | Ph | quinolin-2-yl | |
| 13.55 | n-$C_3H_7$ | Ph | quinolin-3-yl | |
| 13.56 | n-$C_3H_7$ | Ph | quinolin-4-yl | |
| 13.57 | iso-$C_3H_7$ | Ph | 2-pyridyl | |

TABLE 13-continued

| Compd | R$_2$ | R$_3$ | R$_7$ | Properties/Comments |
|---|---|---|---|---|
| 13.58 | n-C$_4$H$_9$ | Ph | 2-pyridyl | |
| 13.59 | iso-C$_4$H$_9$ | Ph | 2-pyridyl | |
| 13.60 | c-C$_3$H$_5$ | Ph | 2-pyridyl | |
| 13.61 | 1-CH$_3$-c-C$_3$H$_5$ | Ph | 2-pyridyl | |
| 13.62 | C(H)=N—OCH$_3$ | Ph | 2-pyridyl | |
| 13.63 | C(CH$_3$)=NOCH$_3$ | Ph | 2-pyridyl | |
| 13.64 | C(C$_2$H$_5$)=NOCH$_3$ | Ph | 2-pyridyl | |
| 13.65 | Ph | Ph | 2-pyridyl | |
| 13.66 | Ph | Ph | 2-pyridyl | |
| 13.67 | Ph | Ph | 2-pyridyl | |
| 13.68 | Ph | Ph | 2-pyridyl | |
| 13.69 | 4-Cl(Ph) | Ph | 2-pyridyl | |
| 13.70 | 4-Cl(Ph) | Ph | 2-pyridyl | |
| 13.71 | 4-F(Ph) | Ph | 2-pyridyl | |
| 13.72 | 4-F(Ph) | Ph | 2-pyridyl | |
| 13.73 | 4-CF$_3$(Ph) | Ph | 2-pyridyl | |
| 13.74 | 4-CF$_3$(Ph) | Ph | 2-pyridyl | |
| 13.75 | 2,4-Cl(Ph) | Ph | 2-pyridyl | |
| 13.76 | 2,4-Cl(Ph) | Ph | 2-pyridyl | |
| 13.77 | 2,4-F(Ph) | Ph | 2-pyridyl | |
| 13.78 | C$_2$H$_5$ | 2-Cl(Ph) | 2-pyridyl | |
| 13.79 | n-C$_3$H$_7$ | 2-Cl(Ph) | 2-pyridyl | |
| 13.80 | iso-C$_3$H$_7$ | 2-Cl(Ph) | 2-pyridyl | |
| 13.81 | n-C$_4$H$_9$ | 2-Cl(Ph) | 2-pyridyl | |
| 13.82 | iso-C$_4$H$_9$ | 2-Cl(Ph) | 2-pyridyl | |
| 13.83 | c-C$_3$H$_5$ | 2-Cl(Ph) | 2-pyridyl | |
| 13.84 | 1-CH$_3$-c-C$_3$H$_5$ | 2-Cl(Ph) | 2-pyridyl | |
| 13.85 | C(H)=N—OCH$_3$ | 2-Cl(Ph) | 2-pyridyl | |
| 13.86 | C(CH$_3$)=N—OCH$_3$ | 2-Cl(Ph) | 2-pyridyl | |
| 13.87 | C(C$_2$H$_5$)=N—OCH$_3$ | 2-Cl(Ph) | 2-pyridyl | |
| 13.88 | Ph | 2-Cl(Ph) | 2-pyridyl | |
| 13.89 | Ph | 2-Cl(Ph) | 2-pyridyl | |
| 13.90 | Ph | 2-Cl(Ph) | 2-pyridyl | |
| 13.91 | Ph | 2-Cl(Ph) | 2-pyridyl | |
| 13.92 | 4-Cl(Ph) | 2-Cl(Ph) | 2-pyridyl | |
| 13.93 | 4-Cl(Ph) | 2-Cl(Ph) | 2-pyridyl | |
| 13.94 | 4-F(Ph) | 2-Cl(Ph) | 2-pyridyl | |
| 13.95 | 4-F(Ph) | 2-Cl(Ph) | 2-pyridyl | |
| 13.96 | 4-CF$_3$(Ph) | 2-Cl(Ph) | 2-pyridyl | |
| 13.97 | 4-CF$_3$(Ph) | 2-Cl(Ph) | 2-pyridyl | |
| 13.98 | 2,4-Cl(Ph) | 2-Cl(Ph) | 2-pyridyl | |
| 13.99 | 2,4-Cl(Ph) | 2-Cl(Ph) | 2-pyridyl | |
| 13.100 | 2,4-F(Ph) | 2-Cl(Ph) | 2-pyridyl | |
| 13.101 | H | 4-Cl(Ph) | 3-pyridyl | |
| 13.102 | CH$_3$ | 4-Cl(Ph) | 3-pyridyl | |
| 13.103 | C$_2$H$_5$ | 4-Cl(Ph) | 3-pyridyl | |
| 13.104 | n-C$_3$H$_7$ | 4-Cl(Ph) | 3-pyridyl | |
| 13.105 | iso-C$_3$H$_7$ | 4-Cl(Ph) | 3-pyridyl | |
| 13.106 | n-C$_4$H$_9$ | 4-Cl(Ph) | 3-pyridyl | |
| 13.107 | iso-C$_4$H$_9$ | 4-Cl(Ph) | 3-pyridyl | |
| 13.108 | c-C$_3$H$_5$ | 4-Cl(Ph) | 3-pyridyl | |
| 13.109 | 1-CH$_3$-c-C$_3$H$_5$ | 4-Cl(Ph) | 3-pyridyl | |
| 13.110 | C(H)=N—OCH$_3$ | 4-Cl(Ph) | 3-pyridyl | |
| 13.111 | C(CH$_3$)=N—OCH$_3$ | 4-Cl(Ph) | 3-pyridyl | |
| 13.112 | C(C$_2$H$_5$)=N—OCH$_3$ | 4-Cl(Ph) | 3-pyridyl | |
| 13.113 | Ph | 4-Cl(Ph) | 3-pyridyl | |
| 13.114 | 2-Cl(Ph) | 4-Cl(Ph) | 3-pyridyl | |
| 13.115 | 3-Cl(Ph) | 4-Cl(Ph) | 3-pyridyl | |
| 13.116 | 4-Cl(Ph) | 4-Cl(Ph) | 3-pyridyl | |
| 13.117 | 2-F(Ph) | 4-Cl(Ph) | 3-pyridyl | |
| 13.118 | 3-F(Ph) | 4-Cl(Ph) | 3-pyridyl | |
| 13.119 | 4-F(Ph) | 4-Cl(Ph) | 3-pyridyl | |
| 13.120 | 2-CF$_3$(Ph) | 4-Cl(Ph) | 3-pyridyl | |
| 13.121 | 3-CF$_3$(Ph) | 4-Cl(Ph) | 3-pyridyl | |
| 13.122 | 4-CF$_3$(Ph) | 4-Cl(Ph) | 3-pyridyl | |
| 13.123 | 2,4-Cl(Ph) | 4-Cl(Ph) | 3-pyridyl | |
| 13.124 | 2,4-F(Ph) | 4-Cl(Ph) | 3-pyridyl | |
| 13.125 | H | 4-CF$_3$(Ph) | 4-pyridyl | |
| 13.126 | CH$_3$ | 4-CF$_3$(Ph) | 4-pyridyl | |
| 13.127 | C$_2$H$_5$ | 4-CF$_3$(Ph) | 4-pyridyl | |
| 13.128 | n-C$_3$H$_7$ | 4-CF$_3$(Ph) | 4-pyridyl | |
| 13.129 | iso-C$_3$H$_7$ | 4-CF$_3$(Ph) | 4-pyridyl | |
| 13.130 | n-C$_4$H$_9$ | 4-CF$_3$(Ph) | 4-pyridyl | |
| 13.131 | iso-C$_4$H$_9$ | 4-CF$_3$(Ph) | 4-pyridyl | |
| 13.132 | c-C$_3$H$_5$ | 4-CF$_3$(Ph) | 4-pyridyl | |
| 13.133 | 1-CH$_3$-c-C$_3$H$_5$ | 4-CF$_3$(Ph) | 4-pyridyl | |
| 13.134 | C(H)=N—OCH$_3$ | 4-CF$_3$(Ph) | 4-pyridyl | |
| 13.135 | C(CH$_3$)=N—OCH$_3$ | 4-CF$_3$(Ph) | 4-pyridyl | |
| 13.136 | C(C$_2$H$_5$)=N—OCH$_3$ | 4-CF$_3$(Ph) | 4-pyridyl | |
| 13.137 | Ph | 4-CF$_3$(Ph) | 4-pyridyl | |
| 13.138 | 2-Cl(Ph) | 4-CF$_3$(Ph) | 4-pyridyl | |
| 13.139 | 3-Cl(Ph) | 4-CF$_3$(Ph) | 4-pyridyl | |
| 13.140 | 4-Cl(Ph) | 4-CF$_3$(Ph) | 4-pyridyl | |
| 13.141 | 2-F(Ph) | 4-CF$_3$(Ph) | 4-pyridyl | |
| 13.142 | 3-F(Ph) | 4-CF$_3$(Ph) | 4-pyridyl | |
| 13.143 | 4-F(Ph) | 4-CF$_3$(Ph) | 4-pyridyl | |
| 13.144 | 2-CF$_3$(Ph) | 4-Cl(Ph) | 4-pyridyl | |
| 13.145 | 3-CF$_3$(Ph) | 4-Cl(Ph) | 4-pyridyl | |
| 13.146 | 4-CF$_3$(Ph) | 4-Cl(Ph) | 4-pyridyl | |
| 13.147 | 2,4-Cl(Ph) | 4-Cl(Ph) | 4-pyridyl | |
| 13.148 | 2,4-F(Ph) | 4-Cl(Ph) | 4-pyridyl | |
| 13.149 | H | 1-napthyl | 2-thienyl | |
| 13.150 | CH$_3$ | 1-napthyl | 2-thienyl | |
| 13.151 | C$_2$H$_5$ | 1-napthyl | 2-thienyl | |
| 13.152 | n-C$_3$H$_7$ | 1-napthyl | 2-thienyl | |
| 13.153 | iso-C$_3$H$_7$ | 1-napthyl | 2-thienyl | |
| 13.154 | n-C$_4$H$_9$ | 1-napthyl | 2-thienyl | |
| 13.155 | iso-C$_4$H$_9$ | 1-napthyl | 2-thienyl | |
| 13.156 | c-C$_3$H$_5$ | 1-napthyl | 2-thienyl | |
| 13.157 | 1-CH$_3$-c-C$_3$H$_5$ | 1-napthyl | 2-thienyl | |
| 13.158 | C(H)=N—OCH$_3$ | 1-napthyl | 2-thienyl | |
| 13.159 | C(CH$_3$)=N—OCH$_3$ | 1-napthyl | 2-thienyl | |
| 13.160 | C(C$_2$H$_5$)=N—OCH$_3$ | 1-napthyl | 2-thienyl | |
| 13.161 | Ph | 1-napthyl | 2-thienyl | |
| 13.162 | 2-Cl(Ph) | 1-napthyl | 2-thienyl | |
| 13.163 | 3-Cl(Ph) | 1-napthyl | 2-thienyl | |
| 13.164 | 4-Cl(Ph) | 1-napthyl | 2-thienyl | |
| 13.165 | 2-F(Ph) | 1-napthyl | 2-thienyl | |
| 13.166 | 3-F(Ph) | 1-napthyl | 2-thienyl | |
| 13.167 | 4-F(Ph) | 1-napthyl | 2-thienyl | |
| 13.168 | 2-CF$_3$(Ph) | 1-napthyl | 2-thienyl | |
| 13.169 | 3-CF$_3$(Ph) | 1-napthyl | 2-thienyl | |
| 13.170 | 4-CF$_3$(Ph) | 1-napthyl | 2-thienyl | |
| 13.171 | 2,4-Cl(Ph) | 1-napthyl | 2-thienyl | |
| 13.172 | 2,4-F(Ph) | 1-napthyl | 2-thienyl | |
| 13.173 | H | 2-napthyl | 3-thienyl | |
| 13.174 | CH$_3$ | 2-napthyl | 3-thienyl | |
| 13.175 | C$_2$H$_5$ | 2-napthyl | 3-thienyl | |
| 13.176 | n-C$_3$H$_7$ | 2-napthyl | 3-thienyl | |
| 13.177 | iso-C$_3$H$_7$ | 2-napthyl | 3-thienyl | |
| 13.178 | n-C$_4$H$_9$ | 2-napthyl | 3-thienyl | |
| 13.179 | iso-C$_4$H$_9$ | 2-napthyl | 3-thienyl | |
| 13.180 | c-C$_3$H$_5$ | 2-napthyl | 3-thienyl | |
| 13.181 | 1-CH$_3$-c-C$_3$H$_5$ | 2-napthyl | 3-thienyl | |
| 13.182 | C(H)=N—OCH$_3$ | 2-napthyl | 3-thienyl | |
| 13.183 | C(CH$_3$)=N—OCH$_3$ | 2-napthyl | 3-thienyl | |
| 13.184 | C(C$_2$H$_5$)=N—OCH$_3$ | 2-napthyl | 3-thienyl | |
| 13.185 | Ph | 2-napthyl | 3-thienyl | |
| 13.186 | 2-Cl(Ph) | 2-napthyl | 3-thienyl | |
| 13.187 | 3-Cl(Ph) | 2-napthyl | 3-thienyl | |
| 13.188 | 4-Cl(Ph) | 2-napthyl | 3-thienyl | |
| 13.189 | 2-F(Ph) | 2-napthyl | 3-thienyl | |
| 13.190 | 3-F(Ph) | 2-napthyl | 3-thienyl | |
| 13.191 | 4-F(Ph) | 2-napthyl | 3-thienyl | |
| 13.192 | 2-CF$_3$(Ph) | 2-napthyl | 3-thienyl | |
| 13.193 | 3-CF$_3$(Ph) | 2-napthyl | 3-thienyl | |
| 13.194 | 4-CF$_3$(Ph) | 2-napthyl | 3-thienyl | |
| 13.195 | 2,4-Cl(Ph) | 2-napthyl | 3-thienyl | |
| 13.196 | 2,4-F(Ph) | 2-napthyl | 3-thienyl | |

Table 14:
Compounds 14.1 to 14.196 are compounds of Formula V (X=N and Z=O) wherein the substituents R$_2$, R$_3$, and R$_7$ are defined in Table 13.

Table 15:
Compounds 15.1 to 15.196 are compounds of Formula VII (X=N and Z=NH) wherein the substituents R$_2$, R$_3$, and R$_7$ are defined in Table 13.

Typical compounds encompassed by the present invention of Formula I (where A=R$_4$=R$_5$=R$_6$=H) include those compounds presented in Table 16 of Formula IV (X=CH and Z is O) where $R_2$, $R_3$ and $R_7$ are defined in Table 16.

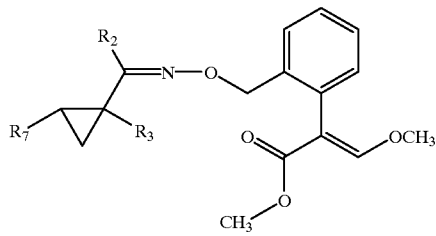

Formula IV

TABLE 16

| Compd | $R_2$ | $R_3$ | $R_7$ | Properties Comments |
|---|---|---|---|---|
| 16.1 | H | 2-furyl | 2-furyl | |
| 16.2 | $CH_3$ | 2-furyl | 2-furyl | |
| 16.3 | $C_2H_5$ | 2-furyl | 2-furyl | |
| 16.4 | $n\text{-}C_3H_7$ | 2-furyl | 2-furyl | |
| 16.5 | $iso\text{-}C_3H_7$ | 2-furyl | 2-furyl | |
| 16.6 | $n\text{-}C_4H_9$ | 2-furyl | 2-furyl | |
| 16.7 | $iso\text{-}C_4H_9$ | 2-furyl | 2-furyl | |
| 16.8 | $c\text{-}C_3H_5$ | 2-furyl | 2-furyl | |
| 16.9 | $1\text{-}CH_3\text{-}c\text{-}C_3H_5$ | 2-furyl | 2-furyl | |
| 16.10 | $C(H)=NOCH_3$ | 2-furyl | 2-furyl | |
| 16.11 | $C(CH_3)=NOCH_3$ | 2-furyl | 2-furyl | |
| 16.12 | $C(C_2H_5)=NOCH_3$ | 2-furyl | 2-furyl | |
| 16.13 | Ph | 2-furyl | 2-furyl | |
| 16.14 | 2-Cl(Ph) | 2-furyl | 2-furyl | |
| 16.15 | 3-Cl(Ph) | 2-furyl | 2-furyl | |
| 16.16 | 4-Cl(Ph) | 2-furyl | 2-furyl | |
| 16.17 | 2-F(Ph) | 2-furyl | 2-furyl | |
| 16.18 | 3-F(Ph) | 2-furyl | 2-furyl | |
| 16.19 | 4-F(Ph) | 2-furyl | 2-furyl | |
| 16.20 | $2\text{-}CF_3(Ph)$ | 2-furyl | 2-furyl | |
| 16.21 | $3\text{-}CF_3(Ph)$ | 2-furyl | 2-furyl | |
| 16.22 | $4\text{-}CF_3(Ph)$ | 2-furyl | 2-furyl | |
| 16.23 | 2,4-Cl(Ph) | 2-furyl | 2-furyl | |
| 16.24 | 2,4-F(Ph) | 2-furyl | 2-furyl | |
| 16.25 | H | 3-furyl | 2-furyl | |
| 16.26 | $CH_3$ | 3-furyl | 2-furyl | |
| 16.27 | $C_2H_5$ | 3-furyl | 2-furyl | |
| 16.28 | $n\text{-}C_3H_7$ | 3-furyl | 2-furyl | |
| 16.29 | $iso\text{-}C_3H_7$ | 3-furyl | 2-furyl | |
| 16.30 | $n\text{-}C_4H_9$ | 3-furyl | 2-furyl | |
| 16.31 | $iso\text{-}C_4H_9$ | 3-furyl | 2-furyl | |
| 16.32 | $c\text{-}C_3H_5$ | 3-furyl | 2-furyl | |
| 16.33 | $1\text{-}CH_3\text{-}c\text{-}C_3H_5$ | 3-furyl | 2-furyl | |
| 16.34 | $C(H)=NOCH_3$ | 3-furyl | 2-furyl | |
| 16.35 | $C(CH_3)=NOCH_3$ | 3-furyl | 2-furyl | |
| 16.36 | $C(C_2H_5)=NOCH_3$ | 3-furyl | 2-furyl | |
| 16.37 | Ph | 3-furyl | 2-furyl | |
| 16.38 | 2-Cl(Ph) | 3-furyl | 2-furyl | |
| 16.39 | 3-Cl(Ph) | 3-furyl | 2-furyl | |
| 16.40 | 4-Cl(Ph) | 3-furyl | 2-furyl | |
| 16.41 | 2-F(Ph) | 3-furyl | 2-furyl | |
| 16.42 | 3-F(Ph) | 3-furyl | 2-furyl | |
| 16.43 | 4-F(Ph) | 3-furyl | 2-furyl | |
| 16.44 | $2\text{-}CF_3(Ph)$ | 3-furyl | 2-furyl | |
| 16.45 | $3\text{-}CF_3(Ph)$ | 3-furyl | 2-furyl | |
| 16.46 | $4\text{-}CF_3(Ph)$ | 3-furyl | 2-furyl | |
| 16.47 | 2,4-Cl(Ph) | 3-furyl | 2-furyl | |
| 16.48 | 2,4-F(Ph) | 3-furyl | 2-furyl | |
| 16.49 | H | 2-thienyl | 2-furyl | |
| 16.50 | $CH_3$ | 2-thienyl | 2-furyl | |
| 16.51 | $C_2H_5$ | 2-thienyl | 2-furyl | |
| 16.52 | $n\text{-}C_3H_7$ | 2-thienyl | 2-furyl | |
| 16.53 | $iso\text{-}C_3H_7$ | 2-thienyl | 2-furyl | |
| 16.54 | $n\text{-}C_4H_9$ | 2-thienyl | 2-furyl | |
| 16.55 | $iso\text{-}C_4H_9$ | 2-thienyl | 2-furyl | |
| 16.56 | $c\text{-}C_3H_5$ | 2-thienyl | 2-furyl | |
| 16.57 | $1\text{-}CH_3\text{-}c\text{-}C_3H_5$ | 2-thienyl | 2-furyl | |
| 16.58 | $C(H)=N\text{—}OCH_3$ | 2-thienyl | 2-furyl | |
| 16.59 | $C(CH_3)=NOCH_3$ | 2-thienyl | 2-furyl | |
| 16.60 | $C(C_2H_5)=NOCH_3$ | 2-thienyl | 2-furyl | |
| 16.61 | Ph | 2-thienyl | 2-furyl | |
| 16.62 | 2-Cl(Ph) | 2-thienyl | 2-furyl | |
| 16.63 | 3-Cl(Ph) | 2-thienyl | 2-furyl | |
| 16.64 | 4-Cl(Ph) | 2-thienyl | 2-furyl | |
| 16.65 | 2-F(Ph) | 2-thienyl | 2-furyl | |
| 16.66 | 3-F(Ph) | 2-thienyl | 2-furyl | |
| 16.67 | 4-F(Ph) | 2-thienyl | 2-furyl | |
| 16.68 | $2\text{-}CF_3(Ph)$ | 2-thienyl | 2-furyl | |
| 16.69 | $3\text{-}CF_3(Ph)$ | 2-thienyl | 2-furyl | |
| 16.70 | $4\text{-}CF_3(Ph)$ | 2-thienyl | 2-furyl | |
| 16.71 | 2,4-Cl(Ph) | 2-thienyl | 2-furyl | |
| 16.72 | 2,4-F(Ph) | 2-thienyl | 2-furyl | |
| 16.73 | H | 3-thienyl | 2-furyl | |
| 16.74 | $CH_3$ | 3-thienyl | 2-furyl | |
| 16.75 | $C_2H_5$ | 3-thienyl | 2-furyl | |
| 16.76 | $n\text{-}C_3H_7$ | 3-thienyl | 2-furyl | |
| 16.77 | $iso\text{-}C_3H_7$ | 3-thienyl | 2-furyl | |
| 16.79 | $iso\text{-}C_4H_9$ | 3-thienyl | 2-furyl | |
| 16.78 | $n\text{-}C_4H_9$ | 3-thienyl | 2-furyl | |
| 16.80 | $c\text{-}C_3H_5$ | 3-thienyl | 2-furyl | |
| 16.81 | $1\text{-}CH_3\text{-}c\text{-}C_3H_5$ | 3-thienyl | 2-furyl | |
| 16.82 | $C(H)=NOCH_3$ | 3-thienyl | 2-furyl | |
| 16.83 | $C(CH_3)=NOCH_3$ | 3-thienyl | 2-furyl | |
| 16.84 | $C(C_2H_5)=NOCH_3$ | 3-thienyl | 2-furyl | |
| 16.85 | Ph | 3-thienyl | 2-furyl | |
| 16.86 | 2-Cl(Ph) | 3-thienyl | 2-furyl | |
| 16.87 | 3-Cl(Ph) | 3-thienyl | 2-furyl | |
| 16.88 | 4-Cl(Ph) | 3-thienyl | 2-furyl | |
| 16.89 | 2-F(Ph) | 3-thienyl | 2-furyl | |
| 16.90 | 3-F(Ph) | 3-thienyl | 2-furyl | |
| 16.91 | 4-F(Ph) | 3-thienyl | 2-furyl | |
| 16.92 | $2\text{-}CF_3(Ph)$ | 3-thienyl | 2-furyl | |
| 16.93 | $3\text{-}CF_3(Ph)$ | 3-thienyl | 2-furyl | |
| 16.94 | $4\text{-}CF_3(Ph)$ | 3-thienyl | 2-furyl | |
| 16.95 | 2,4-Cl(Ph) | 3-thienyl | 2-furyl | |
| 16.96 | 2,4-F(Ph) | 3-thienyl | 2-furyl | |
| 16.97 | H | 2-pyridyl | 2-furyl | |
| 16.98 | $CH_3$ | 2-pyridyl | 2-furyl | |
| 16.99 | $C_2H_5$ | 2-pyridyl | 2-furyl | |
| 16.100 | $n\text{-}C_3H_7$ | 2-pyridyl | 2-furyl | |
| 16.101 | $iso\text{-}C_3H_7$ | 2-pyridyl | 2-furyl | |
| 16.102 | $n\text{-}C_4H_9$ | 2-pyridyl | 2-furyl | |
| 16.103 | $iso\text{-}C_4H_9$ | 2-pyridyl | 2-furyl | |
| 16.104 | $c\text{-}C_3H_5$ | 2-pyridyl | 2-furyl | |
| 16.105 | $1\text{-}CH_3\text{-}c\text{-}C_3H_5$ | 2-pyridyl | 2-furyl | |
| 16.106 | $C(H)=NOCH_3$ | 2-pyridyl | 2-furyl | |
| 16.107 | $C(CH_3)=NOCH_3$ | 2-pyridyl | 2-furyl | |
| 16.108 | $C(C_2H_5)=NOCH_3$ | 2-pyridyl | 2-furyl | |
| 16.109 | Ph | 2-pyridyl | 2-furyl | |
| 16.110 | 2-Cl(Ph) | 2-pyridyl | 2-furyl | |
| 16.111 | 3-Cl(Ph) | 2-pyridyl | 2-furyl | |
| 16.112 | 4-Cl(Ph) | 2-pyridyl | 2-furyl | |
| 16.113 | 2-F(Ph) | 2-pyridyl | 2-furyl | |
| 16.114 | 3-F(Ph) | 2-pyridyl | 2-furyl | |
| 16.115 | 4-F(Ph) | 2-pyridyl | 2-furyl | |
| 16.116 | $2\text{-}CF_3(Ph)$ | 2-pyridyl | 2-furyl | |
| 16.117 | $3\text{-}CF_3(Ph)$ | 2-pyridyl | 2-furyl | |
| 16.118 | $4\text{-}CF_3(Ph)$ | 2-pyridyl | 2-furyl | |
| 16.119 | 2,4-Cl(Ph) | 2-pyridyl | 2-furyl | |
| 16.120 | 2,4-F(Ph) | 2-pyridyl | 2-furyl | |
| 16.121 | H | 3-pyridyl | 2-furyl | |
| 16.122 | $CH_3$ | 3-pyridyl | 2-furyl | |
| 16.123 | $C_2H_5$ | 3-pyridyl | 2-furyl | |
| 16.124 | $n\text{-}C_3H_7$ | 3-pyridyl | 2-furyl | |
| 16.125 | $iso\text{-}C_3H_7$ | 3-pyridyl | 2-furyl | |
| 16.126 | $n\text{-}C_4H_9$ | 3-pyridyl | 2-furyl | |

TABLE 16-continued

| Compd | $R_2$ | $R_3$ | $R_7$ | Properties Comments |
|---|---|---|---|---|
| 16.127 | iso-$C_4H_9$ | 3-pyridyl | 2-furyl | |
| 16.128 | c-$C_3H_5$ | 3-pyridyl | 2-furyl | |
| 16.129 | 1-$CH_3$-c-$C_3H_5$ | 3-pyridyl | 2-furyl | |
| 16.130 | C(H)=$NOCH_3$ | 3-pyridyl | 2-furyl | |
| 16.131 | C($CH_3$)=$NOCH_3$ | 3-pyridyl | 2-furyl | |
| 16.132 | C($C_2H_5$)=$NOCH_3$ | 3-pyridyl | 2-furyl | |
| 16.133 | Ph | 3-pyridyl | 2-furyl | |
| 16.134 | 2-Cl(Ph) | 3-pyridyl | 2-furyl | |
| 16.135 | 3-Cl(Ph) | 3-pyridyl | 2-furyl | |
| 16.136 | 4-Cl(Ph) | 3-pyridyl | 2-furyl | |
| 16.137 | 2-F(Ph) | 3-pyridyl | 2-furyl | |
| 16.138 | 3-F(Ph) | 3-pyridyl | 2-furyl | |
| 16.139 | 4-F(Ph) | 3-pyridyl | 2-furyl | |
| 16.140 | 2-$CF_3$(Ph) | 3-pyridyl | 2-furyl | |
| 16.141 | 3-$CF_3$(Ph) | 3-pyridyl | 2-furyl | |
| 16.142 | 4-$CF_3$(Ph) | 3-pyridyl | 2-furyl | |
| 16.143 | 2,4-Cl(Ph) | 3-pyridyl | 2-furyl | |
| 16.144 | 2,4-F(Ph) | 3-pyridyl | 2-furyl | |
| 16.145 | H | 4-pyridyl | 2-furyl | |
| 16.146 | $CH_3$ | 4-pyridyl | 2-furyl | |
| 16.147 | $C_2H_5$ | 4-pyridyl | 2-furyl | |
| 16.148 | n-$C_3H_7$ | 4-pyridyl | 2-furyl | |
| 16.149 | iso-$C_3H_7$ | 4-pyridyl | 2-furyl | |
| 16.150 | n-$C_4H_9$ | 4-pyridyl | 2-furyl | |
| 16.151 | iso-$C_4H_9$ | 4-pyridyl | 2-furyl | |
| 16.152 | c-$C_3H_5$ | 4-pyridyl | 2-furyl | |
| 16.153 | 1-$CH_3$-c-$C_3H_5$ | 4-pyridyl | 2-furyl | |
| 16.154 | C(H)=N—$OCH_3$ | 4-pyridyl | 2-furyl | |
| 16.155 | C($CH_3$)=$NOCH_3$ | 4-pyridyl | 2-furyl | |
| 16.156 | C($C_2H_5$)=$NOCH_3$ | 4-pyridyl | 2-furyl | |
| 16.157 | Ph | 4-pyridyl | 2-furyl | |
| 16.158 | 2-Cl(Ph) | 4-pyridyl | 2-furyl | |
| 16.159 | 3-Cl(Ph) | 4-pyridyl | 2-furyl | |
| 16.160 | 4-Cl(Ph) | 4-pyridyl | 2-furyl | |
| 16.161 | 2-F(Ph) | 4-pyridyl | 2-furyl | |
| 16.162 | 3-F(Ph) | 4-pyridyl | 2-furyl | |
| 16.163 | 4-F(Ph) | 4-pyridyl | 2-furyl | |
| 16.164 | 2-$CF_3$(Ph) | 4-pyridyl | 2-furyl | |
| 16.165 | 3-$CF_3$(Ph) | 4-pyridyl | 2-furyl | |
| 16.166 | 4-$CF_3$(Ph) | 4-pyridyl | 2-furyl | |
| 16.167 | 2,4-Cl(Ph) | 4-pyridyl | 2-furyl | |
| 16.168 | 2,4-F(Ph) | 4-pyridyl | 2-furyl | |
| 16.169 | H | 2-furyl | 2-pyridyl | |
| 16.170 | $CH_3$ | 2-furyl | 2-pyridyl | |
| 16.171 | $C_2H_5$ | 2-furyl | 2-pyridyl | |
| 16.172 | n-$C_3H_7$ | 2-furyl | 2-pyridyl | |
| 16.173 | iso-$C_3H_7$ | 2-furyl | 2-pyridyl | |
| 16.174 | n-$C_4H_9$ | 2-furyl | 2-pyridyl | |
| 16.175 | iso-$C_4H_9$ | 2-furyl | 2-pyridyl | |
| 16.176 | c-$C_3H_5$ | 2-furyl | 2-pyridyl | |
| 16.177 | 1-$CH_3$-c-$C_3H_5$ | 2-furyl | 2-pyridyl | |
| 16.178 | C(H)=$NOCH_3$ | 2-furyl | 2-pyridyl | |
| 16.179 | C($CH_3$)=$NOCH_3$ | 2-furyl | 2-pyridyl | |
| 16.180 | C($C_2H_5$)=$NOCH_3$ | 2-furyl | 2-pyridyl | |
| 16.181 | Ph | 2-furyl | 2-pyridyl | |
| 16.182 | 2-Cl(Ph) | 2-furyl | 2-pyridyl | |
| 16.183 | 3-Cl(Ph) | 2-furyl | 2-pyridyl | |
| 16.184 | 4-Cl(Ph) | 2-furyl | 2-pyridyl | |
| 16.185 | 2-F(Ph) | 2-furyl | 2-pyridyl | |
| 16.186 | 3-F(Ph) | 2-furyl | 2-pyridyl | |
| 16.187 | 4-F(Ph) | 2-furyl | 2-pyridyl | |
| 16.188 | 2-$CF_3$(Ph) | 2-furyl | 2-pyridyl | |
| 16.189 | 3-$CF_3$(Ph) | 2-furyl | 2-pyridyl | |
| 16.190 | 4-$CF_3$(Ph) | 2-furyl | 2-pyridyl | |
| 16.191 | 2,4-Cl(Ph) | 2-furyl | 2-pyridyl | |
| 16.192 | 2,4-F(Ph) | 2-furyl | 2-pyridyl | |
| 16.193 | H | 3-furyl | 2-pyridyl | |
| 16.194 | $CH_3$ | 3-furyl | 2-pyridyl | |
| 16.195 | $C_2H_5$ | 3-furyl | 2-pyridyl | |
| 16.196 | n-$C_3H_7$ | 3-furyl | 2-pyridyl | |
| 16.197 | iso-$C_3H_7$ | 3-furyl | 2-pyridyl | |
| 16.198 | n-$C_4H_9$ | 3-furyl | 2-pyridyl | |
| 16.199 | iso-$C_4H_9$ | 3-furyl | 2-pyridyl | |
| 16.200 | c-$C_3H_5$ | 3-furyl | 2-pyridyl | |
| 16.201 | 1-$CH_3$-c-$C_3H_5$ | 3-furyl | 2-pyridyl | |
| 16.202 | C(H)=N—$OCH_3$ | 3-furyl | 2-pyridyl | |
| 16.203 | C($CH_3$)=$NOCH_3$ | 3-furyl | 2-pyridyl | |
| 16.204 | C($C_2H_5$)=$NOCH_3$ | 3-furyl | 2-pyridyl | |
| 16.205 | Ph | 3-furyl | 2-pyridyl | |
| 16.206 | 2-Cl(Ph) | 3-furyl | 2-pyridyl | |
| 16.207 | 3-Cl(Ph) | 3-furyl | 2-pyridyl | |
| 16.208 | 4-Cl(Ph) | 3-furyl | 2-pyridyl | |
| 16.209 | 2-F(Ph) | 3-furyl | 2-pyridyl | |
| 16.210 | 3-F(Ph) | 3-furyl | 2-pyridyl | |
| 16.211 | 4-F(Ph) | 3-furyl | 2-pyridyl | |
| 16.212 | 2-$CF_3$(Ph) | 3-furyl | 2-pyridyl | |
| 16.213 | 3-$CF_3$(Ph) | 3-furyl | 2-pyridyl | |
| 16.214 | 4-$CF_3$(Ph) | 3-furyl | 2-pyridyl | |
| 16.215 | 2,4-Cl(Ph) | 3-furyl | 2-pyridyl | |
| 16.216 | 2,4-F(Ph) | 3-furyl | 2-pyridyl | |
| 16.217 | H | 2-thienyl | 2-pyridyl | |
| 16.218 | $CH_3$ | 2-thienyl | 2-pyridyl | |
| 16.219 | $C_2H_5$ | 2-thienyl | 2-pyridyl | |
| 16.220 | n-$C_3H_7$ | 2-thienyl | 2-pyridyl | |
| 16.221 | iso-$C_3H_7$ | 2-thienyl | 2-pyridyl | |
| 16.222 | n-$C_4H_9$ | 2-thienyl | 2-pyridyl | |
| 16.223 | iso-$C_4H_9$ | 2-thienyl | 2-pyridyl | |
| 16.224 | c-$C_3H_5$ | 2-thienyl | 2-pyridyl | |
| 16.225 | 1-$CH_3$-c-$C_3H_5$ | 2-thienyl | 2-pyridyl | |
| 16.226 | C(H)=$NOCH_3$ | 2-thienyl | 2-pyridyl | |
| 16.227 | C($CH_3$)=$NOCH_3$ | 2-thienyl | 2-pyridyl | |
| 16.228 | C($C_2H_5$)=$NOCH_3$ | 2-thienyl | 2-pyridyl | |
| 16.229 | Ph | 2-thienyl | 2-pyridyl | |
| 16.230 | 2-Cl(Ph) | 2-thienyl | 2-pyridyl | |
| 16.231 | 3-Cl(Ph) | 2-thienyl | 2-pyridyl | |
| 16.232 | 4-Cl(Ph) | 2-thienyl | 2-pyridyl | |
| 16.233 | 2-F(Ph) | 2-thienyl | 2-pyridyl | |
| 16.234 | 3-F(Ph) | 2-thienyl | 2-pyridyl | |
| 16.235 | 4-F(Ph) | 2-thienyl | 2-pyridyl | |
| 16.236 | 2-$CF_3$(Ph) | 2-thienyl | 2-pyridyl | |
| 16.237 | 3-$CF_3$(Ph) | 2-thienyl | 2-pyridyl | |
| 16.238 | 4-$CF_3$(Ph) | 2-thienyl | 2-pyridyl | |
| 16.239 | 2,4-Cl(Ph) | 2-thienyl | 2-pyridyl | |
| 16.240 | 2,4-F(Ph) | 2-thienyl | 2-pyridyl | |
| 16.241 | H | 3-thienyl | 2-pyridyl | |
| 16.242 | $CH_3$ | 3-thienyl | 2-pyridyl | |
| 16.243 | $C_2H_5$ | 3-thienyl | 2-pyridyl | |
| 16.244 | n-$C_3H_7$ | 3-thienyl | 2-pyridyl | |
| 16.245 | iso-$C_3H_7$ | 3-thienyl | 2-pyridyl | |
| 16.246 | n-$C_4H_9$ | 3-thienyl | 2-pyridyl | |
| 16.247 | iso-$C_4H_9$ | 3-thienyl | 2-pyridyl | |
| 16.248 | c-$C_3H_5$ | 3-thienyl | 2-pyridyl | |
| 16.249 | 1-$CH_3$-c-$C_3H_5$ | 3-thienyl | 2-pyridyl | |
| 16.250 | C(H)=N—$OCH_3$ | 3-thienyl | 2-pyridyl | |
| 16.251 | C($CH_3$)=$NOCH_3$ | 3-thienyl | 2-pyridyl | |
| 16.252 | C($C_2H_5$)=$NOCH_3$ | 3-thienyl | 2-pyridyl | |
| 16.253 | Ph | 3-thienyl | 2-pyridyl | |
| 16.254 | 2-Cl(Ph) | 3-thienyl | 2-pyridyl | |
| 16.255 | 3-Cl(Ph) | 3-thienyl | 2-pyridyl | |
| 16.256 | 4-Cl(Ph) | 3-thienyl | 2-pyridyl | |
| 16.257 | 2-F(Ph) | 3-thienyl | 2-pyridyl | |
| 16.258 | 3-F(Ph) | 3-thienyl | 2-pyridyl | |
| 16.259 | 4-F(Ph) | 3-thienyl | 2-pyridyl | |
| 16.260 | 2-$CF_3$(Ph) | 3-thienyl | 2-pyridyl | |
| 16.261 | 3-$CF_3$(Ph) | 3-thienyl | 2-pyridyl | |
| 16.262 | 4-$CF_3$(Ph) | 3-thienyl | 2-pyridyl | |
| 16.263 | 2,4-Cl(Ph) | 3-thienyl | 2-pyridyl | |
| 16.264 | 2,4-F(Ph) | 3-thienyl | 2-pyridyl | |
| 16.265 | H | 2-pyridyl | 2-pyridyl | |
| 16.266 | $CH_3$ | 2-pyridyl | 2-pyridyl | |
| 16.267 | $C_2H_5$ | 2-pyridyl | 2-pyridyl | |
| 16.268 | n-$C_3H_7$ | 2-pyridyl | 2-pyridyl | |
| 16.269 | iso-$C_3H_7$ | 2-pyridyl | 2-pyridyl | |
| 16.270 | n-$C_4H_9$ | 2-pyridyl | 2-pyridyl | |
| 16.271 | iso-$C_4H_9$ | 2-pyridyl | 2-pyridyl | |
| 16.272 | c-$C_3H_5$ | 2-pyridyl | 2-pyridyl | |
| 16.273 | 1-$CH_3$-c-$C_3H_5$ | 2-pyridyl | 2-pyridyl | |
| 16.274 | C(H)=$NOCH_3$ | 2-pyridyl | 2-pyridyl | |

TABLE 16-continued

| Compd | $R_2$ | $R_3$ | $R_7$ | Properties Comments |
|---|---|---|---|---|
| 16.275 | $C(CH_3)$=$NOCH_3$ | 2-pyridyl | 2-pyridyl | |
| 16.276 | $C(C_2H_5)$=$NOCH_3$ | 2-pyridyl | 2-pyridyl | |
| 16.277 | Ph | 2-pyridyl | 2-pyridyl | |
| 16.278 | 2-Cl(Ph) | 2-pyridyl | 2-pyridyl | |
| 16.279 | 3-Cl(Ph) | 2-pyridyl | 2-pyridyl | |
| 16.280 | 4-Cl(Ph) | 2-pyridyl | 2-pyridyl | |
| 16.281 | 2-F(Ph) | 2-pyridyl | 2-pyridyl | |
| 16.282 | 3-F(Ph) | 2-pyridyl | 2-pyridyl | |
| 16.283 | 4-F(Ph) | 2-pyridyl | 2-pyridyl | |
| 16.284 | 2-$CF_3$(Ph) | 2-pyridyl | 2-pyridyl | |
| 16.285 | 3-$CF_3$(Ph) | 2-pyridyl | 2-pyridyl | |
| 16.286 | 4-$CF_3$(Ph) | 2-pyridyl | 2-pyridyl | |
| 16.287 | 2,4-Cl(Ph) | 2-pyridyl | 2-pyridyl | |
| 16.288 | 2,4-F(Ph) | 2-pyridyl | 2-pyridyl | |
| 16.289 | H | 3-pyridyl | 2-pyridyl | |
| 16.290 | $CH_3$ | 3-pyridyl | 2-pyridyl | |
| 16.291 | $C_2H_5$ | 3-pyridyl | 2-pyridyl | |
| 16.292 | n-$C_3H_7$ | 3-pyridyl | 2-pyridyl | |
| 16.293 | iso-$C_3H_7$ | 3-pyridyl | 2-pyridyl | |
| 16.294 | n-$C_4H_9$ | 3-pyridyl | 2-pyridyl | |
| 16.295 | iso-$C_4H_9$ | 3-pyridyl | 2-pyridyl | |
| 16.296 | c-$C_3H_5$ | 3-pyridyl | 2-pyridyl | |
| 16.297 | 1-$CH_3$-c-$C_3H_5$ | 3-pyridyl | 2-pyridyl | |
| 16.298 | C(H)=$NOCH_3$ | 3-pyridyl | 2-pyridyl | |
| 16.299 | $C(CH_3)$=$NOCH_3$ | 3-pyridyl | 2-pyridyl | |
| 16.300 | $C(C_2H_5)$=$NOCH_3$ | 3-pyridyl | 2-pyridyl | |
| 16.301 | Ph | 3-pyridyl | 2-pyridyl | |
| 16.302 | 2-Cl(Ph) | 3-pyridyl | 2-pyridyl | |
| 16.303 | 3-Cl(Ph) | 3-pyridyl | 2-pyridyl | |
| 16.304 | 4-Cl(Ph) | 3-pyridyl | 2-pyridyl | |
| 16.305 | 2-F(Ph) | 3-pyridyl | 2-pyridyl | |
| 16.306 | 3-F(Ph) | 3-pyridyl | 2-pyridyl | |
| 16.307 | 4-F(Ph) | 3-pyridyl | 2-pyridyl | |
| 16.308 | 2-$CF_3$(Ph) | 3-pyridyl | 2-pyridyl | |
| 16.309 | 3-$CF_3$(Ph) | 3-pyridyl | 2-pyridyl | |
| 16.310 | 4-$CF_3$(Ph) | 3-pyridyl | 2-pyridyl | |
| 16.311 | 2,4-Cl(Ph) | 3-pyridyl | 2-pyridyl | |
| 16.312 | 2,4-F(Ph) | 3-pyridyl | 2-pyridyl | |
| 16.313 | H | 4-pyridyl | 2-pyridyl | |
| 16.314 | $CH_3$ | 4-pyridyl | 2-pyridyl | |
| 16.315 | $C_2H_5$ | 4-pyridyl | 2-pyridyl | |
| 16.316 | n-$C_3H_7$ | 4-pyridyl | 2-pyridyl | |
| 16.317 | iso-$C_3H_7$ | 4-pyridyl | 2-pyridyl | |
| 16.318 | n-$C_4H_9$ | 4-pyridyl | 2-pyridyl | |
| 16.319 | iso-$C_4H_9$ | 4-pyridyl | 2-pyridyl | |
| 16.320 | c-$C_3H_5$ | 4-pyridyl | 2-pyridyl | |
| 16.321 | 1-$CH_3$-c-$C_3H_5$ | 4-pyridyl | 2-pyridyl | |
| 16.322 | C(H)=$NOCH_3$ | 4-pyridyl | 2-pyridyl | |
| 16.323 | $C(CH_3)$=$NOCH_3$ | 4-pyridyl | 2-pyridyl | |
| 16.324 | $C(C_2H_5)$=$NOCH_3$ | 4-pyridyl | 2-pyridyl | |
| 16.325 | Ph | 4-pyridyl | 2-pyridyl | |
| 16.326 | 2-Cl(Ph) | 4-pyridyl | 2-pyridyl | |
| 16.327 | 3-Cl(Ph) | 4-pyridyl | 2-pyridyl | |
| 16.328 | 4-Cl(Ph) | 4-pyridyl | 2-pyridyl | |
| 16.329 | 2-F(Ph) | 4-pyridyl | 2-pyridyl | |
| 16.330 | 3-F(Ph) | 4-pyridyl | 2-pyridyl | |
| 16.331 | 4-F(Ph) | 4-pyridyl | 2-pyridyl | |
| 16.332 | 2-$CF_3$(Ph) | 4-pyridyl | 2-pyridyl | |
| 16.333 | 3-$CF_3$(Ph) | 4-pyridyl | 2-pyridyl | |
| 16.334 | 4-$CF_3$(Ph) | 4-pyridyl | 2-pyridyl | |
| 16.335 | 2,4-Cl(Ph) | 4-pyridyl | 2-pyridyl | |
| 16.336 | 2,4-F(Ph) | 4-pyridyl | 2-pyridyl | |
| 16.337 | $CH_3$ | 2-thienyl | 3-pyridyl | |
| 16.338 | $CH_3$ | 3-thienyl | 3-pyridyl | |
| 16.339 | $CH_3$ | 2-pyridyl | 3-pyridyl | |
| 16.340 | $CH_3$ | 3-pyridyl | 3-pyridyl | |
| 16.341 | $CH_3$ | 4-pyridyl | 3-pyridyl | |
| 16.342 | $CH_3$ | pyrazinyl | 3-pyridyl | |
| 16.343 | $CH_3$ | quinolin-2-yl | 3-pyridyl | |
| 16.344 | $CH_3$ | quinolin-4-yl | 3-pyridyl | |
| 16.345 | $CH_3$ | pyrimidin-2-yl | 3-pyridyl | |
| 16.346 | $CH_3$ | pyrimidin-2-yl | 3-pyridyl | |
| 16.347 | $CH_3$ | 2-thienyl | 4-pyridyl | |
| 16.348 | $CH_3$ | 3-thienyl | 4-pyridyl | |
| 16.349 | $CH_3$ | 2-pyridyl | 4-pyridyl | |
| 16.350 | $CH_3$ | 3-pyridyl | 4-pyridyl | |
| 16.351 | $CH_3$ | 4-pyridyl | 4-pyridyl | |
| 16.352 | $CH_3$ | pyrazinyl | 4-pyridyl | |
| 16.353 | $CH_3$ | quinolin-2-yl | 4-pyridyl | |
| 16.354 | $CH_3$ | quinolin-4-yl | 4-pyridyl | |
| 16.355 | $CH_3$ | pyrimidin-2-yl | 4-pyridyl | |
| 16.356 | $CH_3$ | pyrimidin-2-yl | 4-pyridyl | |
| 16.357 | $CH_3$ | 2-thienyl | 2-thienyl | |
| 16.358 | $CH_3$ | 3-thienyl | 2-thienyl | |
| 16.359 | $CH_3$ | 2-pyridyl | 2-thienyl | |
| 16.360 | $CH_3$ | 3-pyridyl | 2-thienyl | |
| 16.361 | $CH_3$ | 4-pyridyl | 2-thienyl | |
| 16.362 | $CH_3$ | pyrazinyl | 2-thienyl | |
| 16.363 | $CH_3$ | quinolin-2-yl | 2-thienyl | |
| 16.364 | $CH_3$ | quinolin-4-yl | 2-thienyl | |
| 16.365 | $CH_3$ | pyrimidin-2-yl | 2-thienyl | |
| 16.366 | $CH_3$ | pyrimidin-2-yl | 2-thienyl | |
| 16.367 | $CH_3$ | 2-thienyl | 3-thienyl | |
| 16.368 | $CH_3$ | 3-thienyl | 3-thienyl | |
| 16.369 | $CH_3$ | 2-pyridyl | 3-thienyl | |
| 16.370 | $CH_3$ | 3-pyridyl | 3-thienyl | |
| 16.371 | $CH_3$ | 4-pyridyl | 3-thienyl | |
| 16.372 | $CH_3$ | pyrazinyl | 3-thienyl | |
| 16.373 | $CH_3$ | quinolin-2-yl | 3-thienyl | |
| 16.374 | $CH_3$ | quinolin-4-yl | 3-thienyl | |
| 16.375 | $CH_3$ | pyrimidin-2-yl | 3-thienyl | |
| 16.376 | $CH_3$ | pyrimidin-2-yl | 3-thienyl | |
| 16.377 | $CH_3$ | 2-thienyl | pyrazinyl | |
| 16.378 | $CH_3$ | 3-thienyl | pyrazinyl | |
| 16.379 | $CH_3$ | 2-pyridyl | pyrazinyl | |
| 16.380 | $CH_3$ | 3-pyridyl | pyrazinyl | |
| 16.381 | $CH_3$ | 4-pyridyl | pyrazinyl | |
| 16.382 | $CH_3$ | pyrazinyl | pyrazinyl | |
| 16.383 | $CH_3$ | quinolin-2-yl | pyrazinyl | |
| 16.384 | $CH_3$ | quinolin-4-yl | pyrazinyl | |
| 16.385 | $CH_3$ | pyrimidin-2-yl | pyrazinyl | |
| 16.386 | $CH_3$ | pyrimidin-2-yl | pyrazinyl | |
| 16.387 | $CH_3$ | 2-thienyl | quinolin-4-yl | |
| 16.388 | $CH_3$ | 3-thienyl | quinolin-4-yl | |
| 16.389 | $CH_3$ | 2-pyridyl | quinolin-4-yl | |
| 16.390 | $CH_3$ | 3-pyridyl | quinolin-4-yl | |
| 16.391 | $CH_3$ | 4-pyridyl | quinolin-4-yl | |
| 16.392 | $CH_3$ | pyrazinyl | quinolin-4-yl | |
| 16.393 | $CH_3$ | quinolin-2-yl | quinolin-4-yl | |
| 16.394 | $CH_3$ | quinolin-4-yl | quinolin-4-yl | |
| 16.395 | $CH_3$ | pyrimidin-2-yl | quinolin-4-yl | |
| 16.396 | $CH_3$ | pyrimidin-2-yl | quinolin-4-yl | |

Table 17:
Compounds 17.1 to 17.396 are compounds of Formula V (X=N and Z=O) wherein the substituents $R_2$, $R_3$, and $R_7$ are defined in Table 16.

Table 18:
Compounds 18.1 to 18.396 are compounds of Formula VII (X=N and Z=NH) wherein the substituents $R_2$, $R_3$, and $R_7$ are defined in Table 16.

As used in Tables 1 to 18 Ph is understood to be phenyl.

Scheme A describes the preparation of compounds of the Formula (I). where X is CH or N, and Z is O (compounds of formula IV and V). The cyclopropyl oximes (III) are reacted with the appropriately substituted benzyl derivatives (II) where Z is a halogen, such as bromo., chloro or iodo, preferably a benzyl bromide. A cyclopropyl substituted oxime represented by the general formula (III) is treated, at room temperature, with an appropriate base to form an anion, followed by the addition of the benzyl bromides (II). Typical bases employed are metal hydrides such as sodium hydride, alkoxides such as sodium methoxide and hydroxide bases such as sodium or potassium hydroxide and alkali bases such as sodium or potassium carbonate. Typical solvents employed with hydride bases are N,N-dimethylformamide (DMF) and tetrahydrofuran (THF); with hydroxide bases DMF, THF, methyl ethyl ketone (MEK) and acetone and with alkali bases solvents such as DMF, acetone, and MEK.

As shown in Scheme A, the N—O bond in C(R$_2$)=N—O—, appears in the E position (assuming

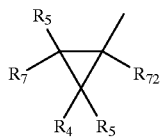

is the larger substituent), It should be recognized that the Z isomer can also be produced as well as mixtures. When isomers are produced they are designated isomer A (higher R$_1$ on thin layer chromatography) and isomer B (lower R$_1$ on thin layer chromatography). The determination of which isomer, A or B possesses the E or Z geometry can be made by such conventional techniques as X ray crystallography or by spectroscopic means such as nuclear magnetic resonance spectroscopy. For the compounds of the present invention isomer A has been assigned the E iminoxy configuration and isomer B, the Z iminoxy configuration.

Compounds of formula IV (X is CH) are prepared by alkylation with methyl E-α-(2-bromomethylphenyl)-β-methoxyacrylate in the presence of a base, preferably NaOH or KOH, in a solvent, preferably acetone or methyl ethyl ketone. Methyl E-α-(2-bromomethylphenyl)-β-methoxyacrylate, as a single E isomer, can be prepared in two steps from 2-methylphenylacetate as described previously in U.S. Pat. No. 4,914,128, columns 3–4. Compounds of formula V (X=N) are prepared by the reaction with methyl E-2-(bromomethyl)phenylglyoxylate O-methyloxime in the presence of a base, preferably NaOH or KOH, in a solvent, preferably acetone or methyl ethyl ketone. Methyl 2-(bromomethyl)phenylglyoxylate O-methyloxime can be prepared as described in U.S. Pat. No. 4,999,042, columns 17–18 and 5,157,144, columns 17–18. Methyl 2-(bromomethyl)phenylglyoxylate O-methyloxime is prepared from methyl 2-methylphenylacetate by treatment with an alkyl nitrite under basic conditions to provide after methylation, methyl 2-methyl-phenylglyoxalate O-methyl oxime which can also be prepared from methyl 2-methyl-phenylglyoxalate by treatment with 2-hydroxylamine hydrochloride and methylation or by treatment with methoxylamine hydrochloride.

Scheme A

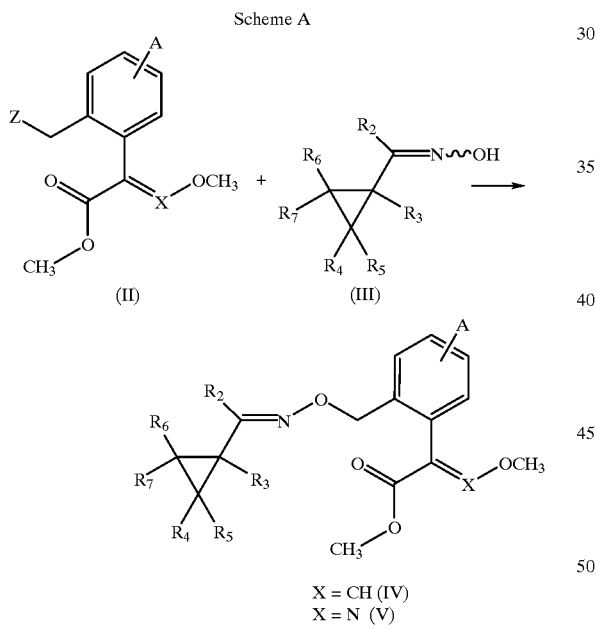

X = CH (IV)
X = N (V)

Scheme B

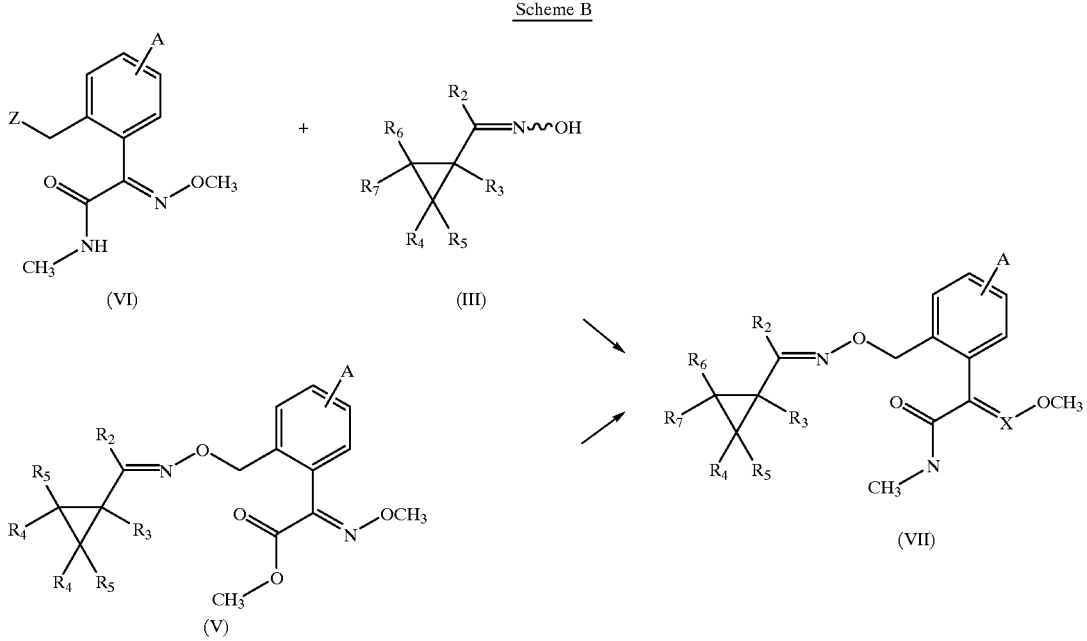

As shown in scheme B compounds of formula VII (X is N) can be prepared by the aminolysis of oximinoacetate (V). The aminolysis of oximinoacetate to oximinoacetamides has been described in U.S. Pat. No. 5,185,342, cols. 22, 48 and 57, U.S. Pat. No. 5,221,691, cols. 26–27 and U.S. Pat. No. 5,407,902, col. 8. For example, compounds of Table 2 of formula V where X is N and Z is O are treated with 40% aqueous methylamine in methanol to provide compounds of Table 3 of formula VII where Z is NH. Alternatively, as is shown in scheme B intermediate unsaturated oximes (III) are reacted with N-methyl (E)-2-methoxyimino-2-[2-(bromomethyl)phenyl]-acetamide in the presence of a base such as an hydroxide base preferably in a solvent such as acetone or methyl ethyl ketone to provide compounds of Table II of formula (VII). N-methyl (E)-2-methoxy-imino-2-[2-(bromomethyl)phenyl]acetamide is described in U.S. Pat. No. 5,387,714, col. 13.

The oximes of the general formula (III) can be obtained, as shown in scheme C, by reacting the corresponding cyclopropyl aldehyde or ketone (VIII) with hydroxylamine hydrochloride from room temperature to reflux, preferably at room temperature, in an appropriate solvent such as methanol or ethanol in the presence of an appropriate alkali such as sodium hydroxide, potassium carbonate or pyridine. A general description of the synthesis of oximes with hydroxylamine is described in March, *Advanced Organic Chemistry*, 4th Ed, pp. 906–907 and references therein. The oximes of the general formula (III) when obtained as a mixture of syn or anti oxime isomers can be separated into individual isomers and alkylated as described in scheme A and B. When a mixture of oximes of the general formula (III) are used in Scheme A and B the compounds of the formula IV, V and VII can be separated into their individual isomers by conventional chromatographic techniques.

Scheme C

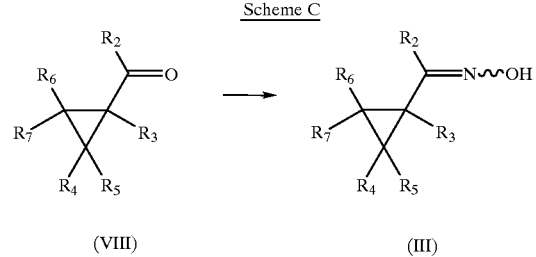

The cyclopropyl aldehydes or ketones (VIII) can be prepared by conventional techniques. The unsaturated intermediate IX (scheme D) is reacted with a sulfur ylide, prepared from a dimethylsulfoxonium salt in the presence of a base, resulting in the substituted acyl cyclopropanes, VIII. The chemistry of sulfur ylides is described in Trost and Melvin, *Sulfur Ylids*, Academic Press, New York, N.Y. 1975 and in Block, *Reactions of Organosulfur Compounds*, pp. 91–123, Academic Press, New York, N.Y. 1978. Typical reaction conditions for sulfur ylide formation from a dimethylsulfoxonium salt utilizes bases such as hydroxides, metal hydrides and alkoxides in solvents such as dimethoxyethane, dimethylsulfoxide and water depending on the base employed. The reactions are conducted from 0 to 20° C. preferably from 10–15° C. and preferably with alkali metal hydroxides in dimethylsulfoxide. Typically dimethylsulfoxonium methylide is prepared from trimethylsulfoxonium iodide in dimethylsulfoxide in the presence of powdered sodium hydroxide at room temperature. Cyclopropyl aldehydes or ketones are added dropwise to the ylide and stirred at room temperature.

Scheme D

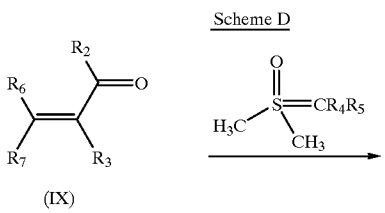

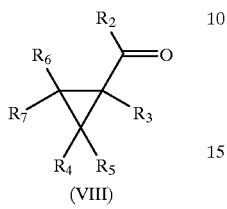

(VIII)

The oximes of the general formula (III') in which $R_2$ is $C(R_{10})=N-OR_9$; can be obtained, as shown in scheme E. The ketones, X, wherein $R_{10}$ is not H, or the aldehydes $R_{10}$ is H, are reacted with an alkyl nitrite such as t-butylnitrite or isoamylnitrite under basic conditions to provide the corresponding α-oximino cyclopropylketones XI. Typically the cyclopropyl ketone or aldehydes in a solvent such as t-butanol and the alkyl nitrite, typically t-butylnitrite, is added to a solution t-butanol containing a base such as potassium t-butoxide and is stirred at room temperature. The α-hydroxyimino cyclopropylketones XI are alkylated to the α-(substituted)oximino cyclopropylketones XII. The keto cyclopropyloxime XII are treated as in Scheme C to provide the bisoximes III'.

Scheme E

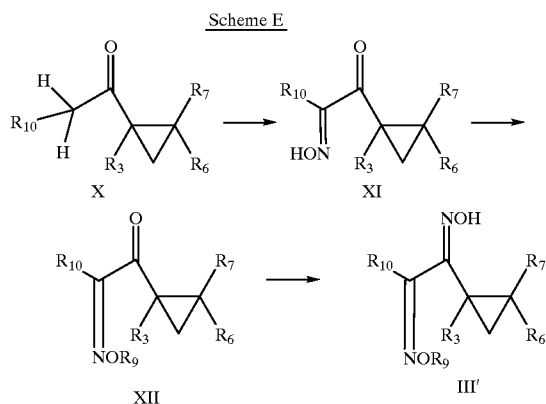

The α,β-unsaturated aldehydes or ketones IX can be prepared by conventional condensation techniques. A extensive description of the synthesis of α,β-unsaturated aldehydes or ketones (enones) is described in March, *Advanced Organic Chemistry*, 4th Ed, pp. 937–955 and references therein. For example *Organic Reactions*, Volume 16 describes the general aldol condensation of ketones and aldehydes. For intermediates of formula IX of this invention, in general the ketones or aldehydes can be $R_7COR_6$ where $R_7$ and $R_6$ are defined previously. When $R_6$ is hydrogen the aldehydes are for example substituted benzaldehydes or heterocyclic aldehydes. The ketones can be $R_2COCH_2R_3$ where $R_2$ and $R_3$ are described previously. Typically the ketone, $R_2COCH_2R_3$, is dissolved in a hydroxylic solvent, such as methanol or ethanol, to which is added dropwise the aldehyde $R_7COR_6$ followed by the base or alternatively a solution of the aldehyde in an aqueous basic solution is added. The typical bases used can be alkali metal hydroxides, such as barium, potassium or sodium hydroxide and the dropwise addition is conducted from 0° C. to 35° C. preferably at ambient temperature. When the enone is derived from acetone ($R_2$ is methyl and $R_3$ is hydrogen) the solvent is preferably acetone to which is added $R_7COR_6$ followed by the aqueous hydroxide solution.

Scheme F

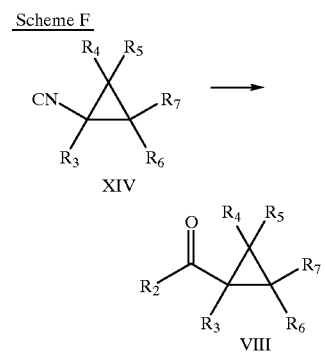

VIII

Alternatively the α,β-unsaturated cyclopropyl ketones VIII can be prepared from cyclopropyl nitriles XIV which are prepared via cyclopropanation of the acrylonitriles XIII as is described in Scheme F. The acrylonitriles XIII starting materials, shown in Scheme F can be prepared by conventional synthetic methods as described in March, Advanced Organic Chemistry, 4th Ed, pp. 937–955 and references therein. For example the nitrile derivative $R_3CH_2CN$ is condensed with the ketone or aldehyde $R_7COR_6$ in the presence of a base to provide the acrylonitriles XIII. Preferably $R_3$ in $R_3CH_2CN$ is an aryl or heteroaryl group as defined previously for $R_3$. Typically the a nitrile is dissolved in a solvent such as ethanol and water to which is added the aldehyde or ketone followed by a base. Typical bases used can be alkali metal hydroxides, such as barium, potassium or sodium hydroxide and the mixture is stirred typically at ambient temperature.

The acrylonitrile XIII is treated as is described in Scheme D with a sulfur ylide to provide the cyclopropyl nitrites XIV. The cyclopropyl nitrile XIV is transformed to the cyclopropyl ketones by organometallic addition to the nitrile followed by hydrolysis. For example the standard Grignard reagents $R_2MgX$ or organolithium reagents, $R_2Li$ add to the nitrile functionality to provide the ketones VIII'. The addition reaction to nitrites are described in March, Advanced Organic Chemistry, 4th Ed, pp.935–936 and references cited therein.

The cyclopropyl nitrile XIV can be transformed to the cyclopropyl aldehydes VIII' (where $R_2$ is H) by standard reductive methods such as with diisobutylaluminum hydride (DiBAL). The formation of aldehydes from the reduction of nitrites is described in March, Advanced Organic Chemistry, 4th Ed, pp.919–920 and references cited therein.

A direct synthesis of compounds of the formula V or VII is shown in Scheme G. Compounds of the Formula V or VII can be prepared directly from the functionalized cyclopropyl ketones or aldehydes, VIII, by condensation with the aminoxy intermediate XV. The preparation of aminoxy intermediate XV is described in U.S. Pat. No. 5194662. The aminoxy intermediate XV is prepared in a two step sequence by the alkylation of II (where X is N) with N-hydroxyphthalimide which is treated with hydrazine to provide XV. The aminoxy intermediate XV is condensed with ketones or aldehydes VIII to provide V and specifically with the cyclopropane ketones XII to provide V'. The compounds of the formula V are treated as shown in scheme B to provide VII.

Scheme G

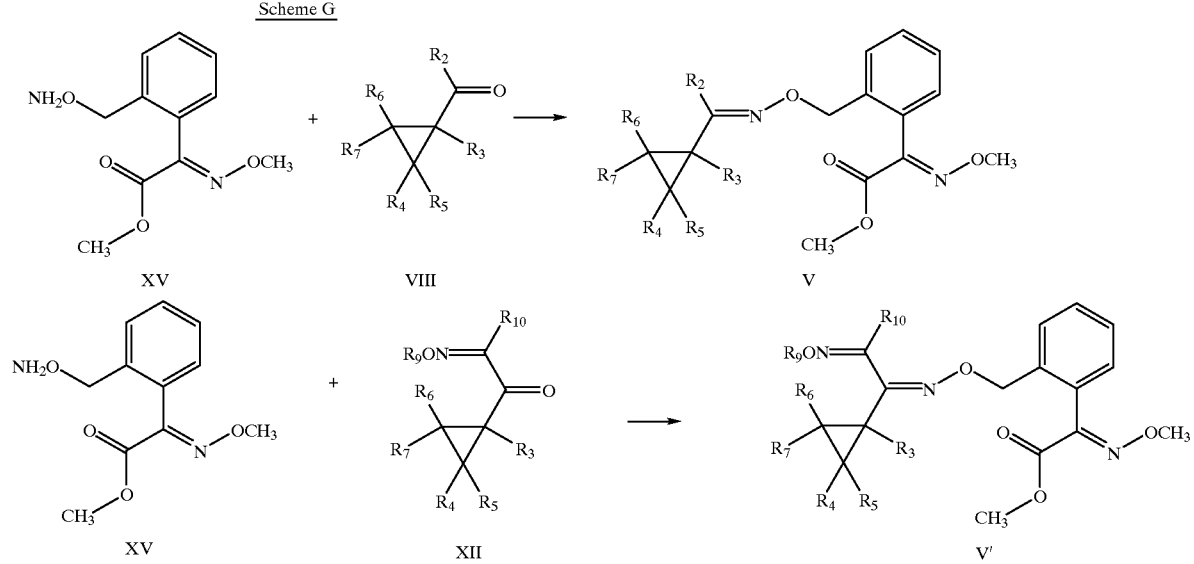

The compounds of this invention can be made according to the following procedures:

EXAMPLE 1
Preparation of Methyl (E)-3-methoxy-2-[2-((((cyclopropyl-trans-(2-(3'-chlorophenyl)cyclopropyl)methylene)amino) oxy)methyl)phenyl]propenoate Compound 1.102 of Table 1.
Preparation of trans-3-(3 '-chlorophenyl)-1-cyclopropyl-2-propen-1-one To a 250 ml round bottom flask equipped with magnetic stirrer was charged 5.0 g (0.059 moles, 1.0 eq.) of cyclopropyl methyl ketone, 50 mls of ethanol, and 50 ml of water. The 3-chlorobenzaldehyde (8.3 g, 0.059 moles, 1.0 eq.) was added in one portion, followed by 0.4 g of 85% potassium hydroxide. The flask was stoppered and stirred overnight at ambient temperature. The reaction mixture was then poured into 200 mls of water and extracted with 3×100 mls of ethyl ether. The ether extract was washed with 100 mls of saturated aqueous sodium bisulfite solution, followed by 100 mls of water, and 100 mls of saturated aqueous sodium chloride solution. The ether extract was then dried over anhydrous magnesium sulfate, filtered and concentrated on a rotary evaporator to afford 11.4 g of a yellow liquid (94% isolated yield, which was consistent with the desired product, trans-3-(3'-chlorophenyl)-1-cyclopropyl-2-propen-1-one, upon analysis by 300 Mz $^1$H NMR.

$^1$H NMR: (300 MHz, $^1$H, CDCl$_3$, TMS=0 ppm) 1.0 (m, 2H), 1.2 (m, 2H), 2.2 (m, 1H), 6.9 (d, 1H), 7.3–7.6 (m, 5H).
Preparation of trans-2-(3'-chlorophenyl) cyclopropylcyclopropyl ketone To a 500 ml round bottom flask equipped with magnetic stirrer, nitrogen inlet, and pressure equalized addition funnel was charged 12.2 g (0.0553 moles, 1.0 eq.) of trimethylsulfoxonium iodide, 2.2 g (0.0553 moles, 1.0 eq.) of powdered sodium hydroxide, and 150 mls of dimethylsulfoxide. The solution was stirred at ambient temperature for 30 minutes, followed by the dropwise addition of the trans-3-(3'-chlorophenyl)-1-cyclopropyl-2-propen-1-one in 100 mls of dimethylsulfoxide. The reaction was then stirred overnight at ambient temperature. The reaction mixture was then poured into 200 mls of water and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 9.3 g of a thick yellow liquid (76% isolated yield).which was consistent with the desired product, trans-2-(3'-chlorophenyl)cyclopropylcyclopropyl ketone upon analysis by 300 Mz $^1$H NMR.

NMR (300 MHz, $^1$H, CDCl$_3$, TMS=0 ppm) 0.9 (m, 2H), 1.1 (m, 2H), 1.3 (m, 1H), 1.7 (m, 1H), 2.1 (m, 1H), 2.3 (m, 1H), 2.6 (m, 1H), 6.9 (m, 1H), 7.1 (s, 1H), 7.2–7.3 (m, 2H)
Preparation of trans-2-(3'-chlorophenyl) cyclopropylcyclopropyl oxime To a 100 ml round bottom flask equipped with magnetic stirrer, was charged 2.0 g (0.0091 moles, 1.0 eq.) of the trans-2-(3'-chlorophenyl)cyclopropylcyclopropyl ketone 1.6 g (0.022 moles, 2.4 eq.) of hydroxylamine hydrochloride, and 50 mls of anhydrous methanol. The solution was stirred at reflux for 90 minutes, then cooled and concentrated on a rotary evaporator. The residue was dissolved in 100 mls of ethyl ether, and the ether extract was. washed with 2×50 mls of water, and 100 mls of saturated aqueous sodium chloride solution. The ether extract was dried over anhydrous magnesium sulfate, filtered and concentrated on a rotary evaporator to afford 1.4 g of a thick gummy semisolid. The crude product was chromatographed on silica gel with 50% ethyl acetate, 50% hexane. The pure fractions were combined and concentrated on a rotary evaporator to afford 0.9 g of a white solid (42% isolated yield). which was consistent with the desired product, trans-2-(3'-chlorophenyl) cyclopropylcyclopropyl oxime as an E/Z mixture of oxime isomers upon analysis by 300 Mz $^1$H NMR.

NMR (300 MHz, $^1$H, CDCl$_3$, TMS=0 ppm) 0.8 (m, 2H), 0.9 (m, 2H), 1.3 (m, 1H), 1.4–1.5 (m, 1H), 1.6 (m, 1H), 2.0 (m, 1H), 2.6–2.8 (m, 1H), 6.9 (m, 1H), 7.1 (m, 1H), 7.2–7.3 (m, 2H) 9.0 (bs, 1H).
Preparation of Methyl (E)-3-methoxy-2-[2-((((cyclopropyl-(trans-2-(3'-chlorophenyl)-cyclopropyl)methylene)amino) oxy)methyl)phenyl]propenoate To a 20 ml glass vial equipped with magnetic stirrer, was charged 0.9 g (0.00383 moles, 1.0 eq.) of trans-2-(3'- chlorophenyl)cyclopropylcyclopropyl oxime, 1.1 g (0.00383 moles, 1.0 eq.) of potassium t-butoxide, and 10 mls of anhydrous dimethylformamide. The solution was stirred at ambient temperature for 10 minutes, followed by the addition of the methyl (E)-α-[2-(bromomethyl)phenyl]-β-methoxyacrylate in one portion. The vial was then capped, and the reaction was stirred at ambient temperature overnight. The reaction mixture was then poured into 100 mls of water, and extracted with 2×50 mls of ethyl ether. The ether extract was. washed with 2×50 mls of water, and 100 mls of saturated aqueous sodium chloride solution. The ether extract was dried over anhydrous magnesium sulfate, filtered and concentrated on a rotary evaporator to afford 1.2 g of a thick red oil. The crude product was chromatographed on silica gel with 20% ethyl acetate, 80% hexane. The pure fractions were combined and concentrated on a rotary evaporator to afford 0.8 g of a clear colorless oil (45% isolated yield.) which was consistent with the desired product, as a mixture of E and Z imines methyl (E)-3-methoxy-2-[2-((((cyclopropyl-trans(2-(3'-chlorophenyl) cyclopropyl)methylene)amino)oxy)methyl)phenyl]-propenoate upon analysis by 300 Mz $^1$H NMR.

NMR (300 MHz, $^1$H, CDCl$_3$, TMS=0 ppm) 0.6–0.9 (m, 4H), 1.1 (m, 2H), 1.5 (m, 1H), 2.4 (m, 1H), 2.6 (m, 1H), 3.6–3.7 (d, 3H), 3.8–4.0 (d, 3H), 4.9–5.0 (d, 2H), 6.9 (m, 1H), 7.0 (m, 1H), 7.2–7.4 (m, 6H) 7.6 (d, 1H).

EXAMPLE 2
Preparation of E and Z imines: (E,E) and (Z,E) methyl 2-[2-((((trans-1-(2-(4'-methoxyphenyl)cycloproyl) ethylidene)amino)oxy)methyl)phenyl]-2-methoxyiminoacetate Compounds 2.23A and 2.23B of Table 2

Preparation of trans-4-(4-methoxyphenyl)-3-buten-2-one

To a 250 ml round bottom flask equipped with magnetic stirrer was charged 12.8 g (0.22 moles) of acetone, 100 mls of ethanol, and 1 ml of water. The p-anisaldehyde (3.0 g, 0.022 moles, 1.0 eq.) was added in one portion, followed by 0.2 g of barium hydroxide monohydrate (catalyst). The flask was stoppered and stirred overnight at ambient temperature. The reaction mixture was then poured into 200 mls of water and extracted with 3×100 mls of ethyl ether. The ether extract was washed with 100 mls of saturated aqueous sodium bisulfite solution, followed by 100 mls of water, and 100 mls of saturated aqueous sodium chloride solution. The ether extract was then dried over anhydrous magnesium sulfate, filtered and concentrated on a rotary evaporator to afford 3.2 g of a yellow oil (83% isolated yield) which was consistent with the desired product, trans-4-(4-methoxyphenyl)-3-buten-2-one upon analysis by 300 MHz $^1$H NMR.

NMR (300 MHz, $^1$H, CDCl$_3$, TMS=0 ppm) 2.4 (s, 3H), 3.85 (s, 3H), 6.6 (d, 1H), 6.9 (d, 2H) 7.5 (m, 3H).

Preparation of trans-2-(4'-methoxyphenyl) cyclopropylmethyl ketone

To a 250 ml round bottom flask equipped with magnetic stirrer, nitrogen inlet, and pressure equalized addition funnel was charged 4.0 g (0.0182 moles, 1.0 eq) of trimethylsulfoxonium iodide, 0.73 g (0.0182 moles, 1.0 eq) of powdered sodium hydroxide, and 100 mls of dimethylsulfoxide. The solution was stirred at ambient temperature for 30 minutes, followed by the addition of the trans-4-(4-methoxyphenyl)-3-buten-2-one in one portion. The dark red solution was then stirred for 15 minutes at ambient temperature. The reaction mixture was then poured into 200 mls of water and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 2.6 g of a thick yellow liquid (75% isolated yield) which was consistent with the desired product, trans-2-(4'-methoxyphenyl)cyclopropylmethyl ketone upon analysis by 300 MHz $^1$H NMR.

NMR (300 MHz, $^1$H, CDCl$_3$, TMS=0 ppm) 1.3 (m, 1H), 1.6 (m, 1H), 2.2 (m, 1H), 2.3 (s, 3H), 2.6 (m, 1H), 6.8 (d, 2H), 7.1 (d, 2H).

Preparation of E and Z imine isomers: (E,E) and (Z,E)-Methyl 2-[2-((((trans-1-(2-(4'-methoxyphenyl)cyclopropyl) ethylidene)amino)oxy)methyl)phenyl]-2-methoxyiminoacetate To a 25 ml glass vial equipped with magnetic stirring bar was charged the trans-2-(4'-methoxyphenyl) cyclopropylmethyl ketone (0.7 g, 0.0037 moles, 1.0 eq) 10 mls of anhydrous methanol, and 1.0 g (0.0041 moles, 1.1 eq.) of methyl (E)-2-(aminooxy-methyl)phenylglyoxylate O-methyloxime. The vial was capped, and stirred overnight at ambient temperature. The solution was then poured into 100 mls of water, and extracted with 3×100 mls of ethyl ether. The ether extract was washed with 2×100 mls of water, and 100 mls of saturated aqueous sodium chloride solution. The ether extract was then dried over anhydrous, magnesium sulfate, filtered and concentrated on a rotary evaporator to afford 1.7 g of the crude product E/Z methyl 2-[2-((((trans-1-(2-(4'-methoxyphenyl)cyclopropyl) ethylidene)amino)oxy)methyl)-phenyl]-2-methoxyiminoacetate as an amber oil. This product was chromatographed on silica gel with 30% EtOAc/70% hexane to afford, in order of elution from the column 450 mg of a viscous yellow liquid, isomer A, which was characterized as consistent with the desired product as the E imine, (E,E)-methyl-2-[2-((((trans-1-(2-(4'-methoxyphenyl) cyclopropyl)ethylidene)amino)oxy)methyl)phenyl]-2-methoxyiminoacetate upon analysis by 300 MHz $^1$H NMR, and 420 mg of a viscous yellow oil, isomer B, which was characterized as consistent with the desired product as the Z imine, (Z,E)-methyl 2-[2-((((trans-1-(2-(4'-methoxyphenyl) cyclopropyl)-ethylidene)amino)oxy)methyl)phenyl]-2-methoxyiminoacetate upon analysis by 300 MHz $^1$H NMR. 60% total yield after purification Isomer A, E imine, NMR (300 MHz, $^1$H, CDCl$_3$, TMS=0 ppm) 1.1 (m, 1H), 1.3 (m, 1H), 1.7 (m, 1H), 1.75 (s, 3H), 2.1 (m, 1H), 3.8 (s, 3H), 3.9 (s, 3H), 4.0 (s, 3H), 4.95 (s, 2H), 6.8–6.9 (m, 3H), 7.0 (d, 1H), 7.2 (m, 1H) 7.4–7.7 (m, 3H)

Isomer B, Z imine, NMR (300 MHz, $^1$H, CDCl$_3$, TMS=0 ppm) 1.1–1.4 (m, 2H), 1.6 (s, 3H), 2.2 (m, 1H), 2.6 (m, 1H), 3.75 (s, 3H), 3.8 (s, 3H), 4.0 (s, 3H), 4.95 (s, 2H), 6.8–6.9 (m, 3H), 7.0 (d, 1H), 7.2 (m, 1H) 7.4–7.7 (m, 3H)

Preparation of methyl (E)-2-(aminooxymethyl)phenyl glyoxylate O-methyloxime Methyl (E)-2-(O-phthalimidoxymethyl)phenyl glyoxylate O-methyloxime To a dry 500 ml round bottom flask equipped with magnetic stirrer, and nitrogen inlet was charged 5.1 g (0.0315 moles) of N-hydroxyphthalimide, 1.3 g (0.0315 moles) of sodium hydroxide, and 300 ml of anhydrous dimethylformamide. The dark red solution was stirred at ambient temperature for 20 min., followed by the addition of the methyl 2-(bromomethyl)phenylglyoxylate O-methyloxime (15 g, 60% pure, 0.0315 moles) in one portion. The reaction was stirred at ambient temperature over the weekend, then poured into 800 mls of water and stirred for 1 hour to afford a white solid which was collected by vacuum filtration and washed with water, hexane, and dried under vacuum at 40° C. overnight. Isolated 11.5 g of a white solid (98% isolated yield) which was consistent with the desired product, methyl (E)-2-(O-phthalimidoxymethyl)

phenyl glyoxylate O-methyloxime, upon analysis by 300 MHz $^1$H NMR.

NMR (300 MHz, $_1$H, CDCl$_3$, TMS=0 ppm) 3.8 (s, 3H), 3.95 (s, 3H), 5.0 (s, 2H), 7.1 (d, 1H), 7.5 (m, 2H), 7.7–7.9 (m, 5H).

Preparation of methyl (E)-2-(aminooxymethyl)phenyl glyoxylate O-methyloxime.

To a 250 ml round-bottom flask equipped with magnetic stirrer was charged 11.4 g (0.031 moles)of methyl (E)-2-(O-phthalimidoxymethyl)phenyl glyoxylate O-methyloxime 100 mls of anhydrous methanol, and 1.9 g (0.034 moles)of hydrazine monohydrate. The flask was stoppered, and the reaction was stirred at ambient temperature for 2 hours. The resulting solid was removed by filtration and the filtrate was concentrated on the rotary evaporator. The residue was dissolved in 100 mls of ether, filtered, and stripped to afford 7.4 g of a thick yellow oil (100% isolated yield). which was consistent with the desired product methyl (E)-2-(aminooxymethyl)phenyl glyoxylate O-methyloxime upon analysis by 300 MHz $^1$H NMR. Stored at −20° C. until needed for future synthesis.

NMR (300 MHz, 1H, CDCl$_3$, TMS=0 ppm) 3.87 (s. 3H), 4.03 (s, 3H), 4.6 (s, 2H), 4.9–5.4 (bs, 2H), 7.2 (m, 1H), 7.4–7.5 (m, 3H).

EXAMPLE 3
Preparation of E and Z imine isomers: (E,E) and (Z,E)-N-Methyl 2-[2-((((trans-1-(2-(4'-methoxyphenyl)cyclopropyl)ethylidene)amino)oxy)methyl)phenyl]-2-methoxyiminoacetamide Compounds 3.23A and 3.23B of Table 3.

To a dry 100 ml round bottom flasks equipped with magnetic stirrer was charged 210 mg (0.512 mmoles) of Compound 2.23A, E imine, (E,E)-methyl 2-[2-((((trans-1-(2-(4'-methoxyphenyl)cyclopropyl)ethylidene)amino)oxy)methyl)phenyl]-2-methoxyimino-acetate 10 mls anhydrous methanol, and 1.0 mls (12.9 mmoles) of 40% aqueous methyl amine. The flask was stoppered and stirred over the weekend at ambient temperature. The solution was then poured into 100 mls of water, and extracted with 3×50 mls of ethyl ether. The ether extract was washed with 2×100 mls of water, and 100 mls of saturated aqueous sodium chloride solution. The ether extract was then dried over anhydrous magnesium sulfate, filtered and concentrated on a rotary evaporator to afford 210 mg of a thick yellow oil (100% isolated yield) which was consistent with the desired product, (E,E)-N-methyl 2-[2-((((trans-1-(2-(4'-methoxyphenyl)cyclopropyl)ethylidene)amino)oxy)methyl)phenyl]-2-methoxyiminoacetamide upon analysis by 300 MHz $^1$H NMR.

Compound 3.23A, Isomer A, E imine, NMR (300 MHz, $^1$H, CDCl$_3$, TMS=0 ppm) 1.1 (m, 1H), 1.3 (m, 1H), 1.7 (m, 1H), 1.75 (s, 3H), 2.1 (m, 1H), 2.9 (d, 3H), 3.8 (s, 3H), 3.95 (s, 3H), 4.95 (s, 2H), 6.7 (bs, 1H), 6.8–6.9 (m, 3H), 7.0 (d, 1H), 7.2 (m, 1H) 7.4–7.7 (m, 3H)

The procedure was repeated for 0.23 g of compound 2.23B, Z imine, (Z,E)-methyl 2-[2-((((trans-1-(2-(4'-methoxyphenyl)cyclopropyl)ethylidene)amino)oxy)-methyl)phenyl]-2-methoxyiminoacetate, and gave 0.23 g of (Z,E)-2-[2-((((trans-1-(2-(4'methoxyphenyl)-cyclopropyl)ethylidene)amino)oxy)methyl)phenyl]-2-methoxyiminoacetamide, upon analysis by 300 MHz $^1$H NMR, in a 100% isolated yield.

Compound 3.23B, Isomer B, Z imine, NMR (300 MHz, $^1$H, CDCl$_3$, TMS=0 ppm) 1.1–1.4 (m, 2H), 1.6 (s, 3H), 2.2 (m, 1H), 2.7 (m, 2H), 2.75 (d, 3H), 3.8 (s, 3H), 3.95 (s, 3H), 4.95 (s, 2H), 6.6 (bs, $_1$H), 6.8–6.9 (m, 3H), 7.0 (d, 1H), 7.2 (m, 1H) 7.4–7.7 (m, 3H).

EXAMPLE 4
Preparation of E and Z imines: (E,E) and (Z,E)-Methyl 2-[2-((((trans-1-(2-phenylcyclopropyl)ethylidene)amino)oxy)methyl)phenyl]-2-methoxyiminoacetate Compounds 2.11, 2.11A and 2.11B Table 2

Preparation of trans-2-phenylcyclopropylmethyl ketone

To a 2000 ml round-bottom flask equipped with magnetic stirrer was charged the 150 g of trimethylsulfoxonium iodide (0.685 moles, 1.0 eq.), 28 g of powdered sodium hydroxide (0.685 moles, 1.0 eq.) and 1000 mls of DMSO. The flask was stoppered and stirred at ambient temperature for 15 min., after 100 g of trans-4-phenyl-3-buten-2-one (0.685 moles) was added in one portion. The reaction was stirred at ambient temperature for 5 min., then poured into 500 mls of water and extracted with 3×200 ml of ethyl ether. The ether extract was washed successively with 2×200 mls of water and 200 mls of brine, dried over anhydrous. MgSO$_4$, filtered and stripped. 94 g of a yellow liquid (86% yield.) was isolated which was consistent with the desired product trans-2-cyclopropylmethyl ketone upon analysis by 300 MHz $^1$H NMR.

300 MHz, $^1$H, CDCl$_3$, TMS=0 ppm): 1.3 (m, 1H), 1.7 (m, 1H), 2.2 (m, 1H), 2.3 (s, 3H), 2.6 (m, 1H), 7.1 (d, 2H), 7.2–7.4 (m, 3H)

Preparation of E and Z imines: (E,E) and (Z,E)-Methyl 2-[2-((((trans-1-(2-phenyl-cyclopropyl)ethylidene)amino)oxy)methyl)phenyl]-2-methoxyiminoacetate To a 250 ml round-bottom flask equipped with magnetic stirring bar and reflux condenser was charged 7.3 g of trans-2-phenylcyclopropylmethyl ketone (0.045 moles, 1.0 eq)) in 100 ml of methanol, and 16.2 g of methyl (E)-2-(aminooxymethyl)phenyl-glyoxylate O-methyloxime (0.0685, 1.52eq.). The reaction was heated to reflux for 2 hours, after which an aliquot was analyzed by capillary GC. No starting material remained, and two new products were observed in a ratio of approximately. 70%/30% The reaction was then cooled and poured into 200 mls of water, and extracted with 3×100 mls of ethyl ether. The ether extract was washed with 2×100 mls of water, 100 mls of 0.1 N HCl and 100 mls of saturated NaCl solution. The ether extract was then dried over anhydrous. NMgSO$_4$, filtered and stripped to yield 17.2 g of crude product as a thick yellow oil (quantitative yield). which was characterized by 300 MHz $^1$H NMR, and capillary GC as consistent with the (E,E) and (Z,E)-methyl 2-[2-((((trans-1-(2-phenylcyclopropyl)ethylidene)-amino)oxy)methyl)phenyl]-2-methoxyiminoacetate in a ratio of the imines (~70% E to 30% Z).

1.0 g of compound 2.11 (mixture of compounds 2.11A and 2.11B) was chromatographed on silica gel with 25% EtOAc/75% hexane to afford, in order of elution from the column 500 mg of a viscous yellow liquid, isomer A, which was characterized as consistent with the desired product as the E imine, (E,E)-methyl-2-[2-((((trans-1-(2-phenylcyclopropyl)-ethylidene)amino)oxy)methyl)phenyl]-2-methoxyiminoacetate upon analysis by 300 MHz $^1$H NMR, and 250 mg of a viscous yellow oil, isomer B, which was characterized as consistent with the desired product as the Z imine, (Z,E)-methyl 2-[2-((((trans-1-(2-phenyl)cyclopropyl)ethylidene)-amino)oxy)methyl)phenyl]-2-methoxyiminoacetate upon analysis by 300 MHz $^1$H NMR. The recovery after purification was 75% .

Compound 2.11A: Isomer A, E imine, NMR (300 MHz, $^1$H, CDCl$_3$, TMS=0 ppm) 1.2 (m, 1H), 1.4 (m, 1H), 1.75 (s, 3H), 1.8 (m, 1H), 2.2 (m, 1H), 3.8 (s, 3H), 4.0 (s, 3H), 4.95 (s, 2H), 7.1 (d, 2H), 7.2 (m, 2H), 7.3 (m, 2H), 7.4–7.5 (m, 3H).

Compound 2.11B: Isomer B, Z imine, NMR (300 MHz, $^1$H, CDCl$_3$, TMS=0 ppm) 1.2 (m, 1H), 1.3 (m, 1H), 1.65 (s, 3H), 2.2 (m, 1H), 2.7 (m, 1H), 3.7 (s, 3H), 4.0 (s, 3H), 4.95 (s, 2H), 7.1–7.2 (m, 4H), 7.3 (m, 2H), 7.4–7.5 (m, 3H)

EXAMPLE 5

Preparation of E and Z imines: (E,E) and (Z,E)-N-Methyl 2-[2-((((trans-1-(2-phenylcyclopropyl)ethylidene)amino)oxy)methyl)phenyl]-2-methoxyiminoacetamide Compounds 3.11, 3.11 A and 3.11 B of Table 3

To a dry 250 ml round-bottom flasks equipped with magnetic stirrer was charged 17.2 g of compound 2.11 as a 70:30 mixture of (E,E) and (Z,E)-methyl 2-[2-((((trans-1-(2-phenyl-cyclopropyl)ethylidene)amino)oxy)methyl)phenyl]-2-methoxyiminoacetate (0.0453 moles, 1.0 eq.) in 100 mls methanol, and 5.3 g of 40% methyl amine (0.0679 moles, 1.5eq.) in water. The flask was then stoppered and stirred overnight at ambient temperature. An aliquot was analyzed by capillary gas chromatography. No starting material remained, and two new products were observed in a ratio of approximately. 70%/30%. The reaction was then poured into 200 mls of water, and extracted with 3×100 mls of ethyl ether. The ether extract was washed with 2×100 mls of water, 100 mls of 0.1 N HCl and 100 mls of saturated NaCl solution. The ether extract was then dried over anhydrous. MgSO$_4$, filtered and stripped to yield 15.1 g of crude product as a thick yellow oil, which was characterized by 300 MHz $^1$H NMR, and capillary GC as consistent with compound 3.11 as a 70:30 iminoxy mixture of (E,E) and (Z,E)-N-methyl 2-[2-((((trans-1-(2-phenyl-cyclopropyl)ethylidene)amino)oxy)methyl)phenyl]-2-methoxyiminoacetamide in 88% isolated yield.

1.5 g of compound 3.11 was chromatographed on silica gel with 30% EtOAc/70% hexane to afford, in order of elution from the column 1100 mg of a viscous yellow liquid, isomer A, which was characterized as consistent with the desired product as the E imine, (E,E)-methyl-2-[2-((((trans-1-(2-phenylcyclopropyl)ethylidene)amino)oxy)methyl)phenyl]-2-methoxyiminoacetate upon analysis by 300 MHz $^1$H NMR, and 350 mg of a viscous yellow oil, isomer B, which was characterized as consistent with the desired product as the Z imine, (Z,E)-methyl 2-[2-((((trans-1-(2-phenylcyclopropyl)ethylidene)amino)oxy)-methyl)phenyl]-2-methoxyiminoacetate upon analysis by 300 MHz $^1$H NMR. The recovery after purification was 97%.

Compound 3.11A, Isomer A, E imine, NMR (300 MHz, $^1$H, CDCl$_3$, TMS=0 ppm) NMR (300 MHz, 1H, CDCl$_3$, TMS=0 ppm) 1.2 (m, 1H), 1.4 (m, 1H), 1.75(s, 3H), 1.8 (m, 1H), 2.2 (m, 1H), 2.9 (d, 3H), 4.0 (s, 3H), 4.95 (s, 2H), 6.7 (bs, 1H), 7.1 (d, 2H), 7.2 (m, 2H), 7.3 (m, 2H), 7.4–7.5 (m, 3H)

Compound 3.11B, Isomer B, Z imine, NMR (300 MHz, $^1$H, CDCl$_3$, TMS=0 ppm) 1.2 (m, 1H), 1.3 (m, 1H), 1.65 (s, 3H), 2.2 (m, 1H), 2.7 (m, 1H), 2.8 (d, 3H), 4.0 (s, 3H), 4.95 (s, 2H), 6.6 (bs, 1H), 7.1–7.2 (m, 4H), 7.3 (m, 2H), 7.4–7.5 (m, 3H)

EXAMPLE 6

Preparation of E and Z imines: (E,E) and (Z,E) methyl 2-[2-((((trans-1-(2-(2-thienyl)cyclopropyl)ethylidene)amino)oxy)methyl)phenyl]-2-methoxyiminoacetate Compounds 11.50A and 11.50B of Table 11

Preparation of trans-4-(2-thienyl)-3-buten-2-one

To a 250 ml round bottom flask equipped with magnetic stirrer was charged 13.4 g (0.267 moles, 1.0 eq.) of acetone, 100 mls of ethanol, and 1 ml of water. The 2-thiophenecarboxaldehyde (3.0 g, 0.0267 moles, 1.0 eq) was added in one portion, followed by 0.2 g of barium hydroxide monohydrate (catalyst). The flask was stoppered and stirred overnight at ambient temperature. The reaction mixture was then poured into 200 mls of water and extracted with 3×100 mls of ethyl ether. The ether extract was washed with 100 mls of saturated aqueous sodium bisulfite solution, followed by 100 mls of water, and 100 mls of saturated aqueous sodium chloride solution. The ether extract was then dried over anhydrous magnesium sulfate, filtered and concentrated on a rotary evaporator to afford 3.5 g of an amber oil (86% isolated yield).which was consistent with the desired product, trans-4-(2-thienyl)-3-buten-2-one, upon analysis by 300 MHz $^1$H NMR.

NMR (300 MHz, $^1$H, CDCl$_3$, TMS=0 ppm) 2.3 (s, 3H), 6.5 (d, 1H), 7.1 (m, 1H) 7.3 (m, 1H), 7.4 (m, 1H), 7.6 (d, 1H).

Preparation of trans-2-(2-thienyl)cyclopropylmethyl ketone

To a 250 ml round bottom flask equipped with magnetic stirrer, nitrogen inlet, and pressure equalized addition funnel was charged 5.1 g (0.023 moles, 1.0 eq.) of trimethylsulfoxonium iodide, 0.92 g (0.023 moles, 1.0 eq.) of powdered sodium hydroxide, and 100 mls of dimethylsulfoxide. The solution was stirred at ambient temperature for 30 minutes, followed by the addition of trans-4-(2-thienyl)-3-buten-2-one in one portion. The dark red solution was then stirred for 15 minutes at ambient temperature. The reaction mixture was then poured into 200 mls of water and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford the crude product, which was chromatographed on silica gel with 90% hexane, 10% ethyl acetate. The pure fractions were combined and concentrated on a rotary evaporator to afford 1.1 g of a thick pale yellow liquid in a 29% isolated yield which was consistent with the desired product, trans-2-(2-thienyl)cyclopropylmethyl ketone upon analysis by 300 MHz $^1$H NMR.

NMR (300 MHz, $^1$H, CDCl$_3$, TMS=0 ppm) 1.4 (ms, 1H), 1.7 (m, 1H), 2.2 (m, 1H), 2.3 (s, 3H), 2.7 (m, 1H), 6.8 (m, 1H), 6.9 (m, 1H), 7.1 (m, 1H).

Preparation of (E,E) and (Z,E)-methyl 2-[2-((((trans-1-(2-(2-thienyl)cyclopropyl)-ethylidene)amino)oxy)methyl)phenyl]-2-methoxyiminoacetate To a 25 ml -lass vial equipped with magnetic stirring bar was charged trans-2-(2-thienyl)cyclopropylmethyl ketone (0.6 g, 0.0036 moles, 1.0 eq.) 10 mls of anhydrous methanol, and 0.95 g (0.0040 moles, 1.0 eq.) of (E)-2-(aminooxymethyl)-phenylglyoxylate O-methyloxime. The vial was capped, and stirred overnight at ambient temperature. The solution was then poured into 100 mls of water, and extracted with 3×100 mls of ethyl ether. The ether extract was washed with 2×100 mls of water, and 100 mls of saturated aqueous sodium chloride solution. The ether extract was then dried over anhydrous, magnesium sulfate, filtered and concentrated on a rotary evaporator to afford 1.6 g of the crude product as an amber oil. This product was chromatographed on silica gel with 30% EtOAc/70% hexane to afford, in order of elution from the column 580 mg of a viscous yellow liquid which was characterized as consistent with the desired product as the E imine, (E,E)-methyl 2-[2-((((trans-1-(2-(2-thienyl)cyclopropyl)ethylidene)-amino)oxy)methyl)phenyl]-2-methoxyiminoacetate upon analysis by 300 MHz $^1$H NMR, and 300 mg of a viscous yellow oil which was characterized as consistent with the desired product as the Z imine, (Z,E)-methyl 2-[2-((((trans-1-(2-(2-thienyl)cyclopropyl)ethylidene)amino)-oxy)methyl)phenyl]-2-methoxyiminoacetate upon analysis by 300 MHz $^1$H NMR. 65 % total yield after purification.

Compound 11.50A, Isomer A, E imine NMR (300 MHz, $^1$H, CDCl$_3$, TMS=0 ppm) 1.11 (m, 1H), 1.3 (mn, 1H), 1.76 (s, 3H), 1.8 (mn, 1H), 2.3 (m, 1H), 3.85 (s, 3H), 4.05 (s, 3H), 4.95 (s, 2H), 6.7 (mn, 1H), 6.9 (m, 1H), 7.1 (d, 1H), 7.2 (d, 1H), 7.3–7.5 (m, 3H)

Compound 11.50B, Isomer B, Z imine NMR (300 MHz, $^1$H, CDCl$_3$, TMS=0 ppm) 1.2 (m, 1H), 1.3 (mn, 1H), 1.63 (s, 3H), 2.5 (mn, 1H), 2.7 (m,. 1H), 3.77 (s, 3H), 4.0 (s, 3H), 4.95 (s, 2H), 6.7 (m, 1H), 6.9 (m, 1H), 7.1 (d, 1H), 7.2 (d, 1H), 7.3–7.5 (m, 3H).

EXAMPLE 7

Preparation of E and Z imines: (E,E) and (Z,E)-N-Methyl 2-[2-((((trans-1-(2-(2-thienyl)cyclopropyl)ethylidene)amino)oxy)methyl)phenyl]-2-methoxyiminoacetamide Compounds 12.50A and 12.50B of Table 12

To a 25 ml glass vial equipped with magnetic stirrer was charged 200 mg (0. 544 mmoles) of 11.50A (E,E)-methyl 2-[2-((((trans-1-(2-(2-thienyl)cyclopropyl)ethylidene)-amino)oxy)methyl)phenyl] -2-methoxyiminoacetate in 10 mls anhydrous methanol, and 1.0 mls (12.9 mmoles) of 40% aqueous methyl amine. The vial was capped and stirred overnight at ambient temperature. The solution was then poured into 100 mls of water, and extracted with 3×50 mls of ethyl ether. The ether extract was washed with 2×100 mls of water, and 100 mls of saturated aqueous sodium chloride solution. The ether extract was then dried over anhydrous magnesium sulfate, filtered and concentrated on a rotary evaporator to afford 170 mg of a thick yellow oil in a 81% isolated yield which was consistent with the desired product, (E,E)-N-methyl 2-[2-((((trans-1-(2-(2-thienyl)-cyclopropyl)ethylidene)amino)oxy)methyl)phenyl]-2-methoxyiminoacetamide, upon analysis by 300 MHz $^1$H NMR.

Compound 12.50A, Isomer A, E imine NMR (300 MHz, $^1$H, CDCl$_3$, TMS=0 ppm) 1.1 (m, 1H), 1.3 (m, 1H), 1.75 (s, 3H), 1.8 (m, 1H), 2.35 (m, 1H), 2.95 (d, 3H), 3.95 (s, 3H), 4.95 (s, 2H), 6.65 (bs, 1H), 6.7 (m, 1H), 6.9 (m, 1H), 7.1 (d, 1H), 7.2 (d, 1H), 7.3–7.5 (m, 3H).

The procedure was repeated for the Z imine, (Z,E)-methyl 2-[2-((((trans-1-(2-(2-thienyl)cyclopropyl)ethylidene)amino)oxy)methyl)phenyl]-2-methoxyiminoacetate, with 150 mg and gave 150 mg of a thick yellow oil in a 100% isolated yield which was consistent with the desired product, (Z,E)-N-methyl 2-[2-((((trans-1-(2-(2-thienyl)-cyclopropyl)ethylidene)amino)oxy)methyl)phenyl]-2-methoxyiminoacetamide upon analysis by 300 MHz $^1$H NMR.

Compound 12.50B, Isomer B, Z imine NMR (300 MHz, $^1$H, CDCl$_3$, TMS=0 ppm) 1.2 (m, 1H), 1.3 (m, 1H), 1.61 (s, 3H), 2.5 (m, 1H), 2.7 (m, 1H), 2.8 (d, 3H), 3.9 (s, 3H), 4.97 (s, 2H), 6.65 (bs, 1H), 6.7 (m, 1H), 6.9 (m, 1H), 7.1 (d, 1H), 7.2 (d, 1H), 7.3–7.5 (m, 3H)

EXAMPLE 8

Preparation of (E)-Methyl 2-[2-(4-trans-(2-phenylcyclopropyl)-5-ethyl-2.7-dioxa-3,6-diazaocta-3,5-dien-1-yl)phenyl]-2-methoxyiminoacetate Compound 2.144A of Table 2

Preparation of trans-1-phenyl-1-penten-3-one

To a 250 ml round bottom flask equipped with magnetic stirrer was charged 10.0 g (0.116 moles, 1.0 eq.) of 2-pentanone, 100 mls of ethanol, and 10 mls of water. The benzaldehyde (12.3 g, 0.116 moles, 1.0 eq.) was added in one portion, followed by 0.4 g of 85% potassium hydroxide. The flask was stoppered and stirred overnight at ambient temperature. The reaction mixture was then poured into 200 mls of water and extracted with 3×100 mls of ethyl ether. The ether extract was washed with 100 mls of saturated aqueous sodium bisulfite solution, followed by 100 mls of water, and 100 mls of saturated aqueous sodium chloride solution. The ether extract was then dried over anhydrous magnesium sulfate, filtered and concentrated on a rotary evaporator to afford 15.8 g of a reddish liquid (78% isolated) which was consistent with the desired product, trans-1-phenyl-1-penten-3-one upon analysis by 300 MHz $^1$H NMR.

NMR (300 MHz $^1$H NMR, CDCl$_3$, TMS=0 ppm) 1.0 (t, 3H), 1.7 (q, 2H), 2.65 (t, 2H), 6.8 (d, 1H), 7.3–7.5 (m, 4H), 7.6 (m, 2H).

Preparation of trans-2-phenylcyclopropyl-n-propyl ketone

To a 500 ml round bottom flask equipped with magnetic stirrer, nitrogen inlet, and pressure equalized addition funnel was charged 19.4 g (0.0879 moles, 1.0 eq.) of trimethylsulfoxonium iodide, 3.5 g (0.0879 moles, 1.0 eq.) of powdered sodium hydroxide, and 150 mls of dimethylsulfoxide. The solution was stirred at ambient temperature for 30 minutes, followed by the dropwise addition of the trans-1-phenyl-1-penten-3-one, (15.3 g 0.0879 moles) in 50 mls of dimethylsulfoxide. The reaction was then stirred overnight at ambient temperature, then poured into 200 mls of water and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 14.2 g of a thick brown liquid (86% isolated yield.)which was consistent with the desired product, trans-2-phenylcyclopropyl-n-propyl ketone upon analysis by 300 MHz $^1$H NMR.

NMR (300 MHz, $^1$H NMR, CDCl$_3$, TMS=0 ppm) 0.95 (t, 3H), 1.3 (m, 1H), 1.7 (m, 3H), 2.2 (m, 1H), 2.45 (m, 1H), 2.5 (m, 2H), 7.0 (d, 1H), 7.1–7.5 (m, 4H)

Preparation of 2-hydroxyimino-1-(trans-2-phenylcyclopropyl)-1-butanone

To a 500 ml round bottom flask equipped with magnetic stirrer, nitrogen inlet, and pressure equalized addition funnel was charged 9.5 g (0.084 moles, 1.0 eq) of potassium t-butoxide, and 150 mls of t-butanol. The solution was stirred at ambient temperature for 30 minutes, followed by the rapid dropwise addition of a solution of the trans-2-phenylcyclopropyl-n-propyl ketone (14 g, 0.075 moles, 1.0 eq.), 26 g of 90% t-butylnitrite (0.231 moles, 3.08 eq.) and 100 mls of t-butanol. The reaction was then stirred overnight at ambient temperature, then poured into a 500 ml round-bottom flask and concentrated on a rotary evaporator. The residue was dissolved in 200 mls of water, acidified to pH 2 with 1 N aqueous hydrochloric acid, and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 8.4 g of a brown solid (52% isolated yield) which was consistent with the desired product, 2-hydroxyimino-1-(trans-2-phenylcyclopropyl)-1-butanone upon analysis by 300 MHz $^1$H NMR.

NMR (300 MHz, $^1$H, CDCl$_3$, TMS=0 ppm) 1.0 (t, 3H), 1.4 (m, 1H), 1.8 (m, 1H), 2.6 (m, 3H), 3.1 (m, 1H), 2.5 (m, 2H), 7.1 (d, 2H), 7.2–7.4 (m, 4H)

Preparation of 2-methoxyimino-1-(trans-2-phenylcyclopropyl)-1-butanone

To a 100 ml round bottom flask equipped with magnetic stirrer, and nitrogen inlet was charged 3.6 g (0.0166 moles, 1.0 eq.) of the 2-hydroxyimino-1-(trans-2-phenyl-cyclopropyl)-1-butanone, 2.3 g (0.0166 moles, 1.0 eq.) of potassium carbonate and 100 mls of dry dimethylformamide. The mixture was stirred at ambient temperature for 10 minutes, followed by the addition of 2.35 g (0.0166 moles), of iodomethane. The reaction was then stirred overnight at ambient temperature, then poured into 100 mls of water, and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 3.4 g of a brown oil which was chromatographed on silica gel with 15% ethyl acetate, 85% hexane. The pure fractions were combined and concentrated on a rotary evaporator to afford 2.5 g of a pale yellow oil (65% isolated yield) which was consistent with the desired product, 2-methoxyimino-1-(trans-2-phenylcyclopropyl)-1-butanone upon analysis by 300 MHz $^1$H NMR.

NMR (300 MHz, $^1$H, CDCl$_3$, TMS=0 ppm) 1.0 (t, 3H), 1.4 (m, 1H), 1.7 (m, 1H), 2.5 (q, 2H), 2.6 (m, 1H), 3.2 (m, 1H), 4.0 (s, 3H), 7.1 (d, 2H), 7.2–7.3 (m, 3H).

Preparation of 2-methoxyimino-1-(trans-2-phenylcyclopropyl)-1-butanone oxime

To a 200 ml round bottom flask equipped with magnetic stirrer, and nitrogen inlet was charged 2.3 g (0.010 moles, 1.0 eq.) of 2-methoxyimino-1-(trans-2-phenylcyclopropyl)-1-butanone 3.5 g (0.05 moles, 5.0 eq.) of hydroxylamine hydrochloride. 4 g (0.05 moles) of pyridine and 70 mls of methanol. The reaction was then stirred overnight at ambient temperature, then poured into 200 mls of water, and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 1.9 g of a yellow oil which was chromatographed on silica gel with 15% ethyl acetate, 85% hexane. The pure fractions were combined and concentrated on a rotary evaporator to afford (in order of elution) 1.1 g of a pale yellow solid which was consistent with the desired product, isomer A: 2-methoxyimino-1-(trans-2-phenylcyclopropyl)-1-butanone oxime upon analysis by 300 MHz $^1$H NMR, and 0.25 g of a yellow solid which was consistent with the desired product, isomer B: 2-methoxyimino-1-(trans-2-phenylcyclopropyl)-1-butanone oxime upon analysis by 300 MHz $^1$H NMR, in a 57% combined isolated yield.

Isomer A: NMR (300 MHz, $^1$H, CDCl$_3$, TMS=0 ppm) 1.0 (t, 3H), 1.3 (m, 1H), 1.9 (m, 1H), 2.5 (m, 1H), 2.6 (q, 2H), 2.8 (m, 1H), 3.95 (s, 3H), 7.1–7.4 (m, 5H), 8.5 (bs, 1H).

Isomer B: NMR (300 MHz, $^1$H, CDCl$_3$, TMS=0 ppm) 1.0 (t, 3H), 1.2 (m, 1H), 1.6 (m, 1H), 1.95(m, 1H), 2.4 (m, 1H), 2.7 (q, 2H), 3.95 (s, 3H), 7.1–7.4 (m, 5H), 9.5 (bs, 1H).

Preparation of Isomer A of (E)-Methyl 2-[2-(4-trans-(2-phenylcyclopropyl)-5-ethyl-2,7-dioxa-3,6-diazaocta-3,5-dien-1-yl)phenyl]-2-methoxyiminoacetate To a 100 ml round bottom flask equipped with magnetic stirrer, and nitrogen inlet was charged 0.8 g (0.00325 moles, 1.0 eq.) of the isomer A oxime, 2-methoxyimino-1-(trans-2-phenylcyclopropyl)-1-butanone oxime, 0.9 g (0.0065 moles, 2.0 eq.) of potassium carbonate, and 100 mls of dry dimethylformamide. The mixture was stirred at ambient temperature for 10 minutes, followed by the addition of 1.25 g (0.00325 mole, 1/0 eq.) of 75% pure methyl 2-(bromomethyl)phenylglyoxylate O-methyloxime. The reaction was then stirred overnight at ambient temperature, then poured into 100 mls of water, and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 1.4 g of a brown oil which was chromatographed on silica gel with 15% ethyl acetate, 85% hexane. The pure fractions were combined and concentrated on a rotary evaporator to afford 0.4 g of a clear colorless oil (27% isolated yield) which was consistent with the desired product, isomer A, (E)-methyl 2-[2-(4-trans-(2-phenylcyclopropyl)-5-ethyl-2,7-dioxa-3,6-diazaocta-3,5-dien-1-yl)phenyl]-2-methoxyimino-acetate upon analysis by 300 MHz $^1$H NMR.

NMR (300 MHz, $^1$H, CDCl$_3$, TMS=0 ppm) 1.0 (t, 3H), 1.3 (m, 1H), 1.8 (m, 1H), 2.4(m, 1H), 2.5 (q, 2H), 2.8 (m, 1H), 3.75 (s, 3H), 3.9 (s, 3H), 4.0 (s, 3H), 5.0 (s, 2H), 7.1 (m, 4H), 7.2 (m, 2H), 7.4 (m, 3H).

EXAMPLE 9

Preparation of (E)-N-Methyl 2-[2-(4-trans-(2-phenylcyclopropyl)-5-ethyl-2,7-dioxa-3,6-diazaocta-3,5-dien-1-yl)phenyl]-2-methoxyiminoacetamide Compound 3.144A of Table 3

To a 100 ml round bottom flask equipped with magnetic stirrer was charged 250 mg (0.55 mmoles) of isomer A of (E)-methyl2-[2-(4-trans-(2-phenylcyclopropyl)-5-ethyl-2,7-dioxa-3,6-diazaocta-3,5-dien-1-yl)phenyl]-2-methoxyiminoacetate and 50 mls of methanol. 1.0 mls of a 40% aqueous solution of methyl amine (12.9 mmoles) was then added in one portion, and the flask was stoppered, and stirred overnight at ambient temperature. The reaction was then poured into 100 mls of water, and extracted with 3×50 mls of ethyl ether. The ether extract was washed with 2×50 mls of water, and 100 mls of saturated aqueous sodium chloride solution. The ether extract was dried over anhydrous magnesium sulfate, filtered and concentrated on a rotary evaporator to afford 140 mg of a clear pale yellow oil (56% isolated yield) which was consistent with the title compound 3.144 upon analysis by 300 MHz $^1$H NMR.

NMR (300 MHz, $^1$H, CDCl$_3$, TMS=0 ppm) 0.95 (t, 3H), 1.2 (m, 1H), 1.8 (m, 1H), 2.3(m, 1H), 2.45 (q, 2H), 2.8 (m, 1H), 2.9 (d, 3H), 3.65 (s, 6H), 5.0 (s, 2H), 6.6 (bs, 1H), 7.0 (m, 4H), 7.2 (m, 2H), 7.4 (m, 3H).

EXAMPLE 10

Preparation of (E)-Methyl 2-[2-((((1-(1,2-diphenylcyclopropyl)ethylidene)-amino)oxy)methyl)phenyl]-2-methoxyiminoacetate Compounds 5.39 of Table 5

Preparation of α-phenylcinnamonitrile

To a 250 ml round bottom flask equipped with magnetic stirrer was charged 3.0 g (0.0256 moles, 1.0 eq.) of benzylcyanide, 150 mls of ethanol, and 50 mls of water. Benzaldehyde (2.7 g, 0.0256 moles, 1.0 eq.) was added in one portion, followed by 0.2 g of 85% potassium hydroxide. The flask was stoppered and stirred overnight at ambient temperature. The reaction mixture was then poured into 200 mls of water. The resulting precipitate was collected by vacuum filtration, washed with water, hexane, and dried in vacuuo at 40° C. overnight to afford 4.4 g of a white solid (84% isolated yield) which was consistent with the desired product, α-phenylcinnamonitrile, upon analysis by 300 MHz $^1$H NMR.

NMR (300 MHz, $^1$H, CDCl$_3$, TMS=0 ppm) 7.1 (s, 1H), 7.2–7.4 (m, 6H). 7.6 (d. 2H), 7.8 (m, 2H).

Preparation of 1.2-diphenylcyclopropanecarbonitrile

To a 250 ml round bottom flask equipped with magnetic stirrer, nitrogen inlet, and pressure equalized addition funnel was charged 4.8 g (0.0215 moles, 1.0 eq.) of trimethylsulfoxonium iodide, 0.86 g (0.0215 moles, 1.0 eq.) of powdered sodium hydroxide, and 150 mls of dimethylsulfoxide. The solution was stirred at ambient temperature for 30 minutes, followed by the dropwise addition of α-phenylcinnamonitrile in 100 mls of dimethylsulfoxide. The reaction was then stirred overnight at ambient temperature. The reaction mixture was then poured into 200 mls of water and extracted with 3×100 mls of ethyl ether. The ether extract was washed with 2×100 mls of water, and 100 mls of saturated aqueous sodium chloride solution. The ether extract was dried over anhydrous magnesium sulfate, filtered and concentrated on a rotary evaporator to afford 4.1 g of a thick clear colorless liquid which crystallized upon standing (87% isolated yield) and was consistent with the desired product, 1,2-diphenylcyclopropanecarbonitrile, upon analysis by 300 MHz $^1$H NMR.

NMR (300 MHz, $^1$H, CDCl$_3$, TMS=0 ppm) 2.0 (m, 1H), 2.2 (m, 1H), 2.8 (m, 1H), 7.1 (m, 10H).

Preparation of 1,2-diphenylcyclopropylmethyl ketone

To a dry 500 ml round bottom flask equipped with magnetic stirrer, nitrogen inlet, reflux condenser, and side arm addition funnel was charged 1.5 g (0.00685 moles, 1.0 eq.) of the nitrile 1,2-diphenylcyclopropanecarbonitrile and 150 ml of anhydrous toluene. The methylmagnesium bromide (0.0137 moles, 2.0 eq. 4.6 mls of 3.0 M solution in ether) was then added dropwise, and the reaction was refluxed for two hours. The reaction was cooled and carefully quenched with 100 mls of saturated aqueous ammonium chloride solution, then extracted with 3×100 mls of ethyl ether. The ether extract was washed with 2×100 mls of water and 100 mls of saturated aqueous sodium chloride solution, then dried over anhydrous magnesium sulfate, filtered, and concentrated on a rotary evaporator to afford 1.4 g of a thick clear yellow oil (87% isolated yield) which was consistent with the desired product, 1,2-diphenylcyclopropylmethyl ketone upon analysis by 300 MHz $^1$H NMR.

NMR 300 MHz, $^1$H, CDCl$_3$, TMS=0 ppm) 0.9–1.1 (m, 2H), 1.4 (m, 1H), 1.9 (s, 3H), 7.1–7.4 (m, 10H).

Preparation of (E)-Methyl 2-[2-((((1-(1,2-diphenylcyclopropyl)ethylidene)amino)-oxy)methyl)phenyl]-2-methoxyiminoacetate To a 50 ml round bottom flask equipped with magnetic stirrer and reflux condenser was charged the 0.8 g (0.0034 moles, 1.0 eq.) of 1,2-diphenylcyclopropylmethyl ketone 50 mls of anhydrous toluene, approximately 20 4A molecular sieves, and 0.9 g (0.0037 moles, 1.1 eq.) of (E)-2-(aminooxymethyl)phenylglyoxylate O-methyloxime. The reaction was refluxed for a total of 2.5 hours, then cooled, and filtered through filter paper to remove the insoluble material. The filtrate was poured into 100 mls of water and extracted with 3×50 mls of ether. The ether extract was then washed with 2×100 mls of water, 100 mls of saturated aqueous sodium chloride solution, dried over anhydrous magnesium sulfate, filtered, and concentrated on a rotary evaporator to afford 1.4 g of a thick amber liquid which was chromatographed on silica gel with 20% ethyl acetate, 80% hexane. The pure fractions were combined and concentrated on a rotary evaporator to afford 460 mg of a thick clear colorless oil (30% isolated yield) consistent with the desired product, (E)-Methyl 2-[2-((((1-(1,2-diphenylcyclopropyl)ethylidene)amino)-oxy)methyl)phenyl]-2-methoxyiminoacetate upon analysis by 300 MHz $^1$H NMR.

NMR (300 MHz, $^1$H, CDCl$_3$, TMS=0 ppm) 1.3 (s, 3H), 1.35 (m, 1H), 2.2 (m, 1H), 2.8 (m, 1H), 3.75 (s, 3H), 4.0 (s, 3H), 5.0 (s, 2H), 7.1–7.4 (m, 14H).

EXAMPLE 11

Preparation of (E)-N-Methyl 2-[2-((((1-(1,2-diphenylcyclopropyl)ethylidene)-amino)oxy)methyl)phenyl]-2-methoxyiminoacetamide Compounds 6.39 of Table 6

To a dry 100 ml round bottom flask equipped with magnetic stirrer was charged 300 mg (0.66 mmoles) of (E)-methyl 2-[2-((((1-(1,2-diphenylcyclopropyl)-ethylidene)amino)oxy)methyl)phenyl]-2-methoxyiminoacetate, 10 mls of methanol, and 1.0 ml (12.9 mmoles) of 40% aqueous methyl amine. The flask was stoppered and stirred overnight at ambient temperature. The reaction was then poured into 100 mls of water and extracted with 3×50 mls of ethyl ether. The ether extract was washed with 2×50 mls of water, and 50 mls of saturated aqueous sodium chloride solution, dried over anhydrous magnesium sulfate, filtered, and concentrated on a rotary evaporator to afford 300 mg of a thick clear yellow oil (99% isolated yield)consistent with the desired product, (E)-N-methyl 2-[2-((((1-(1,2-diphenylcyclopropyl)ethylidene)amino)oxy)methyl)phenyl]-2-methoxyiminoacetamide upon analysis by 300 MHz $^1$H NMR.

NMR (300 MHz, $^1$H, CDCl$_3$, TMS=0 ppm) 1.26 (s, 3H), 1.3 (m, 1H), 2.2 (m, 1H), 2.7 (d, 3H), 2.8 (m, 1H), 3.95 (s, 3H), 5.0 (s, 2H), 6.5 (bs, 1H), 7.1–7.4 (m, 14H).

Proton NMR data (300 MHz) are provided in Table 19 for typical examples of Tables 1 to 18 and are illustrative of the present invention.

TABLE 19

| Cmpd # | NMR DATA |
|---|---|
| 1.22A | 1.1–1.2(m, 1H), 1.3–1.4(m, 1H), 1.79(s, 3H), 1.8(m, 1H), 2.1–2.2(m, 1H), 3.67(s, 3H), 3.78(s, 3H), 3.79(s, 3H), 4.98(s, 2H), 6.6–6.75(m, 3H), 7.1–7.45(m, 5H), 7.56(s, 1H) |
| 1.22B | 1.15–1.3(m, 2H), 1.6(s, 3H), 2.1–2.2(m, 1H), 2.6–2.7(m, 1H), 3.55(s, 3H), 3.66(s, 3H), 3.69(s, 3H), 4.92(s, 2H), 6.6(t, 3H), 7.0–7.4(m, 5H), 7.46(m, 1H) |
| 1.157 | 1.2–1.4(m, 2H), 2.1(m, 1H), 2.35(m, 1H), 3.62–3.63(d, 3H), 3.7–3.74(d, 3H), 5–5.14(d, 2H), 7–7.6(m, 14H) |
| 2.01A | 1.3(m, 2H), 1.8(m, 1H), 2.2(m, 1H), 3.8(s, 3H), 4.0(s, 3H), 4.95(s, 2H), 7.05(t, 3H), 7.2(d, 2H), 7.3(m, 2H), 7.4–7.55(m, 3H) |
| 2.01B | 1.2(m, 1H), 1.4(m, 1H), 2.2(m, 1H), 2.5(m, 1H), 3.7(s, 3H), 3.9(s, 3H), 4.9(s, 2H), 7.05(m, 3H), 7.2(m, 2H), 7.3(m, 2H), 7.4–7.55(m, 3H) |
| 2.11A | 1.2(m, 1H), 1.4(m, 1H), 1.75(s, 3H), 1.8(m, 1H), 2.2(m, 1H), 3.8(s, 3H), 4.0(s, 3H), 4.95(s, 2H), 7.1(d, 2H), 7.2(m, 2H), 7.3(m, 2H), 7.4–7.5(m, 3H) |
| 2.11B | 1.2(m, 1H), 1.3(m, 1H), 1.65(s, 3H), 2.2(m, 1H), 2.7(m, 1H), 3.7(s, 3H), 4.0(s, 3H), 4.95(s, 2H), 7.1–7.2(m, 4H), 7.3(m, 2H), 7.4–7.5(m, 3H) |
| 2.12A | 1.1(m, 1H), 1.4(m, 1H), 1.7(m, 1H), 1.8(s, 3H), 2.5(m, 1H), 3.85(s, 3H), 4.0(s, 3H), 4.95(s, 2H), 6.9(d, 1H). 7.2(m, 3H), 7.4–7.6(m, 4H) |

TABLE 19-continued

| Cmpd # | NMR DATA |
|---|---|
| 2.12B | 1.1–1.4(m, 2H), 1.7(s, 3H), 2.0(m, 1H), 2.65(m, 1H), 3.75(s, 3H), 3.95 (s, 3H), 4.95(s, 2H), 6.9(d, 1H). 7.2(m, 3H), 7.4–7.6(m, 4H) |
| 2.14A | 1.05–1.2(m, 2H), 1.35(m, 1H), 1.75(s, 3H), 2.1(m, 1H), 3.83(s, 3H), 4.03(s, 3H), 4.95(s, 2H), 6.98–7.01(d, 2H), 7.1–7.2(m, 3H), 7.3–7.5(m, 3H) |
| 2.14B | 1.1–1.35(m, 2H), 1.64(s, 3H), 2.1–2.2(m, 1H), 2.5–2.6(m, 1H), 3.74(s, 3H), 3.98(s, 3H), 4.94(s, 2H), 7–7.1(d, 2H), 7.15–7.5(m, 6H) |
| 2.20A | 1.1(m, 1H), 1.4(m, 1H), 1.7(m, 1H), 1.8(s, 3H), 2.1(m, 1H), 3.8(s, 3H), 4.1(s, 3H), 5.0(s, 2H), 6.8–7.1(m, 4H), 7.2(d, 1H), 7.4–7.8(m, 3H) |
| 2.20B | 1.1–1.4(m, 2H), 1.7(s, 3H), 2.2(m, 1H), 2.6(m, 1H), 3.7(s, 3H), 3.9(s, 3H), 4.9(s, 2H), 6.9(t, 2H), 7.1(m, 2H), 7.2(m, 1H), 7.4–7.5(m, 3H) |
| 2.22A | 1.2(m, 1H), 1.4(m, 1H), 1.7(s, 3H), 1.75(m, 1H), 2.1(m, 1H), 3.8(s, 3H), 3.85(s, 3H), 4.0(s, 3H), 4.95(s, 2H), 6.6–6.8(m, 3H). 7.2(m, 2H), 7.4–7.6 (m, 3H) |
| 2.22B | 1.2–1.4(m, 2H), 1.65(s, 3H), 2.2(m, 1H), 2.6(m, 1H), 3.7(s, 3H), 3.75(s, 3H), 4.0(s, 3H), 4.95(s, 2H), 6.6–6.8(m, 3H). 7.2(m, 2H), 7.4–7.6(m, 3H) |
| 2.144A | 1.0(t, 3H), 1.3(m, 1H), 1.8(m, 1H), 2.4(m, 1H), 2.5(q, 2H), 2.8(m, 1H), 3.75(s, 3H), 3.9(s, 3H), 4.0(s, 3H), 5.0(s, 2H), 7.1(m, 4H), 7.2(m, 2H), 7.4(m, 3H) |
| 3.01A | 1.25(m, 2H), 1.7(m, 1H), 2.1(m, 1H), 2.8(d, 3H), 3.9(s, 3H), 4.85(s, 2H), 6.6(bs, 1H), 7.05(t, 3H), 7.2(d, 2H), 7.3(m, 2H), 7.4–7.55(m, 3H) |
| 3.01B | 1.2(m, 1H), 1.4(m, 1H), 2.2(m, 1H), 2.5(m, 1H), 2.75(d, 3H), 3.95(s, 3H), 5.0(s, 2H), 6.6(bs, 1H), 7.1(m, 3H), 7.2(m, 2H), 7.3(m, 2H), 7.4–7.55(m, 3H) |
| 3.11A | 1.2(m, 1H), 1.4(m, 1H), 1.75(s, 3H), 1.8(m, 1H), 2.2(m, 1H), 2.9(d, 3H), 4.0(s, 3H), 4.95(s, 2H), 6.7(bs, 1H), 7.1(d, 2H), 7.2(m, 2H), 7.3 (m, 2H), 7.4–7.5(m, 3H) |
| 3.11B | 1.2(m, 1H), 1.3(m, 1H), 1.65(s, 3H), 2.2(m, 1H), 2.7(m, 1H), 2.8(d, 3H), 4.0(s, 3H), 4.95(s, 2H), 6.6(bs, 1H), 7.1–7.2(m, 4H), 7.3(m, 2H), 7.4–7.5(m, 3H) |
| 3.12A | 1.2(m, 1H), 1.4(m, 1H), 1.7(m, 1H), 1.8(s, 3H), 2.4(m, 1H), 2.9(d, 3H), 3.95(s, 3H), 4.95(s, 2H), 6.7(bs, 1H), 6.9(d, 1H). 7.2(m, 3H), 7.4–7.6(m, 4H) |
| 3.12B | 1.1–1.4(m, 2H), 1.7(s, 3H), 1.9(m, 1H), 2.65(m, 1H), 2.85(d, 3H), 3.95 (s, 3H), 4.95(s, 2H), 6.7(bs, 1H), 6.9(d, 1H). 7.2(m, 3H), 7.4–7.6(m, 4H) |
| 3.14A | 0.95–1.1(m, 1H), 1.2–1.3(m, 1H), 1.6–1.75(m, 4H), 1.95–2.05(m, 1H), 2.81–2.83(d, 3H), 3.87(s, 3H), 4.87(s, 2H), 6.55–6.7(bs, 1H), 6.91–6.94 (d, 2H), 7.05–7.45(m, 6H) |
| 3.14B | 1.1–1.3(m, 2H), 1.56(s, 3H), 2.05–2.15(m, 1H), 2.45–2.55(m, 1H), 2.73–2.75(d, 3H), 3.83(s, 3H), 4.87(s, 2H), 6.55–6.7(bs, 1H), 6.96–6.99(d, 2H), 7.1–7.45(m, 6H) |
| 3.20A | 1.1(m, 1H), 1.4(m, 1H), 1.6(m, 1H), 1.7(s, 3H), 2.1(m, 1H), 2.8(d, 3H), 3.9(s, 3H), 4.9(s, 2H), 6.7(bs, 1H). 6.8–7.2(m, 4H), 7.2(d, 1H), 7.4–7.7(m, 3H) |
| 3.22A | 1.1(m, 1H), 1.4(m, 1H), 1.7(s, 3H), 1.75(m, 1H), 2.1(m, 1H), 2.8(d, 3H), 3.8(s, 3H), 3.95(s, 3H), 4.95(s, 2H), 6.6–6.8(m, 4H). 7.2(m, 2H), 7.4–7.6(m, 3H) |
| 3.22B | 1.1–1.4(m, 2H), 1.65(s, 3H), 2.2(m, 1H), 2.65(m, 1H), 2.8(d, 2H), 3.8(s, 3H), 3.95(s, 3H), 4.95(s, 2H), 6.6–6.8(m, 4H). 7.2(m, 2H), 7.4–7.6(m, 3H) |
| 3.28A | 1.05–1.1(m, 1H), 1.3–1.4(m, 1H), 1.69(s, 3H), 1.7–1.75(m, 1H), 2.1–2.2 (m, 1H), 2.81.2.83(d, 3H), 3.88(s, 3H), 4.87(s, 2H), 6.55–6.7(bs, 1H), 7.05–7.5(m, 8H) |
| 3.28B | 1.1–1.35(m, 2H), 1.58(s, 3H), 2.1–2.2(m, 1H), 2.5–2.6(m, 1H), 2.73–2.74 (d, 3H), 3.82(s, 3H), 4.88(s, 2H), 6.5–6.65(bs, 1H), 7.05–7.45(m, 8H) |
| 3.144 | 0.95(t, 3H), 1.2(m, 1H), 1.8(m, 1H), 2.3(m, 1H), 2.45(q, 2H), 2.8(m, 1H), 2.9(d, 3H), 3.65(s, 6H), 5.0(s, 2H), 6.6(bs, 1H), 7.0(m, 4H), 7.2 (m, 2H), 7.4(m, 3H) |
| 5.01 | 1.6(m, 1H), 1.95(m, 1H), 2.8(m, 1H), 3.70(s, 3H), 3.95(s, 3H), 4.77(s, 2H), 7.1–7.6(m, 15H) |
| 5.39 | 1.28(s, 3H), 1.3(m, 1H), 2.25(m, 1H), 2.8(m, 1H), 3.75(s, 3H), 4.0(s, 3H), 4.95(s, 2H), 7.0–7.5(m, 12H) |
| 6.01 | 1.55(m, 1H), 2.0(m, 1H), 2.75(s, 3H), 2.8(m, 1H), 3.85(s, 3H), 4.75(s, 2H), 6.4(bs, 1H), 7.1–7.6(m, 15H) |
| 6.39 | 1.26(s, 3H), 1.3(m, 1H), 2.2(m, 1H), 2.7(d, 3H), 2.8(m, 1H), 3.95(s, 3H), 5.0(s, 2H), 6.5(bs, 1H), 7.1–7.4(m, 14H) |
| 11.50A | 1.1(m, 1H), 1.3(m, 1H), 1.76(s, 3H), 1.8(m, 1H), 2.3(m, 1H), 3.85(s, 3H), 4.05(s, 3H), 4.95(s, 2H), 6.7(m, 1H), 6.9(m, 1H), 7.1(d, 1H), 7.2 (d, 1H), 7.3–7.5(m, 3H) |
| 11.50B | 1.2(m, 1H), 1.3(m, 1H), 1.63(s, 3H), 2.5(m, 1H), 2.7(m, 1H), 3.77(s, 3H), 4.0(s, 3H), 4.95(s, 2H), 6.7(m, 1H), 6.9(m, 1H), 7.1(d, 1H), 7.2(d, 1H), 7.3–7.5(m, 3H) |
| 11.121A | 1.2(m, 1H), 1.5(m, 1H), 1.77(s, 3H), 1.8(m, 1H), 2.2(m, 1H), 3.85(s, 3H), 4.03(s, 3H), 4.96(m, 2H), 7.2(m, 2H), 7.3–7.5(m, 4H), 8.4(m, 2H) |
| 11.121B | 1.3(m, 1H), 1.4(m, 1H), 1.66(s, 3H), 2.2(m, 1H), 2.7(m, 1H), 3.75(s, 3H), 4.0(s, 3H), 4.95(m, 2H), 7.2(m, 2H), 7.3–7.5(m, 4H), 8.45(m, 2H) |
| 12.50A | 1.1(m, 1H), 1.3(m, 1H), 1.75(s, 3H), 1.8(m, 1H), 2.35(m, 1H), 2.95(d, 3H), 3.95(s, 3H), 4.95(s, 2H), 6.65(bs, 1H), 6.7(m, 1H), 6.9(m, 1H), 7.1 (d, 1H), 7.2(d, 1H), 7.3–7.5(m, 3H) |
| 12.50B | 1.2(m, 1H), 1.3(m, 1H), 1.61(s, 3H), 2.5(m, 1H), 2.7(m, 1H), 2.8(d, 3H), 3.9(s, 3H), 4.97(s, 2H), 6.65(bs, 1H), 6.7(m, 1H), 6.9(m, 1H), 7.1 (d, 1H), 7.2(d, 1H), 7.3–7.5(m, 3H) |

EXAMPLE 12

Numerous compounds of this invention were tested for fungicidal activity in vivo against the diseases described below. The compounds were dissolved in a 1:1 mixture of acetone and methanol 2:1:1 or N,N-dimethylformamide and diluted with a 2:1:1 mixture of water, acetone and methanol (by volume) to achieve the appropriate concentration. The solution was sprayed onto the plants and allowed to dry for two hours. Then the plants were inoculated with fungal spores. Each test utilized control plants which were sprayed with the appropriate solvent and inoculated. For these protective tests, the plants were inoculated one day after treating the plants with the compounds of this invention. The remainder of the technique of each of the tests is given below along with the results for various compounds described herein by the Compound # against the various fungi at a dose of 100 or 150 grams per hectare. The results are percent disease control as compared to the untreated check wherein one hundred was rated as complete disease control and zero as no disease control. The application of the test fungal spores to the test plants was as follows:

Wheat Leaf Rust (WLR) *Puccinia recondita* (f. sp. *tritici*) was cultured on 7-day old wheat (cultivar Fielder) over a 12-day period in the greenhouse. Spores were collected from the leaves by settling on aluminum foil. The spores were cleaned by sieving through a 250-micron opening screen and stored dry. The dried spores were used within one month. A spore suspension was prepared from dry uredia by adding 20 mg (9.5 million spores) per ml of Soltrol oil. The suspension was dispensed into gelatin capsules (0.7 ml capacity) which attach to the oil atomizers. One capsule is used per flat of twenty 2-inch square pots of 7-day old plants, cultivar Fielder. After waiting for at least 15 minutes for the oil to evaporate from the wheat leaves, the plants were placed in a dark mist chamber (18–20° C. and 100% relative humidity) for 24 hours. The plants were then placed in the greenhouse and evaluated after 12 days for disease.

Wheat Leaf Blotch (SNW)

Cultures of *Septoria nodorum* was maintained on Czapek-Dox V-8 juice agar plates in an incubator at 20° C. with alternating periods of 12 hours of light and 12 hours of darkness for 2 weeks. A water suspension of the spores was obtained by shaking the portion of the plate with fungal material in deionized water and filtering through cheesecloth. The spore-containing water suspension was diluted to a spore concentration of $3.0\times10^6$ spores per ml. The inoculum was dispersed by a DeVilbiss atomizer over one-week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

*Erysiphe graminis* (f. sp. *tritici*) was cultured on wheat seedlings, cultivar Fielder, in a controlled temperature room at 18° C. Mildew spores were shaken from the culture plants onto 7-day old wheat seedlings which had been previously sprayed with the fungicide compound. The inoculated seedlings were kept in a controlled temperature room at 18° C. and subirrigated. The percent disease control was rated 7 days after the inoculation. Disease control values were recorded as percent control.

Cucumber Powdery Mildew (CPM)

*Sphaerotheca fulginea* was maintained on cucumber plants, cultivar Bush Champion, in the greenhouse. Inoculum was prepared by placing five to ten heavily mildewed leaves in a glass jar with 500 ml of water containing 1 drop of Tween 80 (polyoxyethylene monooleate) per 100 ml. After shaking the liquid and leaves, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Tomato Late Blight (TLB)

Cultures of *Phytophthora infestans* were maintained on green pea-amended agar for two to three weeks. The spores were washed from the agar with water and dispersed with a DeVilbiss atomizer over the leaves of 3-week old Pixie tomato plants which had been previously treated with compound of the present invention. The inoculated plants were placed in a humidity cabinet at 20° C. for 24 hours for infection. The plants were then removed to a controlled environment room at 20° C. and 90% humidity. The plants were scored for disease control after five days.

Grape Downy Mildew (GDM)

*Plasmopara viticola* was maintained, leaves of grape plants, cultivar Delaware, in a controlled temperature chamber at 20° C. in humid air with moderate light intensity for 7 to 8 days. A water suspension of the spores from infested leaves was obtained and the spore concentration was adjusted to about $3\times10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

Rice Blast (RB)

Cultures of *Pyricularia oyrzae* were maintained on potato dextrose agar for two to three week. The spores were washed from the agar with water containing I drop of Tween 80 per 100 After filtering the spore suspension through two layers of cheese cloth, the spore count was adjusted to $5\times10^5$. The spore suspension was sprayed onto 12-day old rice plants, cultivar M-1, using a DeVilbiss atomizer. The inoculated plants were placed in a humidity at chamber 20° C. for 36 hours to allow for infection. After the infection period the plants were placed in the greenhouse. After 6 days, the plants were scored for disease control. Disease control values were recorded as percent control.

Cucumber Downy Mildew (CDM)

Cucumber plants were maintained in the greenhouse. Large, fully expanded leaves were collected from the plates. The stems were wrapped with cotton, the leaves were placed in a large petri plate (15-cm. diameter) and the leaves were supported by glass rods. The upper cover of the plate was removed and the upper surface of the detached cucumber leaf was sprayed with the compounds of the present invention. The leaf was allowed to dry in the air for approximately 2 hours. The cultures of *Pseudoperonospora cubensis* were maintained on cucumber plants. After extracting the spores by shaking the leaves in water, the lower surface of the treated cucumber leaves were sprayed with a spore concentration of 100,000 spores per ml. The plates were returned to a controlled environmental chamber at 20° C. and 90% humidity for five days. After this time, leaves were examined for disease development. Disease control values were recorded as percent control.

Cucumber Anthracnose (CA)

The fungal pathogen *Colletotrichum lagenarium* was cultured on potato dextrose agar (PDA) in the dark at 22 C for a period of 8 to 14 days. Spores of C. lagenarium were removed from the PDA plates by flooding the plate surface with distilled water, amended with 0.5% v/w of yeast extract. The upper surface of the fungal colony was scraped with a blunt instrument until most of the spores were released into the aqueous environment. The spore suspension was filtered though cheesecloth, and the spore count was adjusted by adding more water, containing the yeast extract, until $3.0\times10^6$ spores per ml was achieved.

The chemically-treated cucumber plants were 15-days old, cultivar Bush Champion. The upper leaf surface of the plants were sprayed with the spore suspension until runoff, using a hand-held pump spray bottle. The plants were placed in a fluorescent-lighted mist chamber (12 hr light, 12 hr dark) for 48 hours. After that infection period, the plants were placed in a growth chamber for 3 days at 25 C and 90% humidity. The treated plants were then evaluated for disease control. Disease control values were recorded as percent control.

Botrytis of Sweet Bell Peppers (BOT)

The fungal pathogen *Botrytis cinerea* was cultured on potato dextrose agar (PDA) under fluorescent lights (12 hr on, 12 hr off) for a period of 2 to 3 weeks. Spores of *B. cinerea* were removed from the PDA plates by flooding the plate surface with distilled water, amended with 0.5% v/w of yeast extract. The upper surface of the fungal colony was scraped with a rubber instrument until most of the spores were released into the aqueous environment. The spore suspension was filtered though cheesecloth, and the spore count was adjusted by adding more water, containing the yeast extract, until $3.0\times10^6$ spores per ml was achieved.

Chemically-treated sweet bell pepper plants were 19-days old, cultivar California Wonder. The entire leaf surface of the plants were sprayed with the spore suspension until runoff, using a DeVilbiss atomizer. The plants were placed in a low light mist chamber (12 hr light, 12 hr dark) at 22 C for 4 or 5 days. The treated plants were then evaluated for disease control. Disease control values were recorded as percent control.

When tested against wheat leaf rust at 300 grams per hectare compounds 1.11, 1.22A, 1.22B 1.27, 1.61A, 1.61B, 1.102, 1.105, 1.155, 2.67 and 3.67 exhibited 99% or better control and when tested at 150 grams per hectare compounds 2.11, 2.12A, 2.13A, 2.19, 2.21A, 2.22A, 2.24, 2.25A, 2.27, 2.28, 2.37A, 3.11, 3.11A, 3.12A, 3.13A, 3.20A, 3.25A, 3.26A, 3.37A, 3.28A and 11.50A exhibited 99% or better control.

When tested against wheat leaf blotch at 300 grams per hectare compounds 1.11, 1.22A, 1.27, 1.67, 1.102 and 3.67 exhibited 90% or better control and when tested at 150 grams per hectare compounds 2.11, 2.19, 2.22A, 2.24, 2.26A, 3.11, 3.11A, 3.14A, 3.21A, 3.22A, 3.23A, 3.28A and 12.98A exhibited 90% or better control.

When tested against wheat powdery mildew at 300 grams per hectare compounds 1.11, 1.22A, 1.27, 1.116, 1.116A, 2.67 and 3.67 exhibited 90% or better control and when tested at 150 grams per hectare compounds 2.11, 2.11 A, 2.19, 2.20A, 2.20B, 2.24, 2.25A, 2.26A, 2.27, 2.28, 3.11, 3.11A, 3.12A, 3.14A, 3.19A, 3.20A, 3.24A, 3.28A, 11.50A, 11.50B, 11.98A and 11.98B exhibited 90% or better control.

When tested against cucumber powdery mildew at a dose of 300 grams per hectare compounds 1.11, 1.22A, 1.27, 1.61A, 1.67, 1.102, 1.105, 1.116,2.67and 3.67 exhibited 95% or better control and when tested at 150 grams per hectare compounds 2.11, 2.11A, 2.12A, 2.13A, 2.14A, 2.19, 2.20A, 2.21A, 2.24, 2.25A, 2.26A, 2.27, 2.28, 2.37A, 3.11, 3.11A, 3.11B, 3.12A, 3.14A, 3.19A, 3.20A, 3.22A, 3.23A, 3.24A, 3.26A, 3.28A, 3.34B, 3.37A, 11.50A, 11.98A, 12.50A and 12.98A exhibited 95% or better control.

When tested against tomato late blight at 300 grams per hectare compounds 1.155 and 2.67 exhibited 90% or better control and when tested at 150 grams per hectare compounds 1.14, 2.12A, 2.13A, 2.13B, 2.14A, 2.21A, 2.22A, 2.20B, 2.22B, 2.23A, 2.23B, 2.27, 3.11 A, 3.12A, 3.12B, 3.13A, 3.13B, 3.14B, 3.19A, 3.20A, 3.20B, 3.21B, 3.24A, 3.25A, 3.24B, 3.25B, 3.26A, 3.26B, 3.27, 3.28A, 3.34B, 3.37A, 3.37B, 11.50A, 11.50B, 11.02A, 11.98A, 12.02B, 12.50B, 12.98A, and 12,122A exhibited 90% or better control.

When tested against grape downy mildew at 300 grams per hectare compounds 1.11, 1.22A, 1.22B, 1.27, 1.61B, 1.67, 1.94, 1.105, 1.116, 1.155, 1.159. 1.160, 2.67 and 3.67 exhibited 95% or better control and when tested at 150 grams per hectare compounds 1.133, 2.11, 2.11B, 3.11, 3.11B and 3.34B exhibited 95% or better control.

When tested against rice blast at 300 grams per hectare compounds 1.11, 1.22A, 1.27, 1.67 and 1.102 exhibited 95% or better control and when tested at 150 grams per hectare compounds 1.14, 2.11, 2.11A, 2.14A, 2.12A, 2.13A, 2.19, 2.20A, 2.21A, 2.21B, 2.22A, 2.22B, 2.23A, 2.24, 2.25A, 2.26A, 2.27, 2.28, 2.37A, 3.11, 3.11A, 3.13A, 3.14A, 3.12A, 3.19A, 3.20A, 3.21A, 3.23A, 3.24A, 3.26A, 3.27, 3.28A, 3.37A, 12.60A, 12.50B and 12.98A exhibited 95% or better control.

When tested against cucumber downy mildew at 150 grams per hectare compounds 2.12B, 2.13A, 2.13B, 2.14A, 2.20A, 2.27, 2.28, 3.11, 3.11A, 3.13A, 3.13B, 3.14A, 3.14B, 3.20B, 3.24B, 3.25B, 12.50A, 12.98A, and 12.98B exhibited 95% or better control.

When tested against sweet bell pepper botrytis at 150 grams per hectare compounds 2.14A, 2.18, 2.24, 2.25A, 3.13B, 3.14A, 3.14B, 3.25B and 11.50A exhibited 90% or better control.

When tested against cucumber anthracnose at 300 grams per hectare compounds 1.11, 1.22A, 1.27, 1.102, 1.105 and 3.67 exhibited 95% or better control and when tested at 150 grams per hectare compounds 1.14, 2.12A, 2.13A, 2.20A, 3.11, 3.11A, 3.12A, 3.13A, 3.14A, 3.19A, 3.20A, 3.24A, 3.26A, 3.27, 3.28A, 3.37A, 12.98A exhibited 95% or better control.

The compounds of this invention are useful as agricultural fungicides and, as such, can be applied to various loci such as the seed, the soil or the foliage of plants to be protected.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15). Other known fungicides which an be combined with the compounds of this invention are dimethomorph, cymoxanil, thifluzamide, furalaxyl, ofurace, benalaxyl, oxadixyl, propamocarb, cyprofuram, fenpiclonil, fludioxonil, pyrimethanil, cyprodinil, triticonazole, fluquinconazole, metconazole, spiroxamine, carpropamid, azoxystrobin, kresoxim-methyl, metominostrobin and trifloxystrobin.

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, barley stripe and leaf rust, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast

EXAMPLE 13

Numerous compounds of this invention were tested for insecticidal activity in vivo against the insects described below. The following test method was used to evaluate compounds of the present invention for insecticidal activity. The compound to be evaluated was dissolved in an appropriate solvent, usually a mix of acetone, methanol and water, and sprayed over three excised leaf disks using a flat fan nozzle. After spraying, the leaf disks were allowed to dry. Two disks were infested with the leaf chewing insects (southern armyworm and Mexican bean beetle) and the third leaf disk was already infested with the two-spotted spider mite prior to spraying. The tested insect species were:

AW southern armyworm *Spodotera eridamia*

BB Mexican bean beetle *Epilachna varivestis*

MTA two-spotted spider mite *Teranychus uricate*

Observations as percent control were made by visual inspection 24–48 hours after spraying.

When tested against southern army worm at 300 grams per hectare compounds 1.11, 1.102, and 1.105 provided 90% or better control and when tested at 150 grams per hectare compounds 1.14, 2.19, 2.28, 3.28A provided 90% or better control.

When tested against Mexican bean beetle at 300 grams/hectare compounds 1.11, 1.22A, 1.22B, 1.27, 1.61A, 1.67, 1.94, 1.102, 1.105, 1.116, 1.116A, 2.11, 3.11, provided 90% or better control and when tested at 150 grams per hectare compounds 1.14, 2.11A, 2.12A, 2.19, 2.24, 2.25A, 2.25B, 2.27, 2.28, 2.34, 3.11A, 3.11B, 3.12A, 3.14A, 3.19A, 3.24A, 3.25A, 3.26A, 3.27, 3.28A, 3.33A, 3.34A, 11.02A, 12.02A, 11.50A and 11.98A provided 90 % or better control.

When tested against two-spotted spider mite at 300 grams/hectare compounds 1.11, 1.22A, 1.271.61A, 1.61B, 1.67, 1.94, 1.102, 1.105, 1.116, and 1.116A provided 90% or better control and when tested at 150 grams per hectare compounds 1.14, 2.12A, 2.14A, 2.19, 2.20A, 2.22A, 2.23A, 2.24, 2.26A, 2.27, 2.28, 2.34. 3.12A, 3.14A, 3.19A, 3.20A, 3.23A, 3.26A, 3.27, 3.28A, 3.33A, 3.34 and 11.50A provided 90% or better control.

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as systemic application. Alternatively, the active compound may be applied to the soil and contacted therein with the insects and other pests to be controlled. This means of application is referred to as soil application. In another alternative, the active compound may be foliarly applied to the plants to be freed from insects and other pests which feed on the foliage.

Compositions and formulations according to the present invention may also include known pesticidal compounds. This expands the spectrum of activity of the preparation and may give rise to synergism. Suitable insecticides known in the art include those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. A listing of such adjuvants commonly used in the art, and a discussion of adjuvants, can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001 (1:999,999)–99 (99:1) % by weight. For compositions suitable for storage or transportation, the amount of active ingredient is preferably between about 0.5 (1:199)–90 (9:1) % by weight, and more preferably between about 1 (1:99) –75 (3:1) % by weight of the mixture. Compositions suitable for direct application or field application generally contain the active compound in an amount substantially between about 0.0001 (1:999,999)–95 (19:1) %, preferably between about 0.0005 (1:199,999)–90 (9:1) % by weight, and more preferably between about 0.001 (1:99,999)–75 (3:1) % by weight of the mixture. The composition can also be stated as a ratio of the compound to the carrier. In the present invention the weight ratio of these materials (active compound/carrier) can vary from 99:1 (99%) to 1:4 (20%) and more preferably from 10:1 (91%) to 1:3 (25%).

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clay, inorganic silicate and carbonate, and silica and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide and 5 parts of sodium lignosulfonate. In another preparation a kaolin type (Barden) clay is used in place of the synthetic precipitated hydrated silicon dioxide in the above wettable powder, and in another such preparation 25% of the silicon dioxide is replaced with a synthetic sodium silicoaluminate.

Dusts are prepared by mixing compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combating or controlling pests which comprises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:
1. A compound of the formula:

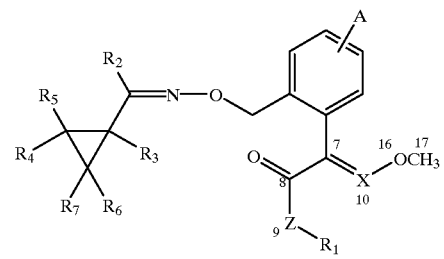

wherein X is N or CH; Z is O, S or $NR_8$;

A is selected from the group consisting of hydrogen, halo, cyano, $(C_1-C_{12})$alkyl, and $(C_1-C_{12})$alkoxy;

$R_1$ and $R_8$ are independently selected from the group consisting of hydrogen and $(C_1-C_4)$alkyl;

$R_2$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, heterocyclic$(C_1-C_4)$alkyl and $C(R_{10})$=N—$OR_9$;

$R_3$ is selected from the group consisting of hydrogen, $(C_1-C_{12})$alkyl, halo$(C_1-C_{12})$alkyl, $(C_3-C_7)$cycloalkyl, halo($C_3$–$C_7$)cycloalkyl, ($C_2$–$C_8$)alkenyl, halo($C_2$–$C_8$) alkenyl, ($C_2$–$C_8$)alkynyl, halo($C_2$–$C_8$)alkynyl, aryl, aralkyl, aryl($C_3$–$C_7$)cycloalkyl, heterocyclic and heterocyclic($C_1$–$C_4$)alkyl;

$R_4$ and $R_5$ are independently selected from the group consisting of hydrogen, ($C_1$–$C_{12}$)alkyl, halo($C_1$–$C_{12}$) alkyl, ($C_3$–$C_7$)cycloalkyl, halo($C_3$–$C_7$)cycloalkyl, ($C_2$–$C_8$)alkenyl, halo($C_2$–$C_8$)alkenyl, ($C_2$–$C_8$)alkynyl, halo($C_2$–$C_8$)alkynyl, halo, cyano, ($C_1$–$C_4$) alkoxycarbonyl, aryl, aralkyl, aryl($C_3$–$C_7$)cycloalkyl, aryl($C_2$–$C_8$)alkenyl, heterocyclic or heterocyclic ($C_1$–$C_4$)alkyl;

$R_6$ is selected from the group consisting of hydrogen, ($C_1$–$C_{12}$)alkyl, halo($C_1$–$C_{12}$)alkyl, ($C_3$–$C_7$)cycloalkyl, halo($C_3$–$C_7$)cycloalkyl, ($C_2$–$C_8$)alkenyl, halo($C_1$–$C_8$) alkenyl, ($C_2$–$C_8$)alkynyl, halo($C_2$–$C_8$)alkynyl, halo, cyano, ($C_1$–$C_4$)alkoxycarbonyl, aryl, aralkyl, aryl ($C_3$–$C_7$)cycloalkyl, aryl($C_2$–$C_8$)alkenyl, heterocyclic and heterocyclic($C_1$–$C_4$)alkyl;

$R_7$ is selected from the group consisting of aryl, aralkyl, heterocyclic and heterocyclic($C_1$–$C_4$)alkyl;

$R_9$ is selected from the group consisting of hydrogen, ($C_1$–$C_{12}$)alkyl, halo($C_1$–$C_{12}$)alkyl, ($C_2$–$C_8$)alkenyl, halo($C_2$–$C_8$)alkenyl, ($C_2$–$C_8$)alkynyl, halo($C_2$–$C_8$) alkynyl, ($C_1$–$C_4$)alkylcarbonyl, ($C_1$–$C_4$) alkoxycarbonyl, aryl, and aralkyl;

$R_{10}$ is independently selected from the group consisting of hydrogen, ($C_1$–$C_{12}$)alkyl, halo($C_1$–$C_{12}$)alkyl, ($C_3$–$C_7$) cycloalkyl, halo($C_3$–$C_7$)cycloalkyl, ($C_2$–$C_8$)alkenyl, halo($C_2$–$C_8$)alkenyl, ($C_2$–$C_8$)alkynyl, halo($C_2$–$C_8$) alkynyl, aryl, aralkyl, heterocyclic, and heterocyclic ($C_1$–$C_4$)alkyl and enantiomers, stereoisomers, and agronomically acceptable salts thereof.

2. The compound of claim 1 wherein X is CH, Z is O, $R_2$ is ($C_1$–$C_{12}$)alkyl, and $R_3$ is H or ($C_1$–$C_4$)alkyl.

3. The compound of claim 2 wherein $R_7$ is selected from the group consisting of phenyl, 2-chlorophenyl, 2-fluorophenyl, 2-trifluoromethylphenyl, 3-chlorophenyl, 3-fluorophenyl, 3-trifluoromethylphenyl, 4-chlorophenyl, 4-fluorophenyl, 4-trifluoromethylphenyl and 2,4-dichlorophenyl.

4. The compound of claim 1 wherein X is N, Z is O or NH, $R_2$ is ($C_1$–$C_{12}$)alkyl and $R_3$ is H or ($C_1$–$C_4$)alkyl.

5. The compound of claim 4 wherein $R_7$ is selected from the group consisting of phenyl, 2-chlorophenyl, 2-fluorophenyl, 2-trifluoromethylphenyl, 3-chlorophenyl, 3-fluorophenyl, 3-trifluoromethylphenyl, 4-chlorophenyl, 4-fluorophenyl, 4-trifluoromethylphenyl and 2,4-dichlorophenyl.

6. The compound of claim 1 where the compound is where the compound is N-methyl-2-[2-((((trans-1-(2-(3'-trifluoromethylphenyl)cyclopropyl)ethylidene)-amino)oxy) methyl)phenyl]-2-methoxyiminoacetamide.

7. The compound of claim 1 where the compound is N-methyl-2-[2-((((trans-1-(2-(4'-chlorophenyl) cyclopropyl)ethylidene)amino)oxy)methyl)phenyl]-2-methoxyiminoacetamide.

8. A fungicidal composition for controlling phytopathogenic fungi which comprises an agronomically acceptable carrier and the compound of claim 1 wherein the ratio of the carrier to the compound is between 99:1 and 1:4.

9. A method for controlling phytopathogenic fungi which comprises applying the compound of claim 1 to the locus where control is desired, at a rate of from 0.005 to 50 kilograms per hectare.

10. A method for controlling insects which comprises applying to the insects' habitat the compound of claim 1 at a rate of from 0.005 to 10 kilograms per hectare.

* * * * *